US011419937B2

(12) United States Patent
Harris et al.

(10) Patent No.: US 11,419,937 B2
(45) Date of Patent: *Aug. 23, 2022

(54) DELIVERY OF NANOPARTICLES

(71) Applicant: Sebacia, Inc., Duluth, GA (US)

(72) Inventors: Todd James Harris, Carlsbad, CA (US); Alice Ann Chen Kim, San Francisco, CA (US)

(73) Assignee: CORONADO AESTHETICS, LLC, Southlake, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,982

(22) Filed: Nov. 27, 2019

(65) Prior Publication Data
US 2020/0155681 A1 May 21, 2020

Related U.S. Application Data

(63) Continuation of application No. 15/432,073, filed on Feb. 14, 2017, now Pat. No. 10,537,640, which is a continuation of application No. 14/321,509, filed on Jul. 1, 2014, now Pat. No. 9,572,880, which is a continuation-in-part of application No. 14/020,423, filed on Sep. 6, 2013, now Pat. No. 8,834,933, which is a continuation of application No. 13/219,514, filed on Aug. 26, 2011, now Pat. No. 9,061,056.

(60) Provisional application No. 61/402,305, filed on Aug. 27, 2010, provisional application No. 61/422,612, filed on Dec. 13, 2010, provisional application No. 61/516,308, filed on Apr. 1, 2011, provisional application No. 61/870,103, filed on Aug. 26, 2013.

(51) Int. Cl.
A61K 41/00 (2020.01)
A61B 18/20 (2006.01)
A61K 8/02 (2006.01)
A61M 37/00 (2006.01)
A61K 8/29 (2006.01)
A61N 5/06 (2006.01)
A61Q 9/04 (2006.01)
A61B 17/00 (2006.01)
A61Q 19/06 (2006.01)
A61Q 19/08 (2006.01)
A61K 9/00 (2006.01)
A61K 9/51 (2006.01)
B82Y 5/00 (2011.01)
A61B 18/00 (2006.01)
A61B 17/54 (2006.01)
A61N 5/067 (2006.01)

(52) U.S. Cl.
CPC ........ A61K 41/0047 (2013.01); A61B 18/203 (2013.01); A61K 8/0245 (2013.01); A61K 8/0283 (2013.01); A61K 8/29 (2013.01); A61M 37/0092 (2013.01); A61N 5/062 (2013.01); A61N 5/0616 (2013.01); A61Q 9/04 (2013.01); A61B 17/54 (2013.01); A61B 2017/00747 (2013.01); A61B 2017/00752 (2013.01); A61B 2018/0047 (2013.01); A61B 2018/00476 (2013.01); A61B 2018/00577 (2013.01); A61K 9/0009 (2013.01); A61K 9/009 (2013.01); A61K 9/0014 (2013.01); A61K 9/0019 (2013.01); A61K 9/5115 (2013.01); A61K 2800/413 (2013.01); A61K 2800/621 (2013.01); A61K 2800/624 (2013.01); A61K 2800/81 (2013.01); A61N 2005/067 (2013.01); A61N 2005/0659 (2013.01); A61Q 19/06 (2013.01); A61Q 19/08 (2013.01); B82Y 5/00 (2013.01)

(58) Field of Classification Search
None
See application file for complete search history.

(56) References Cited

U.S. PATENT DOCUMENTS

| | | |
|---|---|---|
| 4,526,698 A | 7/1985 | Kuroda et al. |
| 5,226,907 A | 7/1993 | Tankovich |
| 5,385,729 A | 1/1995 | Prencipe et al. |
| 5,409,797 A | 4/1995 | Hosoi et al. |
| 5,423,337 A | 6/1995 | Ahlert et al. |
| 5,423,803 A | 6/1995 | Tankovich et al. |
| 5,425,728 A | 6/1995 | Tankovich |
| 5,553,630 A | 9/1996 | Dupuis et al. |
| 5,562,643 A | 10/1996 | Johnson |
| 5,593,680 A | 1/1997 | Bara et al. |
| 5,647,866 A | 7/1997 | Zains et al. |
| 5,655,547 A | 8/1997 | Karni |
| 5,695,747 A | 12/1997 | Forestier et al. |
| 5,713,845 A | 2/1998 | Tankovich |
| 5,750,120 A | 5/1998 | Miguel-Colombel |
| 5,752,949 A | 5/1998 | Tankovich et al. |

(Continued)

FOREIGN PATENT DOCUMENTS

| | | |
|---|---|---|
| DE | 3905167 | 8/1989 |
| DE | 4344141 | 7/1995 |

(Continued)

OTHER PUBLICATIONS

U.S. Appl. No. 13/219,514 Issued U.S. Pat. No. 9,061,056, Compositions and Methods for Targeted Thermomodulation, filed Aug. 26, 2011.
U.S. Appl. No. 14/020,423 Issued U.S. Pat. No. 8,834,933, Thermal Treatment of Acne With Nanoparticles, filed Sep. 6, 2013.
U.S. Appl. No. 14/020,387 Issued U.S. Pat. No. 8,821,940, Thermal Treatment of the Skin Surface With Nanoparticles, filed Sep. 6, 2013.
U.S. Appl. No. 14/020,481 Issued U.S. Pat. No. 8,821,941, Hair Removal With Nanoparticles, filed Sep. 6, 2013.

(Continued)

Primary Examiner — Celeste A Roney
(74) Attorney, Agent, or Firm — Edwin S. Flores; Daniel J. Chalker; Chalker Flores, LLP

(57) ABSTRACT

Delivery of compositions for treatment of skin tissue with photoactive plasmonic nanoparticles and light, with embodiments relating to delivery devices. Treatments are useful for cosmetic, diagnostic and therapeutic applications.

15 Claims, 23 Drawing Sheets

(56) References Cited

U.S. PATENT DOCUMENTS

| | | |
|---|---|---|
| 5,756,110 A | 5/1998 | Allard et al. |
| 5,759,767 A | 6/1998 | Lakowicz |
| 5,776,440 A | 7/1998 | Forestier et al. |
| 5,810,801 A | 9/1998 | Anderson et al. |
| 5,814,311 A | 9/1998 | Le Bras-Roulier et al. |
| 5,817,089 A | 10/1998 | Tankovich et al. |
| 5,830,177 A | 11/1998 | Li et al. |
| 5,858,381 A | 1/1999 | Le Bras et al. |
| 5,863,522 A | 1/1999 | Forestier et al. |
| 5,925,035 A | 7/1999 | Tankovich |
| 5,955,091 A | 9/1999 | Hansenne |
| 5,958,389 A | 9/1999 | Le Bras-Roulier et al. |
| 5,985,300 A | 11/1999 | Crotty et al. |
| 6,004,567 A | 12/1999 | Marchi-Lemann et al. |
| 6,036,684 A | 3/2000 | Tankovich et al. |
| 6,050,990 A | 4/2000 | Tankovich et al. |
| 6,060,041 A | 5/2000 | Candau et al. |
| 6,063,074 A | 5/2000 | Tankovich |
| 6,080,127 A | 6/2000 | Li et al. |
| 6,132,392 A | 10/2000 | Stone |
| 6,132,745 A | 10/2000 | Marchi-Lemann et al. |
| 6,147,982 A | 11/2000 | Sourour et al. |
| 6,152,917 A | 11/2000 | Tankovich |
| 6,165,440 A | 12/2000 | Esenaliev |
| 6,168,590 B1 | 1/2001 | Neev |
| 6,183,728 B1 | 2/2001 | Forestier et al. |
| 6,183,773 B1 | 2/2001 | Anderson |
| 6,235,270 B1 | 5/2001 | Ishii et al. |
| 6,238,650 B1 | 5/2001 | Lapidot et al. |
| 6,267,771 B1 | 7/2001 | Tankovich |
| 6,283,956 B1 | 9/2001 | McDaniel |
| 6,287,549 B1 | 9/2001 | Sumian et al. |
| 6,333,026 B1 | 12/2001 | Lemann |
| 6,344,050 B1 | 2/2002 | Chen |
| 6,344,272 B1 | 2/2002 | Oldenburg et al. |
| 6,355,054 B1 | 3/2002 | Neuberger |
| 6,365,145 B1 | 4/2002 | Ben-Hur et al. |
| 6,403,653 B1 | 6/2002 | Hobson et al. |
| 6,410,603 B1 | 6/2002 | Hobson et al. |
| 6,428,811 B1 | 8/2002 | West et al. |
| 6,461,595 B1 | 10/2002 | Leo et al. |
| 6,491,929 B1 | 12/2002 | Anderson |
| 6,517,820 B1 | 2/2003 | Robert |
| 6,521,241 B1 | 2/2003 | Minerath, III et al. |
| 6,530,944 B2 | 3/2003 | West et al. |
| 6,534,044 B1 | 3/2003 | Wada et al. |
| 6,541,017 B1 | 4/2003 | Lemann et al. |
| 6,589,538 B1 | 7/2003 | Lemann et al. |
| 6,600,951 B1 | 7/2003 | Anderson |
| 6,611,707 B1 | 8/2003 | Prausnitz et al. |
| 6,620,407 B1 | 9/2003 | Gers-Barlag et al. |
| 6,645,517 B2 | 11/2003 | West et al. |
| 6,660,381 B2 | 12/2003 | Halas et al. |
| 6,663,658 B1 | 12/2003 | Kollias et al. |
| 6,676,655 B2 | 1/2004 | McDaniel |
| 6,685,730 B2 | 2/2004 | West et al. |
| 6,685,927 B2 | 2/2004 | Sumian et al. |
| 6,685,986 B2 | 2/2004 | Oldenburg et al. |
| 6,692,755 B2 | 2/2004 | Gers-Barlag et al. |
| 6,699,724 B1 | 3/2004 | West et al. |
| 6,706,032 B2 | 3/2004 | Weaver et al. |
| 6,720,006 B2 | 4/2004 | Hanke et al. |
| 6,767,547 B2 | 7/2004 | Gers-Barlag et al. |
| 6,793,913 B2 | 9/2004 | Tournilhac et al. |
| 6,800,122 B2 | 10/2004 | Anderson et al. |
| 6,803,049 B2 | 10/2004 | Gers-Barlag et al. |
| 6,811,770 B2 | 11/2004 | Ferrari et al. |
| 6,814,760 B2 | 11/2004 | Anderson et al. |
| 6,821,509 B2 | 11/2004 | Soane et al. |
| 6,838,088 B2 | 1/2005 | Gers-Barlag et al. |
| 6,852,252 B2 | 2/2005 | Halas et al. |
| 6,881,249 B2 | 4/2005 | Anderson et al. |
| 6,887,260 B1 | 5/2005 | McDaniel |
| 6,897,238 B2 | 5/2005 | Anderson |
| 6,942,878 B2 | 9/2005 | Ishii et al. |
| 6,955,639 B2 | 10/2005 | Hainfeld et al. |
| 6,989,151 B2 | 1/2006 | Gers-Barlag et al. |
| 7,008,647 B2 | 3/2006 | Burrell et al. |
| 7,018,396 B2 | 3/2006 | Sierra et al. |
| 7,037,513 B1 | 5/2006 | Traynor et al. |
| 7,081,128 B2 | 7/2006 | Hart |
| 7,131,446 B2 | 11/2006 | Tang et al. |
| 7,144,627 B2 | 12/2006 | Halas et al. |
| 7,201,765 B2 | 4/2007 | McDaniel |
| 7,270,721 B2 | 9/2007 | Hilfenhaus et al. |
| 7,328,708 B2 | 2/2008 | Malak |
| 7,367,934 B2 | 5/2008 | Hainfeld et al. |
| 7,371,457 B2 | 5/2008 | Oldenburg et al. |
| 7,435,524 B2 | 10/2008 | Anderson et al. |
| 7,462,496 B2 | 12/2008 | Malak |
| 7,492,458 B2 | 2/2009 | Malak |
| 7,494,503 B2 | 2/2009 | McDaniel |
| 7,530,940 B2 | 5/2009 | Hainfeld et al. |
| 7,648,595 B2 | 1/2010 | Jin et al. |
| 7,659,301 B2 | 2/2010 | Anderson |
| 7,704,754 B2 | 4/2010 | Malak |
| 7,758,561 B2 | 7/2010 | Eppstein |
| 7,758,888 B2 | 7/2010 | Lapidot et al. |
| 7,776,130 B2 | 8/2010 | Mirkin et al. |
| 7,780,955 B2 | 8/2010 | Cassin |
| 7,785,623 B2 | 8/2010 | Keller |
| 7,790,066 B2 | 9/2010 | Wang et al. |
| 7,829,073 B2 | 11/2010 | Martin et al. |
| 7,959,624 B2 | 6/2011 | Riesinger |
| 8,033,977 B2 | 10/2011 | Hainfeld et al. |
| 8,057,418 B2 | 11/2011 | Korbling et al. |
| 8,062,701 B2 | 11/2011 | McClure et al. |
| 8,118,032 B2 | 2/2012 | Malak |
| 8,178,202 B2 | 5/2012 | Hales et al. |
| 8,182,786 B2 | 5/2012 | O'Brien et al. |
| 8,197,471 B1 | 6/2012 | Tersigni |
| 8,268,332 B2 | 9/2012 | Manstein |
| 8,268,638 B2 | 9/2012 | Stein et al. |
| 8,285,391 B2 | 10/2012 | Malak |
| 8,377,427 B2 | 2/2013 | Giroud et al. |
| 8,420,062 B2 | 4/2013 | Josso |
| 8,518,445 B2 | 8/2013 | Alfano et al. |
| 8,591,924 B2 | 11/2013 | Zheng |
| 8,613,913 B2 | 12/2013 | Chang et al. |
| 8,617,580 B2 | 12/2013 | Toledano et al. |
| 8,652,495 B2 | 2/2014 | Porter et al. |
| 8,802,154 B2 | 8/2014 | Harris et al. |
| 8,821,940 B2 | 9/2014 | Harris et al. |
| 8,821,941 B2 | 9/2014 | Harris et al. |
| 8,834,447 B2 | 9/2014 | Chen et al. |
| 8,834,933 B2 | 9/2014 | Harris et al. |
| 8,871,711 B2 | 10/2014 | Cotsarelis et al. |
| 8,895,071 B1 | 11/2014 | Harris et al. |
| 8,906,418 B1 | 12/2014 | Harris et al. |
| 8,961,450 B2 | 2/2015 | Anderson et al. |
| 9,061,056 B2 | 6/2015 | Harris et al. |
| 9,212,294 B2 | 12/2015 | Oldenburg et al. |
| 9,249,334 B2 | 2/2016 | Oldenburg et al. |
| 9,421,259 B2 | 8/2016 | Harris et al. |
| 9,421,260 B2 | 8/2016 | Harris et al. |
| 9,421,261 B2 | 8/2016 | Harris et al. |
| 9,427,467 B2 | 8/2016 | Harris et al. |
| 9,433,676 B2 | 9/2016 | Harris et al. |
| 9,433,677 B2 | 9/2016 | Harris et al. |
| 9,433,678 B2 | 9/2016 | Harris et al. |
| 9,439,964 B2 | 9/2016 | Harris et al. |
| 9,439,965 B2 | 9/2016 | Harris et al. |
| 9,446,126 B2 | 9/2016 | Harris et al. |
| 9,572,880 B2 | 2/2017 | Harris et al. |
| 2001/0002275 A1 | 5/2001 | Oldenburg et al. |
| 2002/0009488 A1 | 1/2002 | Francis et al. |
| 2002/0034480 A1 | 3/2002 | Grimm et al. |
| 2002/0041854 A1 | 4/2002 | Hadasch et al. |
| 2002/0061363 A1 | 5/2002 | Halas et al. |
| 2002/0103517 A1 | 8/2002 | West et al. |
| 2002/0132045 A1 | 9/2002 | Halas et al. |
| 2002/0187172 A1 | 12/2002 | Reb et al. |
| 2002/0192298 A1 | 12/2002 | Burrell et al. |
| 2003/0060811 A1 | 3/2003 | McDaniel |

(56) References Cited

U.S. PATENT DOCUMENTS

| | | |
|---|---|---|
| 2003/0072728 A1 | 4/2003 | Soane et al. |
| 2003/0095941 A1 | 5/2003 | Anderson |
| 2003/0099718 A1 | 5/2003 | Burrell et al. |
| 2003/0118657 A1 | 6/2003 | West et al. |
| 2003/0156991 A1 | 8/2003 | Halas et al. |
| 2003/0167080 A1 | 9/2003 | Hart et al. |
| 2003/0170189 A1 | 9/2003 | Victor |
| 2003/0215638 A1 | 11/2003 | Charnay et al. |
| 2004/0006328 A1 | 1/2004 | Anderson |
| 2004/0151673 A1 | 8/2004 | Josso |
| 2004/0157237 A1 | 8/2004 | Malak et al. |
| 2004/0166508 A1 | 8/2004 | Pawlak et al. |
| 2004/0170579 A1 | 9/2004 | Mobius |
| 2004/0197286 A1 | 10/2004 | Robert et al. |
| 2004/0219179 A1 | 11/2004 | McDaniel |
| 2004/0253138 A1 | 12/2004 | Malak |
| 2004/0253757 A1 | 12/2004 | Gourlaouen et al. |
| 2005/0031655 A1 | 2/2005 | Karpov |
| 2005/0031658 A1 | 2/2005 | Girier Dufournier et al. |
| 2005/0037034 A1 | 2/2005 | Rhoades |
| 2005/0044642 A1 | 3/2005 | Butcher |
| 2005/0048546 A1 | 3/2005 | Penn et al. |
| 2005/0049582 A1 | 3/2005 | DeBenedictis et al. |
| 2005/0053629 A1 | 3/2005 | Ueda et al. |
| 2005/0058672 A1 | 3/2005 | Gupta |
| 2005/0058678 A1 | 3/2005 | Ricard et al. |
| 2005/0059030 A1 | 3/2005 | Bao et al. |
| 2005/0130324 A1 | 6/2005 | West et al. |
| 2005/0137656 A1 | 6/2005 | Malak |
| 2005/0142605 A1 | 6/2005 | Malak |
| 2005/0146724 A1 | 7/2005 | Malak |
| 2005/0164169 A1 | 7/2005 | Malak |
| 2005/0169866 A1 | 8/2005 | Hannich et al. |
| 2005/0175649 A1 | 8/2005 | Disalvo et al. |
| 2005/0177093 A1 | 8/2005 | Barry et al. |
| 2005/0186235 A1 | 8/2005 | Martin et al. |
| 2005/0186565 A1 | 8/2005 | Malak |
| 2005/0187128 A1 | 8/2005 | Martin et al. |
| 2005/0203495 A1 | 9/2005 | Malak |
| 2005/0220741 A1 | 10/2005 | Dumousseaux |
| 2005/0229334 A1 | 10/2005 | Huang et al. |
| 2005/0256554 A1 | 11/2005 | Malak |
| 2005/0283145 A1 | 12/2005 | Malak |
| 2006/0078578 A1 | 4/2006 | Sandewicz et al. |
| 2006/0083762 A1 | 4/2006 | Brun et al. |
| 2006/0257336 A1 | 11/2006 | Ferrari et al. |
| 2007/0032781 A1 | 2/2007 | Henry et al. |
| 2007/0065387 A1 | 3/2007 | Beck et al. |
| 2007/0078290 A1 | 4/2007 | Esenaliev |
| 2007/0092471 A1 | 4/2007 | Cassier et al. |
| 2007/0104605 A1 | 5/2007 | Hampden-Smith et al. |
| 2007/0125383 A1 | 6/2007 | Ko |
| 2007/0154903 A1 | 7/2007 | Marla et al. |
| 2007/0158611 A1 | 7/2007 | Oldenburg |
| 2007/0160636 A1 | 7/2007 | Kasai |
| 2007/0160896 A1 | 7/2007 | Malak et al. |
| 2007/0166248 A1 | 7/2007 | L'Alloret et al. |
| 2007/0183992 A1 | 8/2007 | Dumousseaux et al. |
| 2007/0196305 A1 | 8/2007 | Wang et al. |
| 2007/0208400 A1 | 9/2007 | Nadkarni et al. |
| 2007/0217996 A1 | 9/2007 | Levy et al. |
| 2007/0231940 A1 | 10/2007 | Gourlaouen et al. |
| 2008/0045865 A1 | 2/2008 | Kislev |
| 2008/0050448 A1 | 2/2008 | Wilson et al. |
| 2008/0077203 A1 | 3/2008 | Malak |
| 2008/0188558 A1 | 8/2008 | Godal et al. |
| 2008/0204742 A1 | 8/2008 | Halas et al. |
| 2008/0208179 A1 | 8/2008 | Chan et al. |
| 2008/0214988 A1 | 9/2008 | Altshuler et al. |
| 2008/0233060 A1 | 9/2008 | Grune |
| 2008/0234535 A1 | 9/2008 | Malak et al. |
| 2008/0241262 A1 | 10/2008 | Lee et al. |
| 2008/0248001 A1 | 10/2008 | Bourke |
| 2008/0288007 A1 | 11/2008 | Malak |
| 2008/0294116 A1 | 11/2008 | Wolter et al. |
| 2008/0305337 A1 | 12/2008 | Berning et al. |
| 2009/0012445 A1 | 1/2009 | Malak |
| 2009/0022765 A1 | 1/2009 | Chung et al. |
| 2009/0022766 A1 | 1/2009 | Geddes |
| 2009/0053268 A1 | 2/2009 | DePablo et al. |
| 2009/0071168 A1 | 3/2009 | Malak |
| 2009/0123509 A1 | 5/2009 | Berkland et al. |
| 2009/0130445 A1 | 5/2009 | Malak |
| 2009/0175915 A1 | 7/2009 | Maitra et al. |
| 2009/0177122 A1 | 7/2009 | Peterson |
| 2009/0217465 A1 | 9/2009 | Cremer et al. |
| 2009/0226521 A1 | 9/2009 | Smyth et al. |
| 2009/0246142 A1 | 10/2009 | Bhatia et al. |
| 2009/0291107 A1 | 11/2009 | Schehlmann et al. |
| 2009/0326358 A1 | 12/2009 | Malak |
| 2009/0326614 A1 | 12/2009 | Ei-Sayed et al. |
| 2010/0002282 A1 | 1/2010 | Agrawal et al. |
| 2010/0016782 A1 | 1/2010 | Oblong |
| 2010/0016783 A1 | 1/2010 | Bourke, Jr. et al. |
| 2010/0040549 A1 | 2/2010 | Halas et al. |
| 2010/0049178 A1 | 2/2010 | Deem et al. |
| 2010/0055138 A1 | 3/2010 | Margulies |
| 2010/0056485 A1 | 3/2010 | Park |
| 2010/0057068 A1 | 3/2010 | Lee |
| 2010/0104652 A1 | 4/2010 | Biris et al. |
| 2010/0119610 A1 | 5/2010 | Schoen et al. |
| 2010/0143431 A1 | 6/2010 | Landau et al. |
| 2010/0172994 A1 | 7/2010 | Sigmund et al. |
| 2010/0174223 A1 | 7/2010 | Sakamoto et al. |
| 2010/0204686 A1 | 8/2010 | Yarolslavksy et al. |
| 2010/0224026 A1 | 9/2010 | Brennan Fournet et al. |
| 2010/0233222 A1 | 9/2010 | Girier Dufournier et al. |
| 2010/0254920 A1 | 10/2010 | L'Alloret et al. |
| 2010/0260700 A1 | 10/2010 | Dop |
| 2010/0266647 A1 | 10/2010 | Dingley et al. |
| 2010/0266649 A1 | 10/2010 | Maitra et al. |
| 2010/0272789 A1 | 10/2010 | Satoh et al. |
| 2010/0284924 A1 | 11/2010 | Zink et al. |
| 2010/0291166 A1 | 11/2010 | Guyot-Ferreol et al. |
| 2010/0291224 A1 | 11/2010 | Tong et al. |
| 2010/0298758 A1 | 11/2010 | Christansen et al. |
| 2010/0303716 A1 | 12/2010 | Jin et al. |
| 2010/0305495 A1 | 12/2010 | Anderson et al. |
| 2010/0323996 A1 | 12/2010 | Ute et al. |
| 2011/0021970 A1 | 1/2011 | Vo-Dinh et al. |
| 2011/0034855 A1 | 2/2011 | Esenaliev |
| 2011/0052672 A1 | 3/2011 | Krishnan et al. |
| 2011/0091572 A1 | 4/2011 | Davidson |
| 2011/0097285 A1 | 4/2011 | Malak |
| 2011/0111002 A1 | 5/2011 | Pop |
| 2011/0117202 A1 | 5/2011 | Bourke, Jr. et al. |
| 2011/0144030 A1 | 6/2011 | Ramis Castelltort et al. |
| 2011/0159291 A1 | 6/2011 | Sun et al. |
| 2011/0168200 A1 | 7/2011 | Bourdin et al. |
| 2011/0223255 A1 | 9/2011 | Thiesen et al. |
| 2011/0229559 A1 | 9/2011 | Prestidge et al. |
| 2011/0240556 A1 | 10/2011 | Hoek et al. |
| 2011/0288234 A1 | 11/2011 | Pandey |
| 2011/0306955 A1 | 12/2011 | Thorhauge et al. |
| 2012/0021030 A1 | 1/2012 | Matsufuji et al. |
| 2012/0059307 A1 | 3/2012 | Harris et al. |
| 2012/0101007 A1 | 4/2012 | Ahern et al. |
| 2012/0141380 A1 | 6/2012 | Margel et al. |
| 2012/0283328 A1 | 11/2012 | Modi |
| 2012/0289955 A1 | 11/2012 | Marc |
| 2013/0017238 A1 | 1/2013 | Porter et al. |
| 2013/0022655 A1 | 1/2013 | Sachweh et al. |
| 2013/0023714 A1 | 1/2013 | Johnston et al. |
| 2013/0183244 A1 | 7/2013 | Hanes et al. |
| 2013/0195979 A1 | 8/2013 | Tersigni |
| 2013/0216596 A1 | 8/2013 | Viladot Petit et al. |
| 2013/0225901 A1 | 8/2013 | Krishnan et al. |
| 2013/0251825 A1 | 9/2013 | Berry |
| 2013/0315650 A1 | 11/2013 | Cassin et al. |
| 2013/0315999 A1 | 11/2013 | Paithankar et al. |
| 2013/0323305 A1 | 12/2013 | Paithankar et al. |
| 2013/0338545 A1 | 12/2013 | Azhari et al. |
| 2014/0005593 A1 | 1/2014 | Harris et al. |
| 2014/0012162 A1 | 1/2014 | Harris et al. |

(56) References Cited

U.S. PATENT DOCUMENTS

| | | | |
|---|---|---|---|
| 2014/0012163 | A1 | 1/2014 | Harris et al. |
| 2014/0012183 | A1 | 1/2014 | Harris et al. |
| 2014/0030300 | A1 | 1/2014 | Maitra et al. |
| 2014/0105982 | A1 | 4/2014 | Oldenburg et al. |
| 2014/0120041 | A1 | 5/2014 | Prencipe et al. |
| 2014/0120167 | A1 | 5/2014 | Lapotko et al. |
| 2014/0120168 | A1 | 5/2014 | Oldenburg et al. |
| 2014/0194900 | A1 | 7/2014 | Sedic |
| 2014/0205546 | A1 | 7/2014 | Macoviak |
| 2014/0206712 | A1 | 7/2014 | Gant et al. |
| 2014/0243934 | A1 | 8/2014 | Vo-Dinh et al. |
| 2014/0271889 | A1 | 9/2014 | Messersmith et al. |
| 2014/0303525 | A1 | 10/2014 | Sitharaman |
| 2014/0316387 | A1 | 10/2014 | Harris et al. |
| 2014/0316394 | A1 | 10/2014 | Quidant et al. |
| 2014/0371654 | A1 | 12/2014 | Harris et al. |
| 2014/0371655 | A1 | 12/2014 | Harris et al. |
| 2014/0371656 | A1 | 12/2014 | Harris et al. |
| 2014/0371658 | A1 | 12/2014 | Harris et al. |
| 2014/0371659 | A1 | 12/2014 | Harris et al. |
| 2014/0371661 | A1 | 12/2014 | Harris et al. |
| 2014/0371662 | A1 | 12/2014 | Harris et al. |
| 2014/0371663 | A1 | 12/2014 | Harris et al. |
| 2014/0371664 | A1 | 12/2014 | Harris et al. |
| 2015/0005691 | A1 | 1/2015 | Harris et al. |
| 2015/0045723 | A1 | 2/2015 | Paithankar et al. |
| 2015/0165180 | A1 | 6/2015 | Anderson et al. |
| 2015/0190341 | A1 | 7/2015 | Paithankar et al. |
| 2015/0196359 | A1 | 7/2015 | Paithankar et al. |
| 2015/0196452 | A1 | 7/2015 | Meyer et al. |
| 2015/0196639 | A1 | 7/2015 | Lando et al. |
| 2015/0225599 | A1 | 8/2015 | Oldenburg et al. |
| 2016/0287741 | A1 | 10/2016 | Harris et al. |
| 2016/0310527 | A1 | 10/2016 | Paithankar et al. |
| 2018/0325594 | A1 | 11/2018 | Paithankar |

FOREIGN PATENT DOCUMENTS

| | | |
|---|---|---|
| DE | 10342258 | 4/2005 |
| DE | 10351611 | 8/2005 |
| DE | 102004002990 | 8/2005 |
| DE | 102005007482 | 9/2006 |
| DE | 102007020554 | 10/2008 |
| DE | 10200800684 | 1/2009 |
| DE | 102008052187 | 4/2010 |
| EP | 409690 | 9/1993 |
| EP | 518772 | 11/1994 |
| EP | 518773 | 2/1995 |
| EP | 555460 | 5/1995 |
| EP | 614656 | 10/1996 |
| EP | 586484 | 1/1998 |
| EP | 0601130 | 8/1998 |
| EP | 0712322 | 4/1999 |
| EP | 0925807 | 6/1999 |
| EP | 0860123 | 1/2002 |
| EP | 966954 | 2/2002 |
| EP | 1112325 | 5/2003 |
| EP | 1185242 | 8/2005 |
| EP | 1201219 | 12/2005 |
| EP | 1210600 | 4/2006 |
| EP | 1325730 | 10/2006 |
| EP | 1506764 | 4/2007 |
| EP | 1506763 | 7/2007 |
| EP | 1506765 | 7/2007 |
| EP | 1506766 | 7/2007 |
| EP | 1529513 | 3/2008 |
| EP | 1317245 | 5/2008 |
| EP | 1677843 | 8/2008 |
| EP | 1744789 | 8/2008 |
| EP | 1768749 | 10/2008 |
| EP | 1267801 | 12/2008 |
| EP | 1559393 | 5/2009 |
| EP | 1559394 | 3/2010 |
| EP | 1208005 | 4/2010 |
| EP | 1861465 | 10/2010 |
| EP | 1502574 | 11/2010 |
| EP | 1167462 | 12/2010 |
| EP | 2231283 | 9/2012 |
| EP | 988853 | 10/2012 |
| EP | 1263447 | 6/2013 |
| EP | 2396010 | 8/2013 |
| EP | 2416752 | 9/2013 |
| EP | 1267747 | 1/2014 |
| EP | 1959914 | 5/2014 |
| EP | 2343047 | 1/2016 |
| IE | 20100204 | 10/2010 |
| JP | H09-501087 | 2/1997 |
| JP | 2005-503388 | 2/2005 |
| JP | 2005507887 | 3/2005 |
| JP | 2001505099 | 4/2007 |
| JP | 2007510466 | 4/2007 |
| JP | 200869097 | 3/2008 |
| JP | 2008519642 | 6/2008 |
| JP | 2010-524591 | 7/2010 |
| JP | 2012527967 | 11/2012 |
| KR | 20080004173 | 1/2008 |
| WO | WO1991006894 | 5/1991 |
| WO | WO1995033518 | 12/1995 |
| WO | WO199620698 | 7/1996 |
| WO | WO1996041579 | 12/1996 |
| WO | WO1997000098 | 1/1997 |
| WO | WO199822031 | 5/1998 |
| WO | WO199824507 | 6/1998 |
| WO | WO199946351 | 9/1999 |
| WO | WO200002590 | 1/2000 |
| WO | WO2000040266 | 7/2000 |
| WO | WO200105586 | 1/2001 |
| WO | WO200106257 | 1/2001 |
| WO | WO200158458 | 8/2001 |
| WO | WO2002085385 | 10/2002 |
| WO | WO2003026481 | 4/2003 |
| WO | WO2003026600 | 4/2003 |
| WO | WO2004058352 | 7/2004 |
| WO | WO2004086044 | 10/2004 |
| WO | WO2005046793 | 5/2005 |
| WO | WO2005077329 | 8/2005 |
| WO | WO2005092286 | 10/2005 |
| WO | WO2006051542 | 5/2006 |
| WO | WO2006122222 | 11/2006 |
| WO | WO2008079758 | 7/2008 |
| WO | WO2008079760 | 7/2008 |
| WO | WO2008079898 | 7/2008 |
| WO | WO2008106966 | 9/2008 |
| WO | WO2009061349 | 5/2009 |
| WO | WO2009117124 | 9/2009 |
| WO | WO2009124189 | 10/2009 |
| WO | WO2009130689 | 10/2009 |
| WO | WO2010073260 | 7/2010 |
| WO | WO2010109545 | 9/2010 |
| WO | WO2010116345 | 10/2010 |
| WO | WO2010116346 | 10/2010 |
| WO | WO2010137580 | 12/2010 |
| WO | WO2010144257 | 12/2010 |
| WO | WO2011013101 | 2/2011 |
| WO | WO2011031871 | 3/2011 |
| WO | WO2011095970 | 8/2011 |
| WO | WO2011116963 | 9/2011 |
| WO | WO2012027728 | 3/2012 |
| WO | WO2012035029 | 3/2012 |
| WO | WO2012059944 | 5/2012 |
| WO | WO2013106998 | 7/2013 |
| WO | WO2013106999 | 7/2013 |
| WO | WO2013107000 | 7/2013 |
| WO | WO2013107001 | 7/2013 |
| WO | WO2013107002 | 7/2013 |
| WO | WO2013107349 | 7/2013 |
| WO | WO2013107350 | 7/2013 |
| WO | WO2013107351 | 7/2013 |
| WO | WO2013107352 | 7/2013 |
| WO | WO2013107353 | 7/2013 |
| WO | WO2013107354 | 7/2013 |
| WO | WO2013158278 | 10/2013 |
| WO | WO2013160362 | 10/2013 |
| WO | WO2013169955 | 11/2013 |

(56) References Cited

FOREIGN PATENT DOCUMENTS

| WO | WO2014026142 | 2/2014 |
|----|--------------|--------|
| WO | WO2014052973 | 4/2014 |
| WO | WO2014145784 | 9/2014 |
| WO | WO2017083819 | 5/2017 |

OTHER PUBLICATIONS

U.S. Appl. No. 14/020,599 Issued U.S. Pat. No. 8,802,154, Thermal Treatment of a Pilosebaceous Unit With Nanoparticles, filed Sep. 6, 2013.
U.S. Appl. No. 14/471,348 Issued U.S. Pat. No. 8,895,071, Thermal Treatment of a Pilosebaceous Unit With Coated Metal Nanoparticles, filed Aug. 28, 2014.
U.S. Appl. No. 14/471,377 Issued U.S. Pat. No. 8,906,418, Thermal Treatment of a Pilosebaceous Unit With Nanoparticles With Coatings That Facilitate Selective Removal From the Skin Surface, filed Aug. 28, 2014.
U.S. Appl. No. 14/471,330 Issued U.S. Pat. No. 9,433,677, Thermal Treatment of a Pilosebaceous Unit With Metal Nanoparticles in Surfactant Containing Solutions, filed Aug. 28, 2014.
U.S. Appl. No. 14/471,319 Issued U.S. Pat. No. 9,446,126, Thermal Treatment of Acne With Coated Metal Nanoparticles, filed Aug. 28, 2014.
U.S. Appl. No. 14/471,434 Issued U.S. Pat. No. 9,421,260, Thermal Treatment of Acne With Nanoparticles With Coatings That Facilitate Selective Removal From the Skin Surface, filed Aug. 28, 2014.
U.S. Appl. No. 14/471,350 Issued U.S. Pat. No. 9,433,678, Thermal Treatment of Acne With Metal Nanoparticles in Surfactant Containing Solutions, filed Aug. 28, 2014.
U.S. Appl. No. 14/471,331 Issued U.S. Pat. No. 9,421,259, Hair Removal With Coated Metal Nanoparticles, filed Aug. 28, 2014.
U.S. Appl. No. 14/471,268 Issued U.S. Pat. No. 9,433,676, Hair Removal With Nanoparticles With Coatings That Facilitate Selective Removal From the Skin Surface, filed Aug. 28, 2014.
U.S. Appl. No. 14/471,367 Issued U.S. Pat. No. 9,427,467, Hair Removal With Metal Nanoparticles in Surfactant Containing Solutions, filed Aug. 28, 2014.
U.S. Appl. No. 14/471,402 Issued U.S. Pat. No. 9,439,964, Thermal Treatment of the Skin Surface With Coated Metal Nanoparticles, filed Aug. 28, 2014.
U.S. Appl. No. 14/471,437 Issued U.S. Pat. No. 9,421,261, Thermal Treatment of the Skin Surface With Nanoparticles With Coatings That Facilitate Selective Removal From the Skin Surface, filed Aug. 28, 2014.
U.S. Appl. No. 14/471,429 Issued U.S. Pat. No. 9,439,965, Thermal Treatment of the Skin Surface With Metal Nanoparticles in Surfactant Containing Solutions, filed Aug. 28, 2014.
U.S. Appl. No. 15/267,656, Compositions and Methods for Thermal Skin Treatment With Metal Nanoparticles, filed Sep. 16, 2016.
U.S. Appl. No. 14/321,509 Issued U.S. Pat. No. 9,572,880, Ultrasound Delivery of Nanoparticles filed Jul. 1, 2014.
U.S. Appl. No. 15/432,073 Ultrasound Delivery of Nanoparticles, filed Feb. 14, 2017.
Australia 2011293132, Compositions and Methods for Targeted Thermomodulation, Aug. 26, 2011.
Australia 2016200848, Compositions and Methods for Targeted Thermomodulation, Aug. 26, 2011.
Australia 2017202704, Compositions and Methods for Targeted Thermomodulation, Aug. 26, 2011.
Brazil 102013004902-6, Compositions and Methods for Targeted Thermomodulation, Feb. 28, 2013.
Canada 2,806,592, Compositions and Methods for Targeted Thermomodulation, Aug. 26, 2011.
China 201180041302.8, Compositions and Methods for Targeted Thermomodulation, Aug. 26, 2011.
China 201710456429.5, Compositions and Methods for Targeted Thermomodulation, Aug. 26, 2011.
Europe 11820765.3, Compositions and Methods for Targeted Thermomodulation, Aug. 26, 2011.
Europe 17167242.1, Compositions and Methods for Targeted Thermomodulation, Aug. 26, 2011.
Europe 17167244.7, Compositions and Methods for Targeted Thermomodulation, Aug. 26, 2011.
Europe 17167546.5, Compositions and Methods for Targeted Thermomodulation, Aug. 26, 2011.
Hong Kong 17110976.8, Compositions and Methods for Targeted Thermomodulation, Aug. 26, 2011.
Hong Kong 17110988.4, Compositions and Methods for Targeted Thermomodulation Aug. 26, 2011.
Hong Kong 17110980.2, Compositions and Methods for Targeted Thermomodulation Aug. 26, 2011.
Israel 224390, Compositions and Methods for Targeted Thermomodulation Aug. 26, 2011.
India 1651/DELNP/2013, Compositions and Methods for Targeted Thermomodulation Aug. 26, 2011.
Japan 2013-526193, Compositions and Methods for Targeted Thermomodulation Aug. 26, 2011.
Japan 2016-106112, Compositions and Methods for Targeted Thermomodulation Aug. 26, 2011.
Japan 2017-194820, Compositions and Methods for Targeted Thermomodulation Aug. 26, 2011.
Aherne, et al. "Optical Properties and Growth Aspects of Silver Nanoprisms Produced by Highly Reproducible and Rapid Synthesis at Room Temperature." Advanced Materials, Adv. Funct. Mater. Jul. 9, 2008, v18, 2005-2016.
Alexandrite Laser Hair Removal; Journal of the Japan Society of Aesthetic Surgery, v. 36, No. 1, Jan. 1999.
American Society for Laser Medicine and Surgery Abstracts, 32nd ASLMS Annual Conference, Abstract #LB3 at p. 351, titled Selective Photothermolysis of the Sebaceous Follicle with Gold-Coated Nanoshells for the Treatment of Acne; Kauvar, Lloyd, Cheung, Zabinska, Owczarek, Majewski, Farinelli, Anderson, Sakamoto (Abstract #LB3 at p. 351: Wileyonlinelibrary.com, Wiley Periodicals, Inc. Published Apr. 10, 2012).
Amirthalingam et al. "Use of Silica-Gold Core Shell Structure Nanoparticles for Targeted Drug Delivery System" J. Nanomedic Nanotechnol 2:119, (2011) vol. 2, Issue 6.
Ammad et al. "An assessment of the efficacy of blue light phototherapy in the treatment of acne vulgaris." *J. Cosmet Dermatol*, 2008, 7: 180-188.
Bukasov et al. "Nano Letters—Highly tunable infrared extinction properties of gold nanocrescents." *American Chemical Society*, vol. 7, No. 5 May 2007, published on web Apr. 14, 2007.
Charles et al. "Versatile Solution Phase Triangular Silver Nanoplates for Highly Sensitive Plasmon Resonance Sensing" American Chemical Society NANO, v4, No. 1 p. 55-64, Dec. 23, 2009.
Chen et al. "Controlling 2-dimensional growth of silver nanoplates." Self-Assembled Nanostructured Materials Symposium. Mat. Res. Soc. Symp. Proc. vol. 775, 343-348|xiii+394. (2003).
Chen et al. "Silver nanodisks: Synthesis, characterization, and self-assembly." J. Phys. Chem. B, vol. 106, No. 42, 2002 10777-10781. (Published Sep. 21, 2002).
Chen, et al. "Silver nanoplates: Size control in two dimensions and formation mechanisms." J. Phys. Chem. B 2004, 108, 5500-5506 Journal of Physical Chemistry B, 108, 5500-5506. (Published Apr. 14, 2004).
Chen, et al. "Synthesis and characterization of truncated triangular silver nanoplates." Nano Letters, 2002, 2 (9), 1003-1007. (Published Jul. 26, 2002).
Choudhary and Elsaie, M.L. "Photodynamic therapy in dermatology: a review." *Lasers Med Sci.*, 2009, 24:971-980.
Contrasting Properties of Gold Nanoparticles for Optical Coherence Tomography: Phantom, in vivo studies and Monte Carlo simulation; Zagaynova et al; Phys. Med. Biol. 53 (2008) 499-5009; Published Aug. 18, 2008.
Dierickx, et al. "Photodynamic Therapy for Nevus Sebaceus With Topical d-Aminolevulinic Acid", Arch Dermatol, vol. 135, Jun. 1993, pp. 637-640.
Divaris, et al. "Phototoxic Damage to Sebaceous Glands and Hair Follicles of Mice After Systemic Administration of 5-Aminolevulinic

(56) References Cited

OTHER PUBLICATIONS

Acid Correlates with Localized Protoporphyrin IX Florescence", American Journal of Pathology, vol. 136, No. 4, Apr. 1990, pp. 891-897.

Donnelly et al. "Photosensitiser delivery for photodynamic therapy. Part 1: Topical carrier platforms." *Expert Opin Drug Deliv.* 2008, 5:757-766.

Ghaffarpour, Azizjalali M. et al., "CO2 Laser therapy versus cryotherapy in treatment of genital warts; a Randomized Controlled Trial (RCT)", Iranian Journal of Microbiology, vol. 4, No. 4, Dec. 2012, 187-190.

Gollnick et al. "Can we define acne as a chronic disease? If so, how and when?" *Am J Clin Dermatol*, 2008, 9:279-284.

Grachtchouk et al. "Basal cell carcinomas in mice arise from hair follicle stem cells and multiple epithelial progenitor populations." *J Clin Invest*, 2011, 121: 1768-1781.

Grams et al. "Permeant lipophilicity and vehicle composition influence accumulation of dyes in hair follicles of human skin," *Eur J Pharm Sci*, 2003, 18:329-336.

Hao E. K., et al. "Synthesis of Silver Nanodisks using Polystyrene Mesospheres as Templates." J Am Chem Soc, 124, 15182-15183. (Published Nov. 22, 2002).

Hao E., et al. "Synthesis and optical properties of anisotropic metal nanoparticles." Journal of Fluorescence, vol. 14, No. 4, Jul. 2004, 331-341. (Published Jul. 2004).

He et al. "Surface Plasmon Resonances of Silver Triangle Nanoplates: Graphic Assignments of Resonance Modes and Linear Fittings of Resonance Peaks" J. Phys. Chem. B 2005, 109, 17503-17511 (Published Aug. 20, 2005).

He, et al. "The evidence for synthesis of truncated silver nanoplates in the presence of CTAB." Materials Characterization, 59, 380-384. (Published 2008).

Hongcharu, et al. "Topical ALA-Photodynamic Therapy for the Treatment of Acne Vulgaris", Journal of Invest. Dermatology, vol. 115, No. 2, Aug. 2000, pp. 183-192 (10 pages).

Huang et al. Microemulsification of triglyceride sebum and the role of interfacial structure on bicontinuous phase behavior.: *Langmuir*, 2004, 20:3559-3563.

Jiang et al. "A self-seeding coreduction method for shape control of silver nanoplates" Nanotechnology 17 (2006) 4929-4935 (Published Sep. 11, 2006).

Jin et al. "Photoinduced Conversion of Silver Nanospheres to Nanoprisms." Science, v 294, 1901-1903. (Published Nov. 30, 2001).

Jin, et al. "Controlling anisotropic nanoparticle growth through plasmon excitation." Nature, v. 425, 487-490 (Published Oct. 2, 2003).

Kjeldstad, et al. "Changes in Polyphosphate Composition and Localization in Propionibacterium Acnes After Near-Ultraviolet Irradiation", Canadian Journal of Microbiology, vol. 37, No. 7, Jul. 1991, 562-567 (Abstract, 1 Page).

Knorr et al. "Follicular transport route-research progress and future perspectives." *Eur J Pharm Biopharm*, 2009, 71:173-180.

Koenig, et al. "Photodynamic-Induced Inactivation of Propionibacterium Acnes", SPIE Proceedings, SPIE-Int. Soc. Opt. Eng., 106-110, vol. 3247, Jan. 1998 (Abstract, 3 Pages).

Konig, et al. "Photodynamic Activity of Methylene Blue", Aktuelle Dermatol, vol. 19, 1993, pp. 195-198.

Konig, et al. "Photodynamically Induced Inactivation of Propionibacterium Acnes Using the Photosensitizer Methylene Blue and Red Light", Dermatologische Monatsschrift (Dermatol Monatsschr), vol. 178, Apr. 1992, pp. 297-300.

Kulkarni et al., "Effect of Experimental Temperature on the Permeation of Model Diffusants Across Porcine Buccal Mucosa" AAPS PharmSciTech. Jun. 2011; 12(2)579.

Lademann et al. "Nanoparticles—an efficient carrier for drug delivery into the hair follicles." *Eur J Pharm Biopharm*, 2007, 66:159-164.

Lazare, M. What are Cold Sores (Herpetic Lesions)?, http://www.drmarclazare.com/laser-treatments-for-coid-soresherpetic-lesions/, dated Jul. 8, 2014.

Le Guevel, et al. "Synthesis, Stabilization, and Functionalization of Silver Nanoplates for Biosensor Applications." J Phys Chem C, 113, 16380-16386. (Published Aug. 21, 2009).

Lewicka et al. "Nanorings and nanocrescents formed via shaped nanosphere lithography: a route toward large areas of infrared metamaterials." *IOP Publishing*, Nanotechnology 24: Feb. 28, 2013.

Lloyd, et al. "Selective Photothermolysis of the Sebaceous Glands for Acne Treatment", Lasers in Surgery and Medicine, vol. 31, 2002, pp. 115-120.

Mallon et al. "The quality of life in acne: a comparison with general medical conditions using generic questionnaires." *Br J Dermatol*, 1999, 140:672-676.

Maltzahn, Geoffrey von, et al., "Computationally Guided Photothermal Tumor Therapy Using Long-Circulating Gold Nanorod Antennas" Cancer Res 2009; 69: (9) Published online Apr. 14, 2009 as 10.11158/008-5472.CAN-08-4242.

Meidan, V.M. "Methods for quantifying intrafollicular drug delivery: a critical appraisal." *Expert Opin Drug Deliv*, 2010, 7:1095-1108.

Metraux, G. S. M. et al "Rapid Thermal Synthesis of Silver Nanoprisms with Chemically Tailorable Thickness." Advanced Materials, 2005, 17, No. 4, 412-415. (Published Feb. 23, 2005).

Mills, et al. "Ultraviolet Phototherapy and Photochemotherapy of Acne Vulgaris", Arch Dermatol, vol. 114, No. 2, Feb. 1978 (Abstract, 2 pages).

Mitragotri et al. "Synergistic effect of low-frequency ultrasound and sodium lauryl sulfate on transdermal transport." *J Pharm Sci*, 2000, 89:892-900.

Mortensen et al. "In vivo skin penetration of quantum dot nanoparticles in the murine model: the effect of UVR." *Nano Lett*, 2008, 8:2779-2787.

Mutzhas, et al. "A New Apparatus with High Radiation Energy Between 320-460 nm: Physical Description and Dermatological Applications", The Journal of Investigative Dermatology, vol. 76, No. 1, Jan. 1981, pp. 42-47.

Nanni, C.A. and Alster, T.S. (1997). "Optimizing treatment parameters for hair removal using a topical carbon-based solution and 1064-nm Q-switched neodymium: YAG laser energy." *Arch Dermatol*, 1997, 133:1546-1549.

New Attempts for Treatment by Electrical Incineration; Skin Surgery V. 11, No. 2, Nov. 2002 (Japanese translation).

Pento, et al. "Delta-Aminolevulinic Acid", Drugs of the Future, vol. 22, No. 1, 1997, pp. 11-17.

Phillips, et al. "Medical Progress: Recent Advances in Dermatology", New England Journal of Medicine, vol. 326, No. 3, Jan. 1992, pp. 1-9 (167-176).

Polat et al. "Ultrasound-mediated transdermal drug delivery: Mechanisms, scope, and emerging trends." *J Control Release*, 2011, 152:330-348.

Rallis, Tena M., "Low-Intensity Laser Therapy for Recurrent Herpes Labialis" The Journal of Investigative Dermatology, vol. 115, No. 1 Jul. 2000.

Rogers et al. "Hair removal using topical suspension-assisted Q-switched Nd: YAG and long-pulsed alexandrite lasers: A comparative study." *Dermatol Surg*, 1999, 25:844-844; discussion 848-850.

Rother K. "Diabetes Treatment—Bridging the Divide", N Engl J Med. 356:15, published Apr. 12, 2007.

Sakamoto et al. "Photodynamic therapy for acne vulgaris: A critical review from basics to clinical practice: Part 1, Acne Vulgaris: When and why consider photodynamic therapy?" *Journal of the American Academy of Dermatology*, 2010, 63:183-193.

Sakamoto et al. "Photodynamic therapy for acne vulgaris: A critical review from basics to clinical practice: Part II. Understanding parameters for acne treatment with photodynamic therapy." *Journal of the Academy of Dermatology*, 2010, 63:195-211.

Schultz, et al. "The Chemorheology of Poly(vinyl alcohol)-Borate Gels." Macromolecules, vol. 2, No. 3, 281-285. (Published May-Jun. 1969).

(56) References Cited

OTHER PUBLICATIONS

Sellheyer, K. "Basal cell carcinoma: cell of origin, cancer stem cell hypothesis and stem cell markers." *Br J Dermatol*, 2011, 164:696-711.
Sellheyer, K. (2007). "Mechanisms of laser hair removal: could persistent photoepilation induce vitiligo or defects in wound repair?" *Dermatol Surg*, 2007, 33:055-1065.
Shershen et al. "Temperature-Sensitive Polymer-Nanoshell Composites for Photothermally Modulated Drug Delivery" *Journal of Biomedical Materials Research*; vol. 51, Issue 3, pp. 293-298 (Jun. 28, 2000).
Vogt A. et al. "40 nm, but not 750 or 1,500 nm, Nanoparticles Enter Epidermal CD1a + Cells after Transcutaneous Application on Human Skin", Journal of Investigative Dermatology (2006) 126, 1316-1322, published Apr. 13, 2006.
Wainwright, Mark "Non-Porphyrin Photosensitizers in Biomedicine", Chemical Society Reviews, 1996, pp. 351-359.
West et al. "Applications of Nanotechnology to Biotechnology" *Current Opinion in Biotechnology* 2000, 11:215-217; Published Apr. 1, 2000.
Wong, S.Y., and Reiter, J.F. "Wounding mobilizes hair follicle stem cells to form tumors." *Proc Natl Acad Sci USA*, 2011, 108:4093-4098.
Xiong, et al. "Synthesis of silver nanoplates at high yields by slowing down the polyol reduction of silver nitrate with polyacrylamide." Journal of Materials Chemistry, 17, 2600-2602. (Published May 17, 2007).
Xue, et al. "pH-Switchable Silver Nanoprism Growth Pathways." Angew. Chem. Int. Ed., 46, 2036-2038. (Published Feb. 13, 2007).
Zhao, W., and Karp, J.M. "Tumour targeting: Nanoantennas heat up." *Nat Mater*, 2009, 8:453-454.
PCT/US2011/049464 International Search Report date Apr. 24, 2012.
Prosecution history (excluding references of record) of U.S. Appl. No. 13/789,575, including a 37 CFR 1.131 declaration over US Publication 2014/0005593 with U.S. Appl. No. 14/020,481, now U.S. Pat. No. 8,821,941, which shares common priority and/or an inventor with the present application. The 131 declaration is dated Dec. 31, 2014 (submission date to USPTO).
Prosecution history (excluding references of record) of U.S. Appl. No. 13/789,575, namely an Amendment and a Suggestion for Declaration of Interference (with Appendices) over US Publication 2014/0005593 with U.S. Appl. No. 14/020,481, now U.S. Pat. No. 8,821,941, which shares common priority and/or an inventor with the present application. The Amendment and Suggestion for Declaration of Interference (with Appendices) and related documentation is dated Jul. 28, 2015 (submission date to USPTO) (Part 1 of 5).
Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 2 of 5).
Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 3 of 5).
Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which common priority and/or an inventor with the present application. The Exhibits from a Suggestion for Declaration of Interference and related documentation is dated Jul. 28, 2015 (submission date to USPTO) (Part 4 of 5).
Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 5 of 5).
Prosecution history (excluding references of record) of U.S. Appl. No. 13/789,575, namely an amendment in view of a Suggestion for Declaration of Interference over US Publication 2014/0005593 with U.S. Appl. No. 14/020,481, now U.S. Pat. No. 8,821,941, which shares common priority and/or an inventor with the present application. The amendment and related documentation is dated Aug. 19, 2015 (submission date to USPTO).
Prosecution history (excluding references of record) of U.S. Appl. No. 13/789,575, namely an Advisory Action further to a Suggestion for Declaration of Interference over US Publication 2014/0005593 with U.S. Appl. No. 14/020,481, now U.S. Pat. No. 8,821,941, which shares common priority and/or an inventor with the present application. The Advisory Action and related documentation is dated Aug. 21, 2015 (mailing date from USPTO).
Patent Interference document—Declaration of Interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 1, dated Oct. 8, 2015).
Patent Interference document—Sienna notice of Real Party-In-Interest in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 5, dated Oct. 22, 2015).
Patent Interference document—Sienna notice of Related Proceedings in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 6, dated Oct. 22, 2015).
Patent Interference document—Sienna Clean Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 7, dated Oct. 22, 2015).
Patent Interference document—General Hospital Notice of Real Party-In-Interest in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 13, dated Oct. 22, 2015).
Patent Interference document—General Hospital Clean Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 14, dated Oct. 22, 2015).
Patent Interference document—General Hospital Notice of Related Proceedings in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 15, dated Oct. 22, 2015).
Patent Interference document—Sienna Annotated Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 19, dated Nov. 5, 2015).

(56) References Cited

OTHER PUBLICATIONS

Patent Interference document—General Hospital Annotated Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 20, dated Nov. 5, 2015).
Patent Interference document—Sienna Proposed Motions in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 21, dated Nov. 12, 2015).
Patent Interference document—General Hospital Proposed Motions in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 22, dated Nov. 12, 2015).
Patent Interference document—Order Expunging General Hospital papers in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 42, dated Nov. 13, 2015).
Patent Interference document—Order Authorizing Motions and Setting Times in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 46, dated Nov. 23, 2015).
Patent Interference document—Sienna Substantive Motion 1 for judgment that GHC's claims are unpatentable under 35 U.S.C. § 112, first paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 84, dated Feb. 10, 2016).
Patent Interference document—Sienna Substantive Motion 2 to be accorded benefit of the filing dates of Sienna U.S. Appl. No. 61/402,305; U.S. Appl. No. 61/422,612; and U.S. Appl. No. 61/516,308 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 85, dated Feb. 10, 2016).
Patent Interference document—First Declaration of Andrea Tao, Ph.D., in Support of Sienna Motions 1 and 2 in interference between Senior Party U.S. Pat. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1002, filed on Feb. 10, 2016).
Patent Interference document—General Hospital Motion 1 for Benefit of the Filing Date of U.S. Appl. No. 61/636,381 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 151, dated Feb. 10, 2016).
Patent Interference document—General Hospital Motion 2 for Finding of Lack of: (1) Written Description and (2) Enablement Under 35 U.S.C. § 112, First Paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 152, dated Feb. 10, 2016).
Patent Interference document—General Hospital Motion 3 to Vacate Accorded Benefit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 153, dated Feb. 10, 2016).
Patent Interference document—Second Declaration of Ivan J. Dmochowski in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2025, dated Feb. 10, 2016).
Patent Interference document—Order under 37 C.F.R. § 41.104(a) in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 159, dated Feb. 25, 2016).
Patent Interference document—Sienna Updated Real Party in Interest in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 160, dated Feb. 26, 2016).
Selections of prosecution history (excluding references of record) of U.S. Appl. No. 13/789,575, namely a Suggestion for Declaration of Interference (with Exhibits) over US Publication 2014/0005593 with U.S. Appl. No. 14/020,481, now U.S. Pat. No. 8,821,941, which shares common priority and/or an inventor with the present application. The Suggestion for Declaration of Interference (with related documentation) is dated Jul. 28, 2015 (submission date to USPTO).
Patent Interference document—General Hospital Priority Statement in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 155 [Not Publicly Available], dated Feb. 10, 2016) Paper File.
Patent Interference document—Sienna Priority Statement in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 86, dated Feb. 10, 2016): Paper File.
Patent Interference document—General Hospital Responsive Motion 4 to Add a Claim in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 162, dated Mar. 4, 2016).
Patent Interference document—General Hospital List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 163, dated Mar. 4, 2016).
Patent Interference document—Sienna List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 83, dated Feb. 10, 2016).
Curriculum Vitae of Andrea Tao, Ph.D. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1003, filed on Feb. 10, 2016).
U.S. Appl. No. 61/402,305 and Provisional Cover Sheet. Listed as exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1005 and 1029, filed on Feb. 10, 2016).

(56) References Cited

OTHER PUBLICATIONS

U.S. Appl. No. 61/422,612 and Provisional Cover Sheet. Listed as exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1006 and 1030, filed on Feb. 10, 2016).
U.S. Appl. No. 61/516,308 and Provisional Cover Sheet. Listed as exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1007 and 1031, filed on Feb. 10, 2016).
Appendix D of Jul. 28, 2015 General Hospital Corp. Section 202 Statement. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1011, filed on Feb. 10, 2016).
Jain, Prashant K. et al., J. Phys. Chem. B., 110:7238-7248 (2006). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1012, filed on Feb. 10, 2016).
Min, Younjin et al., Nature Materials, 7:527-538 (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1013, filed on Feb. 10, 2016).
Mastroianni, Alexander J. et al., J. Am. Chem. Soc. 131:8455-8459 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1014, filed on Feb. 10, 2016).
Zheng, Jiwen et al., Nano Letters, 6:105-1504 (2006). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1015, filed on Feb. 10, 2016).
Yan, Bo et al., ACS Nano, 3:1190-1202 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1016, filed on Feb. 10, 2016).
Shevchenko, Elena V. et al., Nature 439:55-59 (2006). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1017, filed on Feb. 10, 2016).
Kuzyk, Anton et al., Nature 483:311-314 (2012). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1018, filed on Feb. 10, 2016).
Pal, Suchetan et al., Angewandte Chemie Int'l Ed. 49:2700-2704 (2010). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1019, filed on Feb. 10, 2016).
Maye, Mathew M. et al., Nature Materials 8:388-391 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1020, filed on Feb. 10, 2016).
Feb. 24, 2014 Final Office Action in Sienna involved U.S. Appl. No. 14/020,481. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1021, filed on Feb. 10, 2016).
Mar. 27, 2014 Amendment in Sienna U.S. Appl. No. 14/020,599. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1022, filed on Feb. 10, 2016).
Jun. 24, 2014 Amendment in Sienna U.S. Appl. No. 14/020,481. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1023, filed on Feb. 10, 2016).
Sebacia Jun. 9, 2010 email and purchase order for NanoShells, from prosecution history (excluding copies of references of record) of U.S. Appl. No. 13/789,575, namely an exhibit from a Suggestion for Declaration of Interference over US Publication 2014/0005593 with U.S. Appl. No. 14/020,481, now U.S. Pat. No. 8,821,941. This Exhibit MGH 1054 is from a Suggestion for Declaration of Interference and related documentation dated Jul. 28, 2015 (submission date to USPTO). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1025, filed on Feb. 10, 2016).
Dmochowski Declaration—submitted by the General Hospital in Section 202 Statement from prosecution history (excluding references of record) of U.S. Appl. No. 13/789,575, namely an exhibit from a Suggestion for Declaration of Interference over US Publication 2014/0005593 with U.S. Appl. No. 14/020,481, now U.S. Pat. No. 8,821,941. This Exhibit MGH 1001 is from a Suggestion for Declaration of Interference and related documentation dated Jul. 28, 2015 (submission date to USPTO). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1026, filed on Feb. 10, 2016).
GHC Supplemental Amendment and Response to Non-final Office Action submitted by The General Hospital from prosecution history (excluding references of record) of U.S. Appl. No. 13/789,575 dated Jan. 1, 2015 (submission date to USPTO). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1027, filed on Feb. 10, 2016).
Detail of concentration calculation performed by Dr. Andrea Tao. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1028, filed on Feb. 10, 2016).
Jan. 2016 CV of Professor Ivan Dmochowski. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2027, filed on Feb. 10, 2016).

(56) References Cited

OTHER PUBLICATIONS

U.S. Appl. No. 61/636,381. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2031, filed on Feb. 10, 2016).

Sep. 9, 2013 Preliminary Amendment from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2032, filed on Feb. 10, 2016).

Feb. 12, 2014 Interview Summary and Supplemental Amendment from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2033, filed on Feb. 10, 2016).

Feb. 24, 2014 Final Office Action from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2034, filed on Feb. 10, 2016).

Jun. 24, 2014 Request for Continued Examination with Amendment and Interview Summary from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2035, filed on Feb. 10, 2016).

M. A. Garcia, Surface Plasmons in Metallic Nanoparticles: Fundamentals and Applications, 2011 J. Phys. D: Appl. Phys. 44 283001. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2036, filed on Feb. 10, 2016).

S. J. Oldenburg, J. B. Jackson, S. L. Westcott, and N. J. Halas, Infrared Extinction Properties of Gold Nanoshells, 75 Appl. Phys. Lett. 2897-2899 (1999). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2037, filed on Feb. 10, 2016).

X. Huang, I. El-Sayed, W. Qian, and M. El-Sayed, Cancer Cell Imaging and Photothermal Therapy in the Near-Infrared Region by Using Gold Nanorods, 128 J. Am. Chem. Soc., 2115-2120, 2006. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2038, filed on Feb. 10, 2016).

Todd James Harris Linkedin.com webpage. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2039, filed on Feb. 10, 2016).

Alice Ann Chen Kim Linkedin.com webpage. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2040, filed on Feb. 10, 2016).

X. Liu, M. Atwater, J. Wang, and Q. Huo, Extinction coefficient of gold nanoparticles with different sizes and different capping ligands, Colloids and Surfaces B: Biointerfaces 58 (2007) 3-7. Listed as Junior Party exhibit in interference between Senior Party US Pat. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2041, filed on Feb. 10, 2016).

David Paramelle, Anton Sadovoy, Sergey Gorelik, Paul Free, Jonathan Hobley, David G. Fernig, A Rapid Method to Estimate the Concentration of Citrate Capped Silver Nanoparticles from UV-Visible Light Spectra, 139, Analyst, 4855-4861 (2014). Listed as Junior Party exhibit in interference between Senior Party U.S. Pat. No. 8,821,941, which shares common priority, assignee, and inventorship with the present application, and Junior Party Serial No. 13/789,575 (U.S. Patent and Trademark Office, Patent Interference No. 106,037 (DK) Exhibit 2042, filed on Feb. 10, 2016).

David Paramelle, Anton Sadovoy, Sergey Gorelik, Paul Free, Jonathan Hobley, David G. Fernig, Supplementary Information a Rapid Method to Estimate the Concentration of Citrate Capped Silver Nanoparticles from UV-Visible Light Spectra, Electronic Supplementary Material (ESI) for Analyst . . . Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2043, filed on Feb. 10, 2016).

Heng Deng, Yanqi Zhong, Meihong Du, Qinjun Liu, Zhanming Fan, Fengying Dai, and Xin Zhang, Theranostic Self-Assembly Structure of Gold Nanoparticles for NIR Photothermal Therapy and X-Ray Computed Tomography Imaging, 4 Theranostics 904-918 (2014). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2044, filed on Feb. 10, 2016).

Silicon, From Wikipedia, the free encyclopedia, https://en.wikipedia.org/wiki/Silicon viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2045, filed on Feb. 10, 2016).

What Is the Most Conductive Element? Maximum Electrical Conductivity, http://chemistry.about.com/od/elements/f/What-ls-The-Most-Conductive-Element.htm viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2046, filed on Feb. 10, 2016).

Prashant K. Jain, Kyeong Seok Lee, Ivan H. El-Sayed, and Mostafa A. El-Sayed. Calculated absorption and scattering properties of gold nanoparticles of different size, shape, and composition: applications in biological imaging and biomedicine. 110 J. Phys. Chem. B, 7238-7248 (2006). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2047, filed on Feb. 10, 2016).

Gold Nanoparticles: Properties and Applications, http://www.sigmaaldrich.com/materials-science/nanomaterials/goldnanoparticles.html viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2048, filed on Feb. 10, 2016).

(56) References Cited

OTHER PUBLICATIONS

A. Smith, M. Mancini & S. Nie, Bioimaging: Second Window for In Vivo Imaging, 4 Nature Nanotechnology, 710-711 (2009). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2049, filed on Feb. 10, 2016).

Roger Grant and Clair Grant, Grant & Hackh's Chemical Dictionary, 374 (1987 5th ed.). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2050, filed on Feb. 10, 2016).

Hair follicle, From Wikipedia, the free encyclopedia, https://en.wikipedia.org/wiki/Hair_follicle viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2051, filed on Feb. 10, 2016).

Lumenis LightSheer ET brochure, http://partnerzone.lumenis.com/DesktopModules/Bring2mind/DMX/Download.aspx?Command=Core_Download&EntryId=3598&language=en-US&PortalId=0&TabId=386, viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2052, filed on Feb. 10, 2016).

Lumenis LightSheer ET webpage, http://www.lumenis.com/Solutions/Aesthetic/Products/LightSheer-ET, viewed Jan. 27, 2017 [sic] (2016). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2053, filed on Feb. 10, 2016).

NanoComposix Plasmonics and Nanophotonics, http://nanocomposix.com/pages/plasmonics-and-nanophotonics viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2054, filed on Feb. 10, 2016).

Conjugated Nanopartz™ Gold Nanoparticles, http://www.nanopartz.com/invitro_gold_nanoparticles.asp viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2055, filed on Feb. 10, 2016).

660 nm Resonant Gold Nanorods, http://nanocomposix.com/collections/goldnanorods/products/660-nm-resonant-gold-nanorods#example-coa viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2056, filed on Feb. 10, 2016).

Jian Hua Sun, Ming Yun Guan, Tong Ming Shang, Cui Ling Gao & Zheng Xu, Synthesis and Optical Properties of Triangular Gold Nanoplates with Controllable Edge Length, 53 Sci China Chem 9 2033-2038 (2010). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2057, filed on Feb. 10, 2016).

660 nm Resonant Gold Nanoshells, http://50.87.149.212/_Specification%20Sheets/Gold%20Nanoshells/660nm_Au_Nanoshells_PEG_NX_High_KJW2013_CoA.pdf?0311116 viewed Jan. 31, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2058, filed on Feb. 10, 2016).

Yugang Sun, Brian Mayers, and Younan Xia, Metal Nanostructures with Hollow Interiors, 15 Adv. Mater. 2003, 7±8, 641-646. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2059, filed on Feb. 10, 2016).

Ling Tong, Qingshan Wei, Alexander Wei, and Ji-Xin Cheng, Gold Nanorods as Contrast Agents for Biological Imaging: Optical Properties, Surface Conjugation, and Photothermal Effects, 85 Photochem Photobiol. 21-32 (2009). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2060, filed on Feb. 10, 2016).

Strem Gold Nanorods, 96/1530 Gold Nanorods Kit, http://www.strem.com/uploads/resources/documents/gold_nanorods_kit.pdf viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2061, filed on Feb. 10, 2016).

Hui Wang, Daniel W. Brandl, Fei Le, Peter Nordlander, and Naomi J. Halas, Nanorice: A Hybrid Plasmonic Nanostructure, 6 Nano Lett., 4, 827-832 (2006). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2062, filed on Feb. 10, 2016).

Nanopartz™ Gold Nanowires, http://www.nanopartz.com/bare_gold_nanowires.asp viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2063, filed on Feb. 10, 2016).

Priya Vasanthakumar, Optics and spectroscopy of gold nanowires, (Apr. 18, 2014) (unpublished Doctoral Thesis, Universite Paris-Sud, and Università di Pisa) https://tel.archives-ouvertes.fr/tel-00922344/document viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2064, filed on Feb. 10, 2016).

Gold Nanobipyramids, http://www.nanoseedz.com/Gold_Nanobipyramids_en.html viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2065, filed on Feb. 10, 2016).

Zhirui Guo, Xu Fan, Lianke Liva, Zhiping Bian, Chunrong Gu, Yu Zhang, Ning Gub, Di Yang, and Jinan Zhang, Achieving High-Purity Colloidal Gold Nanoprisms and Their Application as Biosensing Platforms, 348(1): J Colloid Interface Sci. 29-36, (2010). Listed as Junior Party exhibit in interference between Senior Party U.S. Pat. No. 8,821,941, which shares common priority, assignee,

(56) References Cited

OTHER PUBLICATIONS and inventorship with the present application, and Junior Party U.S. Appl. No. 13/789,575 (U.S. Patent and Trademark Office, Patent Interference No. 106,037 (DK) Exhibit 2066, filed on Feb. 10, 2016).

Gold Nanostars, http://www.nanoseedz.com/Au_nanostar.html viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2067, filed on Feb. 10, 2016).

NanoComposix Silver Nanoplates, http://nanocomposix.com/collections/silvernanoplates viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2068, filed on Feb. 10, 2016).

J. B. Jackson and N. J. Halas, Silver Nanoshells: Variations in Morphologies and Optical Properties, 105, J. Phys. Chem. B, 2743-2746 (2001). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2069, filed on Feb. 10, 2016).

Satarupa Pattanayak, Amiya Priyam, and Pradip Paik, Facile Tuning of Plasmon Bands in Hollow Silver Nanoshells Using Mild Reductant and Mild Stabilizer, 42, Dalton Trans., 10597-10607 (2013). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2070, filed on Feb. 10, 2016).

Nikhil R. Jana, Latha Gearheart and Catherine J. Murphy, Wet Chemical Synthesis of Silver Nanorods and Nanowires of Controllable Aspect Ratio, Chem. Commun., 617-618 (2001). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2071, filed on Feb. 10, 2016).

Benjamin J. Wiley, Yeechi Chen, Joseph M. McLellan, Yujie Xiong, Zhi-Yuan Li, David Ginger, and Younan Xia, Synthesis and Optical Properties of Silver Nanobars and Nanorice, 7, Nano Lett., 4, 1032-1036 (2007). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2072, filed on Feb. 10, 2016).

NanoComposix, Silver Nanoparticles: Optical Properties, http://nanocomposix.com/pages/silver-nanoparticles-optical-properties viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2073, filed on Feb. 10, 2016).

Nasser A. M. Barakat, Kee-Do Woo, Muzafar A. Kanjwal, Kyung Eun Choi, Myung Seob Khil, and Hak Yong Kim, Surface Plasmon Resonances, Optical Properties, and Electrical Conductivity Thermal Hystersis of Silver Nanofibers Produced by the Electrospinning Technique, 24 Langmuir 11982-11987 (2008). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2074, filed on Feb. 10, 2016).

Xiaoming Sun and Yadong Li, Cylindrical Silver Nanowires: Preparation, Structure, and Optical Properties, 17, Adv. Mater., 2626-2630 (2005). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2075, filed on Feb. 10, 2016).

Benjamin J. Wiley, Yujie Xiong, Zhi-Yuan Li, Yadong Yin, and Younan Xia, Right Bipyramids of Silver: A New Shape Derived from Single Twinned Seeds, 6, Nano Lett., 4, 765-768 (2006). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2076, filed on Feb. 10, 2016).

Gabriella S. Métraux and Chad A. Mirkin, Rapid Thermal Synthesis of Silver Nanoprisms with Chemically Tailorable Thickness, 17, Adv. Mater., 412-415 (2005). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2077, filed on Feb. 10, 2016).

Adianez Garcia-Leis, Jose Vicente Garcia-Ramos, and Santiago Sanchez-Cortes, Silver Nanostars with High SERS Performance, 117, J. Phys. Chem. C, 7791-7795 (2013). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2078, filed on Feb. 10, 2016).

Perry's Chemical Engineers' Handbook, (Robert H. Perry, Don Green, & James O. Maloney eds. 6th ed. 1984). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2079, filed on Feb. 10, 2016).

NanoComposix, 550 nm Resonant Silver Nanoplates, http://nanocomposix.com/collections/silver-nanoplates/products/550-nmresonant-silver-nanoplates viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2080, filed on Feb. 10, 2016).

NanoComposix, Certificate of Analysis Examples of Silica Shelled 70 nm Silver Nanospheres, http://50.87.149.212/_Specification%20Sheets/Silica-Coated%20Silver%20Spec%20Sheets/AG70-Si20-KJW1618A.pdf?0271031 viewed Jan. 27, 2017 [sic] (2016). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2081, filed on Feb. 10, 2016).

CRC Handbook of Chemistry and Physics, 88th Edition (David R. Lide, ed. 2007). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2083, filed on Feb. 10, 2016).

Cytodiagnostics webpage; http://www.cytodiagnostics.com/store/pc/Gold-Nanoparticle-Properties-d2.htm. Listed as Junior Party exhibit in interference between Senior Party U.S. Pat. No. 8,821,941, which shares common priority, assignee, and inventorship with the present application, and Junior Party U.S. Appl. No. 13/789,575 (U.S.

(56) References Cited

OTHER PUBLICATIONS

Patent and Trademark Office, Patent Interference No. 106,037 (DK) Exhibit 2085, filed on Feb. 10, 2016).

Jon A. Schwartz, Anil M. Shetty, Roger E. Price, R. Jason Stafford, James C. Wang, Rajesh K. Uthamanthil, Kevin Pham, Roger J. McNichols, Chris L. Coleman, and J. Donald Payne, Feasibility Study of Particle-Assisted Laser Ablation of Brain Tumors in Orthotopic Canine Model, 69 Cancer Res., 1659-1667 (2009). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2087, filed on Feb. 10, 2016).

Third Declaration of Ivan J. Dmochowski. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2089, filed on Mar. 4, 2016).

Todd J. Harris, Geoffrey von Maltzahn, Austin M. Derfus, Erkki Ruoslahti, and Sangeeta N. Bhatia, Proteolytic Actuation of Nanoparticle, 45 Angew. Chem. Int. Ed., 3161-3165 (2006). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2090, filed on Mar. 4, 2016).

Chung Hang J. Choi, Christopher A. Alabi, Paul Webster, and Mark E. Davis, Mechanism of active targeting in solid tumors with transferrin-containing gold nanoparticles, 107 PNAS, 1235-1240 (2010). Listed as Junior Party exhibit in interference between Senior Party U.S. Pat. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2091, filed on Mar. 4, 2016).

Liang Gao, Tegy J. Vadakkan, and Vengadesan Nammalvar, Nanoshells for In Vivo Imaging Using Two-photon Excitation Microscopy, 22 Nanotechnology, _ (2011). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2092, filed on Mar. 4, 2016).

Patent Interference document—Sienna Opposition 1 against Junior Party Motion 1 on Benefit of the Filing Date of U.S. Appl. No. 61/636,381 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 200, dated Apr. 8, 2016).

Patent Interference document—Sienna Opposition 2 against Junior Party Motion 2 on Written Description and Enablement Under 35 U.S.C. § 112, First Paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 220, dated Apr. 8, 2016).

Patent Interference document—Sienna Opposition 3 against Junior Party Motion 3 on Accorded Benefit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 201, dated Apr. 8, 2016).

Patent Interference document—Sienna Opposition 4 against Junior Party Motion 4 on Adding a Claim in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 221, dated Apr. 8, 2016).

Patent Interference document—Sienna List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 171, dated Apr. 8, 2016).

Patent Interference document—Second Declaration of Andrea Tao, Ph.D., in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1032, filed on Apr. 8, 2016).

Patent Interference document—First Declaration of Chad Mirkin, Ph.D. in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1034, filed on Apr. 8, 2016).

Patent Interference document—Curriculum Vitae of Chad Mirkin, Ph.D. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1035, filed on Feb. 10, 2016).

Patent Interference document—Summary report showing results of the computer simulation of the composition of 10×30 nm gold nanorods [895.1 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1046, filed on Apr. 8, 2016).

Patent Interference document—Summary report showing results of the computer simulation of the composition of 300 nm gold nanoshells [885.8 nm and 1281 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1047, filed on Apr. 8, 2016).

Patent Interference document—Summary report showing results of the computer simulation of the composition of 30×200 nm silver nanoplates [1059 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1048, filed on Apr. 8, 2016).

Patent Interference document—Summary report showing results of the computer simulation of the composition of 15×30 nm gold nanorods [901 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1049, filed on Apr. 8, 2016).

Gault, D.T. et al., "The Removal of Unwanted Hair Using a Ruby Laser," British J Plastic Surgery, 52:173-177 (1999). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1036, filed on Apr. 8, 2016).

Yoo, H. et al., NIH Public Access Author Manuscript, published in final edited form in Nano Letters, 9:3038-3041 (2009). Listed as exhibit in interference between Senior Party U.S. Pat. No. 8,821,941, which shares common priority, assignee, and inventorship with the present application, and Junior Party U.S. Appl. No. 13/789,575

(56) References Cited

OTHER PUBLICATIONS (U.S. Patent and Trademark Office, Patent Interference No. 106,037 (DK) Exhibit 1038, filed on Apr. 8, 2016).

Skrabalak, S.E. et al., Nature Protocols, 2:2182-2190 (2007). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1039, filed on Apr. 8, 2016).

Millstone, J.E. et al., J Amer. Chem. Society, 127:5312-5313 (2005). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1040, filed on Apr. 8, 2016).

Kim, F. et al., J Amer. Chem. Society, 124:14316-14317 (2002). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1041, filed on Apr. 8, 2016).

Rodriguez-Lorenzo, L., J Physical Chem., 114:7336-7340 (2010),. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1042, filed on Apr. 8, 2016).

Von Maltzahn, G. et al., Cancer Research, 69:3892-3900 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1043, filed on Apr. 8, 2016).

Bost, W. et al., IFMBE Proc., 25/II, 529-532 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1044, filed on Apr. 8, 2016).

Chang, W. et al., PNAS, 107:2781-2786 (2010). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1045, filed on Apr. 8, 2016).

Jin, Rongchao et al., Science, 294:1901-1903 (2001). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1050, filed on Apr. 8, 2016).

Nikoobakht, B. et al., Chem. Mater., 15:1957-1962 (2003). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1051, filed on Apr. 8, 2016).

Nanopartz Application Note—Nsol Gold Nanorods for use in organic solvents (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1052, filed on Apr. 8, 2016).

Nanopartz Product Profile—Nsol gold nanorods (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1053, filed on Apr. 8, 2016).

Nanopartz Product Profile—Gold Nanorodz (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1054, filed on Apr. 8, 2016).

Nanopartz Product Profile—Ntracker (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1055, filed on Apr. 8, 2016).

Nanopartz Technical Note—Photothermal Characteristics of Gold Nanorods—TN802 (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1056, filed on Apr. 8, 2016).

Jin, Rongchao et al., Nature, 425:487-490 (Oct. 2, 2003). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1059, filed on Apr. 8, 2016).

Patent Interference document—Junior Party Opposition 1 against Sienna Motion 1 for judgment that GHC's claims are unpatentable under 35 U.S.C. § 112, first paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 222, dated Feb. 10, 2016).

Patent Interference document—Junior Party Opposition 2 against Sienna Substantive Motion 2 to be accorded benefit of the filing dates of Sienna U.S. Appl. No. 61/402,305; U.S. Appl. No. 61/422,612; and U.S. Appl. No. 61/516,308 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 223, dated Feb. 10, 2016).

Patent Interference document—Junior Party List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 224, dated Apr. 8, 2016).

Patent Interference document—Fourth Declaration of Ivan J. Dmochowski, Ph. D.—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2093, filed on Apr. 8, 2016).

Patent Interference document—Ms. Pulsipher's Notebook Pages (dated Mar. 22, 2016 to Apr. 1, 2016)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2095, filed on Apr. 8, 2016).

Patent Interference document—Transcript from the Mar. 23, 2016 Cross-Examination of Dr. Andrea Tao—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2114, filed on Apr. 8, 2016).

Certificates of Analysis from Nanospectra from Dec. 2010 and 2016—Listed as Junior Party exhibit in interference between Senior Party U.S. Pat. No. 8,821,941, which shares common priority, assignee, and inventorship with the present application, and Junior

(56) References Cited

OTHER PUBLICATIONS

Party U.S. Appl. No. 13/789,575 (U.S. Patent and Trademark Office, Patent Interference No. 106,037 (DK) Exhibit 2094, filed on Apr. 8, 2016).
Leon R. Hirsch, R. Jason Stafford, J. A. Bankson, Scott R. Sershen, B. Rivera, R. E. Price, John D. Hazle, Naomi J. Halas, and Jennifer L. West, Nanoshellmediated near-infrared thermal therapy of tumors under magnetic resonance guidance, PNAS 2003 100 (23) 13549-13554 (2003)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2098, filed on Apr. 8, 2016).
Sienna Labs, "Management", http://www.siennalabs.com/management/ (viewed on Apr. 7, 2015)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2111, filed on Apr. 8, 2016).
Todd J. Harris, Geoffrey von Maltzahn, and Sangeeta N. Bhatia, Multifunctional Nanoparticles for Cancer Therapy, in Nanotechnology for Cancer Therapy, 59-75 (Mansoor M. Amiji ed., 2006)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2113, filed on Apr. 8, 2016).
Takumi Hawa, Brian Henz and Michael Zachariah (2007). Computer Simulation of Nanoparticle Aggregate Fracture. MRS Proceedings, 1056, 1056-HH08-45 doi:10.1557/PROC-1056-HH08-45.—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2117, filed on Apr. 8, 2016).
Geoffrey von Maltzahn, Todd J Harris, Ji-Ho Park, Dal-Hee Min, Alexander J Schmidt, Michael J. Sailor, and Sangeeta N. Bhatia, Nanoparticle Self-Assembly Gated by Logical Proteolytic Triggers, 129(19), J Am Chem Soc., 6064-6065, 6065 (2007)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2118, filed on Apr. 8, 2016).
Piotr Grodzinski, nanoUtah slides, Oct. 2007—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2120, filed on Apr. 8, 2016).
Nikhil R. Jana, Shape Effect in Nanoparticle Self-Assembly, Angew. Chem. Int. Ed. 43, 1536-1540 (2004).—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2122, filed on Apr. 8, 2016).
Patent Interference document—Sienna Reply 1 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 230, dated May 20, 2016).
Patent Interference document—Sienna Reply 2 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 231, dated May 20, 2016).
Patent Interference document—Sienna List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 232, dated May 20, 2016).
Patent Interference document—Transcript from the May 2, 2016 Cross-Examination of Dr. Chad Mirkin—Listed as Senior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1061, filed on May 20, 2016).
Patent Interference document—Junior Party Reply 1 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 247, dated May 20, 2016).
Patent Interference document—Junior Party Reply 2 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 248, dated May 20, 2016).
Patent Interference document—Junior Party Reply 3 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 249, dated May 20, 2016).
Patent Interference document—Junior Party Reply 4 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 246, dated May 20, 2016).
Patent Interference document—Junior Party List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 245, dated May 20, 2016).
Kelly Y. Kim, MA, Nanotechnology platforms and physiological challenges for cancer therapeutics, Nanomedicine: Nanotechnology, Biology, and Medicine 3 (2007) 103-110—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2124 filed on May 20, 2016).
Sandani Samarajeewa, et al., Programmed hydrolysis of nanoassemblies by electrostatic interaction-mediated enzymatic-degradation, Chem Commun (Camb). Jan. 28, 2014 ; 50(8): 968-970—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2125 filed on May 20, 2016).
Jeffery G. Sheldon, Patent Applications for the Chemical Invention, in How to Write a Patent Application, PLI, 2014 (Chapter 13)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2130 filed on May 20, 2016).
Comsol AB, Finite Element Mesh Refinement, www.comsol.com/multiphysics/mesh-refinement, viewed May 18, 2016—Listed as

(56) References Cited

OTHER PUBLICATIONS

Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2131 filed on May 20, 2016).
Comsol Multiphysics User's Guide version 4.3, (2012) (Excerpts of the 1,292 page document, including title, table of contents, and sections cited by Junior Party in Reply 2 and Reply 3)—Full 1,292 page document listed as Junior Party exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK), submitted by Junior Party as Exhibit 2132A and 2132B filed on May 20, 2016).
Patent Interference document—Decision on Motions in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 315, dated Aug. 9, 2016).
Patent Interference document—Judgment in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 316, dated Aug. 9, 2016).
Patent Interference Appeal document—Appeal Brief by Appellant Junior Party—Appeal to the Judgment in Patent Interference No. 106,037 (DK) between Senior Party U.S. Pat. No. 8,821,941, which shares common priority, assignee, and inventorship with the present application, and Junior Party U.S. Appl. No. 13/789,575 (U.S. Court of Appeals for the Federal Circuit No. 2017-1012, Paper 17, dated Jan 13, 2017 (98 pages)).
Patent Interference Appeal document—Appeal Brief by Appellee Senior Party—Re: Patent Interference No. 106,037 (DK) between Senior Party U.S. Pat. No. 8,821,941, which shares common priority, assignee, and inventorship with the present application, and Junior Party U.S. Appl. No. 13/789,575 (U.S. Court of Appeals for the Federal Circuit No. 2017-1012, Paper 20, dated Feb. 22, 2017 (73 pages)).
Patent Interference Appeal document—Judgment and Opinion by United States Court of Appeals for the Federal Circuit Case 17/1012—Re: Patent Interference No. 106,037 (DK) between Senior Party U.S. Pat. No. 8,821,941, which shares common priority, assignee, and inventorship with the present application, and Junior Party U.S. Appl. No. 13/789,575 (U.S. Court of Appeals for the Federal Circuit No. 2017-1012, Paper 47 dated May 4, 2018 (13 pages)).
Patent Interference document—Decision on Motions in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 323, dated Nov. 20, 2018).
Patent Interference document—Judgment in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 324, dated Nov. 20, 2018).
Sebacia, Inc. Notice of Opposition to European Patent No. EP2608762, which shares common priority and/or an inventor with the present application, filed on Apr. 18, 2018.
Sebacia EPO Exhibit D1—Leon R. Hirsch, R. Jason Stafford, J. A. Bankson, Scott R. Sershen, B. Rivera, R. E. Price, John D. Hazle, Naomi J. Halas, and Jennifer L. West, Nanoshellmediated near-infrared thermal therapy of tumors under magnetic resonance guidance, PNAS 2003 100 (23) 13549-13554 (2003)—(EPO Opposition Exhibit filed on Apr. 18, 2018).
Sebacia EPO Exhibit D2—Emily S. Day, Patrick A. Thompson, Linna Zhang, Nastassja A. Lewinski, Nabil Ahmed, Rebekah A. Drezek, Susan M. Blaney, Jennifer L. West, "Nanoshell-mediated photothermal therapy improves survival in a murine glioma model" Journal of Neuro-Oncology, vol. 104, Nov. 26, 2010 (EPO Opposition Exhibit filed on Apr. 18, 2018).
Sebacia EPO Exhibit D3—Andre M. Gobin, James J. Moon, and Jennifer L. West, "EphrinA1-targeted nanoshells for photothermal ablation of prostate cancer cells" International Journal of Nanomedicine, vol. 3, No. 3 pp. 351-358 (2008) (EPO Opposition Exhibit filed on Apr. 18, 2018).
Sebacia EPO Exhibit D4—U.S. Pat. No. 5,226,907 (EPO Opposition Exhibit filed on Apr. 18, 2018).
Sebacia EPO Exhibit D5—Amanda R. Lowery, Andre M Gobin, Emily S. Day, Naomi J. Halas, Jennifer L. West, "Immunonanoshells for targeted photothermal ablation of tumor cells" International Journal of Nanomedicine, vol. 1, No. 2, (2006) 149-154 (EPO Opposition Exhibit filed on Apr. 18, 2018).
Sebacia EPO Exhibit D6—US Publication 2002/0187347 (EPO Opposition Exhibit filed on Apr. 18, 2018).
Sebacia EPO Exhibit D7—U.S. Pat. No. 6,050,990 (EPO Opposition Exhibit filed on Apr. 18, 2018).
Sebacia EPO Exhibit D8—Sujit Kumar Ghosh, Tarasankar Pal, "Interparticle Coupling Effect on the Surface Plasmon Resonance of Gold Nanoparticles: From Theory to Applications" Chemical Reviews, vol. 107, No. 11, 4797-4862 (Nov. 14, 2007) (EPO Opposition Exhibit filed on Apr. 18, 2018).
Sebacia EPO Exhibit D9—Nanopartz, "Ntracker" Nov. 2, 2009, "Ntracker" Website Disclosure, taken from the "WayBackMachine" Archive dated Feb. 11, 2009 [https://web.archive.org/web/20090211032736/http:/ fnanopartz.com: 80/Ntracker.htm] (EPO Opposition Exhibit filed on Apr. 18, 2018).
Sebacia EPO Exhibit D10—US Publication 2010/0016783 (EPO Opposition Exhibit filed on Apr. 18, 2018).
Sebacia EPO Exhibit D11—Kobayashi, Yoshio et al., "Silica coating of silver nanoparticles using a modified Stober method" Journal of Colloid and Interface Science, vol. 283, 2005 (EPO Opposition Exhibit filed on Apr. 18, 2018).
Sebacia EPO Exhibit D126—Wiley, Benjamin J. et al., "Maneuvering the Surface Plasmon Resonance of Silver Nanostructures through Shape-Controlled Synthesis" Journal of Physical Chemistry B, vol. 110, No. 32, 2006 (EPO Opposition Exhibit filed on Apr. 18, 2018).
Sebacia EPO Exhibit D13—U.S. Pat. No. 5,817,089 (EPO Opposition Exhibit filed on Apr. 18, 2018).
Sebacia EPO Exhibit D14—Smith, Andrew M. et al., "Second window for in vivo imaging" Nature Nanotechnology, vol. 4, No. 11, 2009 (EPO Opposition Exhibit filed on Apr. 18, 2018).
Opposition documentation to European Patent No. EP2608762, which shares common priority and/or an inventor with the present application, filed Jul. 23 to Jul. 30, 2019. (449 pages).
Sebacia, Inc. Notice of Opposition to European Patent No. EP3222266, which shares common priority and/or an inventor with the present application, (36 pages) filed on Jan. 18, 2019.
Sienna Biopharmaceuticals, Inc., Petition for Inter Partes Review filed Oct. 7, 2016 in Re U.S. Pat. No. 6,530,944; IPR2017-00045; Paper 1, 62 pages.
Sienna Biopharmaceuticals, Inc., Power of Attorney in Inter Partes Review filed Oct. 7, 2016 in Re U.S. Pat. No. 6,530,944; IPR2017-00045; Paper 2, 2 pages.
Sienna IPR Exhibit 1001—U.S. Pat. No. 6,530,944 (filed Oct. 7, 2016 in Re IPR2017-00045).
Sienna IPR Exhibit 1002—U.S. Pat. No. 5,226,907 (filed Oct. 7, 2016 in Re IPR2017-00045).
Sienna IPR Exhibit 1003—U.S. Pat. No. 5,817,089 (filed Oct. 7, 2016 in Re IPR2017-00045).
Sienna IPR Exhibit 1004—U.S. Pat. No. 6,183,773 (filed Oct. 7, 2016 in Re IPR2017-00045).
Sienna IPR Exhibit 1005—U.S. Pat. No. 6,165,440 (filed Oct. 7, 2016 in Re IPR2017-00045).
Sienna IPR Exhibit 1006—Declaration of Kenneth S. Suslick, Ph.D. (filed Oct. 7, 2016 in Re IPR2017-00045).

(56) References Cited

OTHER PUBLICATIONS

Sienna IPR Exhibit 1007—Curriculum Vitae of Kenneth S. Suslick, Ph.D. (filed Oct. 7, 2016 in Re IPR2017-00045).
Sienna IPR Exhibit 1008—Patent Prosecution History of U.S. Pat. No. 6,530,944 (filed Oct. 7, 2016 in Re IPR2017-00045).
Sienna IPR Exhibit 1009—Merriam-Webster's Collegiate Dictionary, Eleventh Edition, 2012 (filed Oct. 7, 2016 in Re IPR2017-00045).
Sienna IPR Exhibit 1010—"40 nm, but not 750 or 1,500 nm, Nanoparticles Enter Epidermal CD1a+ Cells after Transcutaneous Application on Human Skin," A. Vogt et al., Journal of Investigative Dermatology, vol. 126 (2006) (Vogt) (filed Oct. 7, 2016 in Re IPR2017-00045).
Board Notice of Accord Filing Date in Inter Partes Review IPR2017-00045; Paper 3 (dated Oct. 18, 2016).
William Marsh Rice University, Mandatory Notice in Inter Partes Review in Re U.S. Pat. No. 6,530,944; IPR2017-00045; Paper 4 (filed Nov. 21, 2016).
William Marsh Rice University, Power of Attorney in Inter Partes Review in Re U.S. Pat. No. 6,530,944; IPR2017-00045; Paper 5 (filed Nov. 21, 2016).
William Marsh Rice University, Patent Owner Preliminary Response to Petition for Inter Partes Review in Re U.S. Pat. No. 6,530,944; IPR2017-00045; Paper 6 (filed Jan. 18, 2017).
Rice IPR Exhibit 2001—Gabor L. Hornyak, Joydeep Dutta, H.F. Tibbals, Anil Rao, Introduction to Nanoscience, 274-284 (2008) (filed Jan. 18, 2017 in Re IPR2017-00045).
Rice IPR Exhibit 2002—G. Baffou, R. Quidant, and C. Girard, Heat generation in plasmonic nanostructures: Influence of morphology, Applied Physics Letters 94, 153109 (2009) (filed Jan. 18, 2017 in Re IPR2017-00045).
Rice IPR Exhibit 2003—Silver Nanomaterials: Properties & Applications http://www.sigmaaldrich.com/technicaldocuments/articles/technology-spotlights/silvernanomaterials.html (dated Jan. 18, 2017) (filed Jan. 18, 2017 in Re IPR2017-00045).
Rice IPR Exhibit 2004—Gold Nanoparticles: Properties and Applications http://www.sigmaaldrich.com/technicaldocuments/articles/materials-science/nanomaterials/goldnanoparticles.html#opt (dated Jan. 18, 2017) (filed Jan. 18, 2017 in Re IPR2017-00045).
Rice IPR Exhibit 2005—H. E. Bennett and J. L. Stanford, Structure-Related Optical Characteristics of Thin Metallic Films in the Visible and Ultraviolet, Journal of Research of the National Bureau of Standards—A. Physics and Chemistry, vol. 80A, No. 4, Jul.-Aug. 1976 (filed Jan. 18, 2017 in Re IPR2017-00045).
Rice IPR Exhibit 2006—U.S. Pat. No. 6,344, 272 (filed Jan. 18, 2017 in Re IPR2017-00045).
Final Written Decision of Inter Partes Review; in Re U.S. Pat. No. 6,530,944; Paper 52, 61 pages (dated Apr. 5, 2018 in Re IPR2017-00045).
Sienna Biopharmaceuticals, Inc., Petition for Inter Partes Review filed Oct. 7, 2016 in Re U.S. Pat. No. 6,685,730; IPR2017-00046; Paper 1, 55 pages.
Sienna Biopharmaceuticals, Inc., Power of Attorney in Inter Partes Review filed Oct. 7, 2016 in Re U.S. Pat. No. 6,685,730; IPR2017-00046; Paper 2, 2 pages.
Sienna IPR Exhibit 1001—U.S. Pat. No. 6,685,730 (filed Oct. 7, 2016 in Re IPR2017-00046).
Sienna IPR Exhibit 1002—U.S. Pat. No. 6,183,773 (filed Oct. 7, 2016 in Re IPR2017-00046).
Sienna IPR Exhibit 1003—U.S. Pat. No. 5,810,801 (filed Oct. 7, 2016 in Re IPR2017-00046).
Sienna IPR Exhibit 1004—U.S. Pat. No. 5,226,907 (filed Oct. 7, 2016 in Re IPR2017-00046).
Sienna IPR Exhibit 1005—U.S. Pat. No. 5,817,089 (filed Oct. 7, 2016 in Re IPR2017-00046).
Sienna IPR Exhibit 1006—U.S. Pat. No. 6,050,990 (filed Oct. 7, 2016 in Re IPR2017-00046).
Sienna IPR Exhibit 1007—Declaration of Kenneth S. Suslick, Ph.D. (filed Oct. 7, 2016 in Re IPR2017-00046).
Sienna IPR Exhibit 1008—Curriculum Vitae of Kenneth S. Suslick, Ph.D. (filed Oct. 7, 2016 in Re IPR2017-00046).
Sienna IPR Exhibit 1009—Patent Prosecution History of U.S. Pat. No. 6,685,730 (filed Oct. 7, 2016 in Re IPR2017-00046).
Sienna IPR Exhibit 1010—Merriam-Webster's Collegiate Dictionary, Eleventh Edition, 2012 (filed Oct. 7, 2016 in Re IPR2017-00046).
Sienna IPR Exhibit 1011—"40 nm, but not 750 or 1,500 nm, Nanoparticles Enter Epidermal CD1a+ Cells after Transcutaneous Application on Human Skin," A. Vogt et al., Journal of Investigative Dermatology, vol. 126 (2006) (Vogt) (filed Oct. 7, 2016 in Re IPR2017-00046).
Board Notice of Accord Filing Date in Inter Partes Review IPR2017-00046; Paper 3 (dated Oct 27, 2016).
William Marsh Rice University, Mandatory Notice in Inter Partes Review in Re U.S. Pat. No. 6,685,730; IPR2017-00046; Paper 4 (filed Nov 21, 2016).
William Marsh Rice University, Power of Attorney in Inter Partes Review in Re U.S. Pat. No. 6,685,730; IPR2017-00046; Paper 5 (filed Nov 21, 2016).
William Marsh Rice University, Patent Owner's Preliminary Response to Petition for Inter Partes Review in Re U.S. Pat. No. 6,685,730; IPR2017-00046; Paper 6 (filed Jan. 27, 2017).
Rice IPR Exhibit 2001—USPTO Ex Parte Reexamination in Re U.S. Pat. No. 6,685,730 (filed Jan. 27, 2017 in Re IPR2017-00046).
Final Written Decision of Inter Partes Review; in Re U.S. Pat. No. 6,685,730; Paper 18, 75 pages (dated Apr. 18, 2018 in Re IPR2017-00046).

FIG. 1
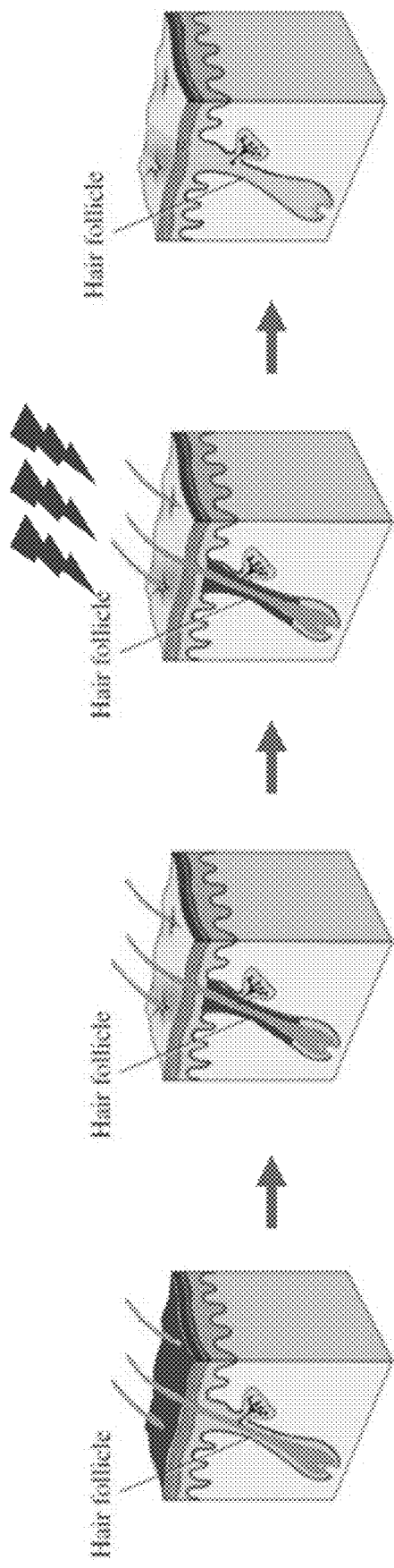
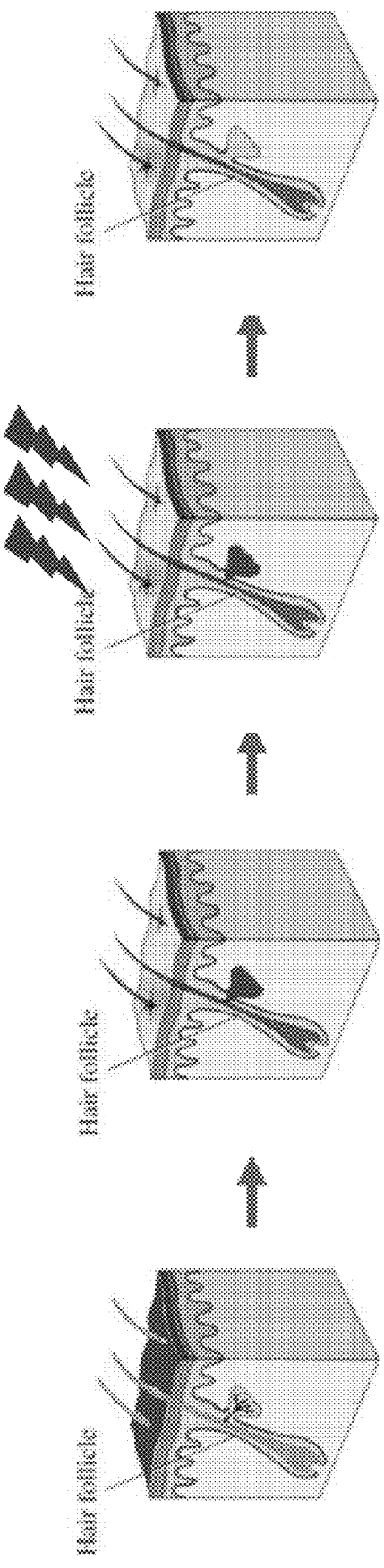

FIG. 17

| | % of total skin cross-section w/ particles at 500 μm | Max Depth | Mechanism |
|---|---|---|---|
| Vibraderm (Vib) 80hz longitudinal vibration | 4% | 1000 microns | Mechanical delivery |
| Acoustic horn / Sonotrode 30khz ultrasound pulsed and surface localized energy | 12% | 1500 microns | Localized cavitation from sonotrode |
| Flat transducer 40Khz ultrasound non-pulsed, non-localized energy | Variable 4-12% | 1000 microns | Unfocused cavitation from flat transducer |

210 — Vibraderm
220 — Acoustic horn / Sonotrode
230 — Flat transducer

FIG. 18
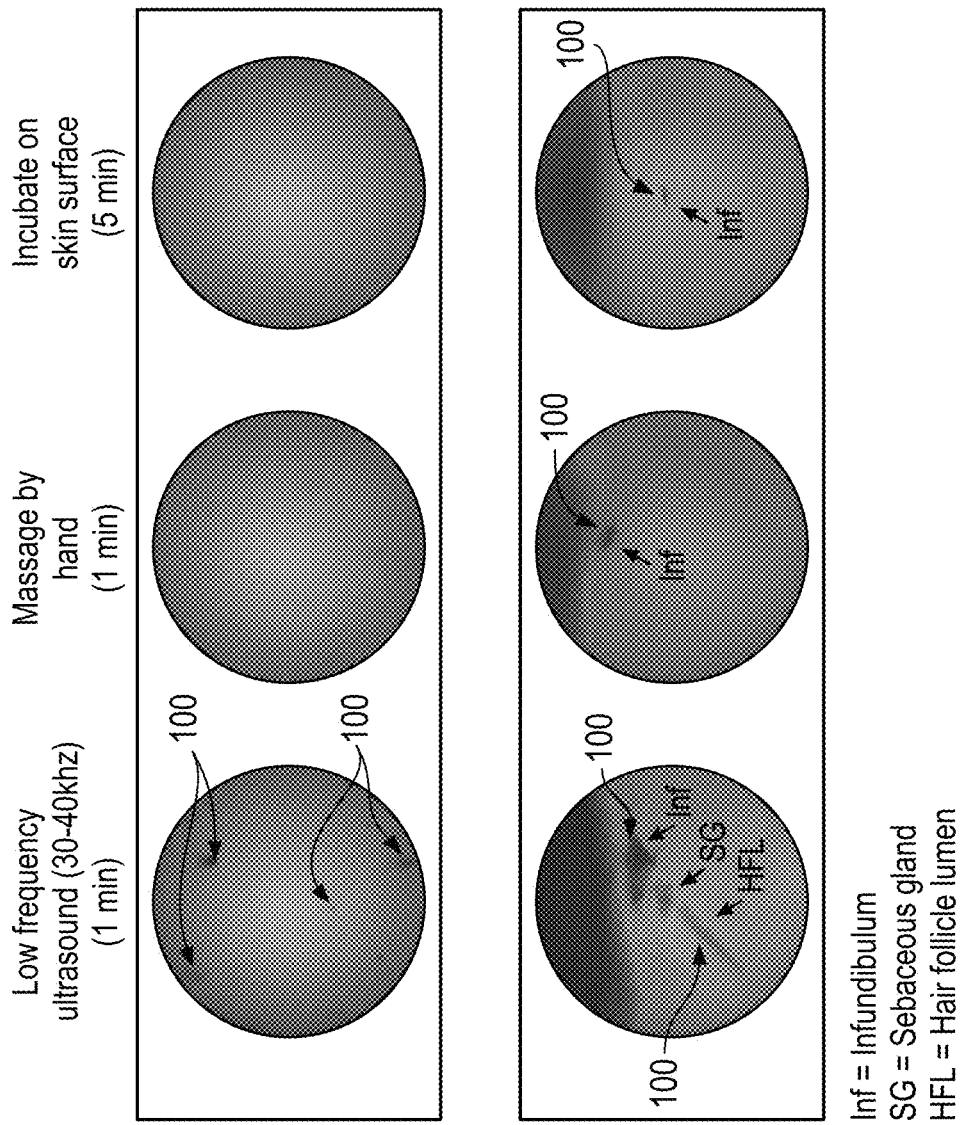
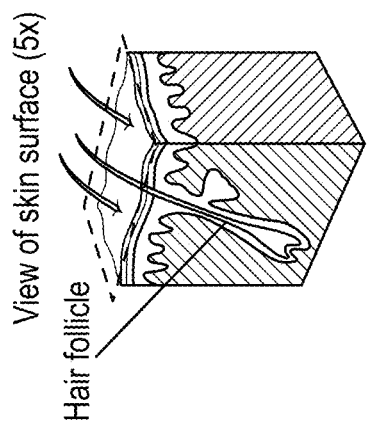
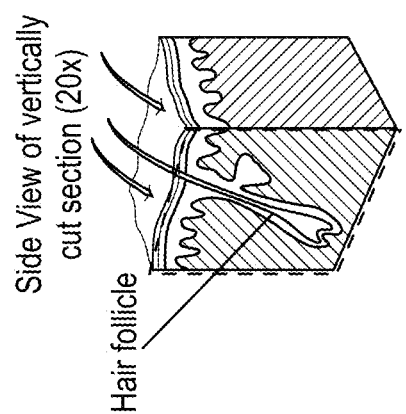

DELIVERY OF NANOPARTICLES

INCORPORATION BY REFERENCE

This application is a continuation of U.S. patent application Ser. No. 15/432,073 filed Feb. 14, 2017, now U.S. Pat. No. 10,537,640, U.S. patent application Ser. No. 14/321,509 filed Jul. 1, 2014, now U.S. Pat. No. 9,572,880, which is a continuation in part of U.S. patent application Ser. No. 14/020,423 filed Sep. 6, 2013, now U.S. Pat. No. 8,834,933, which is a continuation of U.S. patent application Ser. No. 13/219,514 filed Aug. 26, 2011, now U.S. Pat. No. 9,061,056, which claims the benefit of priority of U.S. Provisional Application Nos. 61/402,305 filed Aug. 27, 2010; 61/422,612 filed Dec. 13, 2010, and 61/516,308 filed Apr. 1, 2011; each of which is hereby incorporated by reference in its entirety. This application also claims the benefit of priority of U.S. Provisional Application No. 61/870,103 filed Aug. 26, 2013. Any and all applications for which a foreign or domestic priority claim is identified in the Application Data Sheet as filed with the present application are hereby incorporated by reference under 37 CFR 1.57.

PARTIES OF JOINT RESEARCH AGREEMENT

The invention described herein was created subject to a Joint Research Agreement between Sienna Labs, Inc. and Nanocomposix, Inc.

BACKGROUND

Field of the Invention

The field of the invention comprises nanoparticles and/or photoactive compounds for use in cosmetic, diagnostic and/or therapeutic procedures, including ultrasonic delivery systems and methods for delivering the particles and/or compounds to a target tissue. Ultrasound, according to several embodiments, is low frequency ultrasound delivered by, for example, a transducer or sonotrode. In several embodiments, the invention relates to using laser or light energy combined with nanoparticles and/or photoactive compounds to modify, smooth, and/or resurface the skin (including tissue under the skin surface) of humans.

Description of the Related Art

Laser treatments of the skin have been highly touted for therapeutic and cosmetic utility. Therapeutically, potential uses for laser skin therapy include laser ablation of cancerous cells in cancer patients and laser ablation of damaged tissue in burn victims. Cosmetic applications for laser skin therapy are much more numerous, and include hair removal/reduction, treatment of dyschromia, shrinking of the skin following operations such as liposuction, acne treatment, chemical or physical abrasion of unwanted markings on the skin, surgical treatments including nose reduction and face- and neck-lifts, and other aesthetic skin remodeling purposes.

SUMMARY

In several embodiments, the invention relates to using laser or light energy combined with nanoparticles and/or photoactive compounds to treat the skin (including tissue under the skin surface) using ultrasound to facilitate the delivery of the nanoparticles and/or photoactive compounds. In some embodiments, the invention is able to modify, smooth, and/or resurface the skin (including tissue under the skin surface) of humans. Several embodiments of the present invention also relate to methods for focusing electromagnetic energy with particles and/or photoactive compounds to selectively heat target regions of skin with a discrete, often minute, size and shape for the treatment of acne, especially acne scars, while not damaging surrounding skin tissue. In some embodiments, the particles can be microparticles and/or nanoparticles.

Also, provided herein, in several embodiments, are compositions and methods useful in the targeted thermomodulation of target cell populations and target tissues, for the purposes of cosmetic treatments and the treatment and prevention of chronic and acute diseases and disorders and enhanced delivery systems and methods (e.g., using ultrasound) for delivering the particles and/or compounds to a target tissue.

In various embodiments, a method of delivering a composition to a target tissue under a skin surface with a delivery device includes applying a composition to a skin surface, and distributing the composition from the skin surface to a target tissue under the skin surface with a delivery device. In one embodiment, the delivery device is an ultrasound device. In one embodiment, the composition comprises a plurality of unassembled plasmonic nanoparticles. In one embodiment, the unassembled plasmonic nanoparticles comprise a conductive metal portion. In one embodiment, the conductive metal portion comprises at least one of gold or silver. In one embodiment, the unassembled plasmonic nanoparticles have a size in a range of 10 nm to 300 nm. In one embodiment, the unassembled plasmonic nanoparticles comprise a coating that coats the conductive metal portion, wherein the coating facilitates selective removal from the skin surface. In one embodiment, the coating comprises at least one of silica or polyethylene glycol (PEG). In one embodiment, the unassembled plasmonic nanoparticles have a concentration of $10^9$ to $10^{23}$ particles per ml of the composition, wherein the concentration is sufficient to, after exposure to irradiation, induce thermal damage in a sebaceous gland. In one embodiment the method includes selectively removing the composition from the skin surface, while leaving the composition localized within the sebaceous gland. In one embodiment the method includes irradiating the composition with an infrared light source thereby inducing a plurality of surface plasmons in the unassembled plasmonic nanoparticles. In one embodiment, the plurality of surface plasmons generates localized heat in the target tissue. In one embodiment, the mechanical vibration device is a low frequency ultrasound device. In one embodiment, the method includes pre-treating the skin surface prior to irradiating the composition, wherein pre-treating the skin surface comprises hair removal. In one embodiment, the unassembled plasmonic nanoparticles comprise an optical density of 10 O.D. to 5,000 O.D. at an infrared light range. In one embodiment, the unassembled plasmonic nanoparticles comprise a solid, conducting silver core and a silica coating. In one embodiment, the conductive metal portion is a silver nanoplate, and the coating is less conductive than the conductive metal portion. In one embodiment, the conductive metal portion is a nanoplate, and the nanoplate has a peak absorption wavelength in a range of 750 nm to 1200 nm. In one embodiment, the coating comprises silica, wherein generation of localized heat is sufficient to affect at least one of a sebocyte and sebum.

In various embodiments, a method of delivering a composition to a sebaceous gland includes topically applying a solution of unassembled plasmonic nanoparticles to a skin surface, and targeting a sebaceous gland by redistributing the solution of unassembled plasmonic nanoparticles from the skin surface to the sebaceous gland with a delivery device.

In one embodiment, the delivery device is a mechanical vibration device, wherein the mechanical vibration device comprises at least one of the group consisting of an ultrasound device and a massage device. In one embodiment, the unassembled plasmonic nanoparticles have a dimension in a range of 10 nm to 300 nm. In one embodiment, the unassembled plasmonic nanoparticles have a concentration of $10^9$ to $10^{23}$ particles per ml of the solution. In one embodiment, the unassembled plasmonic nanoparticles comprise a conductive metal portion. In one embodiment, the conductive metal portion comprises at least one of gold or silver. In one embodiment, the unassembled plasmonic nanoparticles comprise a coating that coats the conductive metal portion, wherein the coating facilitates selective removal from the skin surface. In one embodiment, the coating comprises at least one of silica or polyethylene glycol (PEG). In one embodiment, the method includes selectively removing the solution from the skin surface, while leaving the solution localized within the sebaceous gland. In one embodiment, the method includes irradiating the solution of unassembled plasmonic nanoparticles with an energy wavelength in a range of 750 nm to 1200 nm to induce a plurality of surface plasmons in the unassembled plasmonic nanoparticles, thereby treating acne at the sebaceous gland. In one embodiment, the mechanical vibration device is configured for bubble formation or liquid microstreaming. In one embodiment, the method includes pre-treating the skin surface to increase delivery of the unassembled plasmonic nanoparticles to the sebaceous gland with at least one of the group consisting of shaving, waxing, peeling, cyanoacrylate surface peeling, a calcium thioglycolate treatment, a surface exfoliation, a mechanical exfoliation, a salt glow, a microdermabrasion, a chemical exfoliation, a chemical exfoliation with an enzyme, a chemical exfoliation with alphahydroxy acid, and a chemical exfoliation with betahydroxy acid. In one embodiment, the concentration of the unassembled plasmonic nanoparticles is $10^9$ to $10^{16}$ particles per ml of the solution. In one embodiment, the coating is less conductive than the conductive metal portion. In one embodiment, the unassembled plasmonic nanoparticles have an optical density of 10 O.D. to 5,000 O.D. within an infrared light range. In one embodiment, the coating is semiconductive, wherein the conductive metal portion is inside the coating, and wherein the coating is less conductive than the conductive metal portion. In one embodiment, the conductive metal portion is a nanoplate, and wherein the coating is less conductive than the conductive metal portion.

In various embodiments, a method of delivering a composition of unassembled plasmonic nanoparticles to a pilosebaceous unit includes applying a solution of unassembled plasmonic nanoparticles to a skin surface, and distributing the solution of unassembled plasmonic nanoparticles with a mechanical vibration device from the skin surface to a pilosebaceous unit thereby targeting the pilosebaceous unit. In one embodiment, the mechanical vibration device comprises at least one of the group consisting of an ultrasound device, a sonic force device, a massage device, a high pressure air flow device, a high pressure liquid flow device, and a vacuum device, and a dermabrasion device. In one embodiment, the pilosebaceous unit comprises one or more structures consisting of: a hair shaft, a hair follicle, a sebaceous gland, and a hair follicle infundibulum. In one embodiment, the unassembled plasmonic nanoparticles comprise a conductive metal portion. In one embodiment, the conductive metal portion comprises at least one of gold or silver. In one embodiment, the unassembled plasmonic nanoparticles have a peak absorption wavelength of between 750 nm and 1200 nm. In one embodiment, the unassembled plasmonic nanoparticles have a concentration of $10^9$ to $10^{23}$ particles per ml of the solution. In one embodiment, the unassembled plasmonic nanoparticles comprise a coating that coats the conductive metal portion. In one embodiment, the coating comprises at least one of silica or polyethylene glycol (PEG). In one embodiment, the method includes selectively removing the solution from the skin surface while leaving the solution localized within the portion of the sebaceous gland. In one embodiment, the method includes irradiating the solution with an energy to induce the unassembled plasmonic nanoparticles to generate localized thermal damage in the sebaceous gland. In one embodiment, the method includes pre-treating the skin surface to increase delivery of the unassembled plasmonic nanoparticles to the pilosebaceous unit with at least one of the group consisting of shaving, waxing, peeling, cyanoacrylate surface peeling, a calcium thioglycolate treatment, a surface exfoliation, a mechanical exfoliation, a salt glow, a microdermabrasion, a chemical exfoliation, a chemical exfoliation with an enzyme, a chemical exfoliation with alphahydroxy acid, and a chemical exfoliation with betahydroxy acid. In one embodiment, the method includes irradiating the solution of unassembled plasmonic nanoparticles comprises exposing the solution of unassembled plasmonic nanoparticles to the energy at a wavelength of between 750 nm and 1200 nm to induce a plurality of surface plasmons in the unassembled plasmonic nanoparticles, thereby treating acne at the sebaceous gland. In one embodiment, the mechanical vibration device comprises at least a low frequency ultrasound device. In one embodiment, the method includes irradiating the solution of unassembled plasmonic nanoparticles with the energy comprises an infrared light source wavelength of between 750 nm and 1200 nm to induce a plurality of surface plasmons in the unassembled plasmonic nanoparticles, thereby treating acne at the sebaceous gland. In one embodiment, the unassembled plasmonic nanoparticles are nanoplates. In one embodiment, the unassembled plasmonic nanoparticles have an optical density of 10 O.D. to 5,000 O.D. within an infrared light range and the concentration is $10^9$ to $10^{18}$ particles per ml of the solution. In one embodiment, the method includes irradiating the solution of unassembled plasmonic nanoparticles with the energy comprises an infrared wavelength of between 750 nm and 1200 nm to induce a plurality of surface plasmons in the unassembled plasmonic nanoparticles, thereby heating the pilosebaceous unit. In one embodiment, selectively removing the composition from the skin surface comprises using water or alcohol to remove the composition from the skin surface while leaving the composition localized within the pilosebaceous unit.

Several embodiments of the present invention provide safe, tolerable, and efficacious treatments for acne and acne scarring that achieve prolonged improvement of the skin. Other light based treatments for acne, including photodynamic therapy (PDT) and long wave length lasers (e.g. 1450 nm), tend to need high energy illumination and may lack target specificity, which can lead to intolerable off-target side-effects including sensitivity to light, pain, inflammation, hyper/hypo-pigmentation, and permanent scarring. Many traditional light based procedures for treating acne scars, including ablative and non-ablative skin resurfacing, often involve aggressive treatment settings that lead to long healing times and risk of side-effect (e.g., hyperpigmentation, scarring). Several embodiments of the present invention are particularly effective for box car scars, ice pick scars, and other pitted scars, where excision is otherwise considered among the only reliable methods for treatment.

Human skin is vulnerable to damage, scarring, and an overall decline in skin smoothness or texture from disease, trauma, environmental exposure, and aging. Consumer demand for aesthetic skin enhancement that has minimal risk and provides rapid recovery has resulted in efforts to provide methods of non-surgical skin rejuvenation including skin resurfacing (e.g., lasabration, laser peel and laser vaporization). However, many skin resurfacing and other techniques resulting in the removal of epidermal layers fail to address deeper, dermal-layer scars and skin lesions.

Skin resurfacing generally involves controlled removal and, optionally, regeneration of the skin either from ablative or non-ablative damage. In general, these and related aesthetic procedures use electro-magnetic energy and/or heat to induce thermal injury in areas of the skin, and are often considered minimally invasive. Much of the prior work in skin resurfacing involves either non-fractional skin resurfacing or fractional skin resurfacing.

Non-fractional skin resurfacing uses non-fractional high-energy pulsed and/or scanned $CO_2$ or Er:YAG lasers, the energy from which when directed to the skin remove skin material in a controlled manner. Several embodiments of the present invention are particularly advantageous because some or all of the following advantages are present: (i) prolonged and unpleasant postoperative recovery period characterized by edema, oozing, and burning discomfort are avoided, (ii) substantial patient pain and discomfort during the procedure, generally requiring a significant amount of analgesia (local anesthetic for nerve blockade or general anesthesia) are not needed; (iii) reduced incidence of complications including persistent erythema, hyperpigmentation, hypopigmentation, scarring, and infection (e.g., infection with Herpes simplex virus); (iv) ability to selectively and uniformly target energy to small target regions, e.g., lesions or scars with dimensions of a few $mm^2$; (v) reduced incidence of physical impediments ("shadows") that prevent uniform delivery of the laser energy to desired areas in the target skin (which can occur because energy from certain non-fractional lasers is absorbed by water in the first few tissue layers of skin cells, thus causing any irregular contours on the skin surface (e.g. deep ice-pick or box car scars) to form shadows); (vi) reduced appearance of visible spots and/or edges after treatment due to inflammation, pigmentation, or texture changes (e.g., as would otherwise correspond to the sites of treatment including the specific edges of the laser spot); and (vii) reduced risk of irregularity in wound healing, inconsistent skin regeneration and potential scarring (which can occur, for example, when overlapping regions are treated by non-fractional lasers).

A derivative technique from the ablative use of non-fractional lasers for skin resurfacing is to induce selective thermal damage to the sub-epidermal layer (particularly the dermal layer) with no disruption of the superficial epidermal layer integrity. Such techniques have been termed non-ablative resurfacing, non-ablative subsurfacing, or non-ablative skin remodeling, and have been used as an alternative procedure. Techniques generally utilize non-ablative lasers, flashlamps, or radio frequency currents. However, while some of the adverse effects from epidermal ablation may be reduced, overall efficacy is typically limited because of epidermal sparing. Several embodiments of the invention are advantageous because irregular patterns of energy deposition are reduced or absent, thereby reducing or avoiding visible spots or edges.

Fractional resurfacing has emerged as a technique attempting to address some of the limitations in patient discomfort and recovery time from non-fractional approaches. In fractional resurfacing, thermally ablated microscopic zones of epidermis and dermis (referred to as "micro thermal zones") are spaced in a grid over the skin surface in a generally controlled, geometric pattern; the non-ablated zones in the uninjured surrounding tissue serves as a reservoir of cells that accelerate and promote safe and rapid healing. The affected zones can compromise approximately 15-70% of the skin surface area per treatment session and can be randomly selected by the orientation of the geometric pattern. Several embodiments of the present invention are particularly advantageous because (i) predetermined arrays are not needed, and thus, all or substantially all of a small target region such as a scar region that does not exceed about 25 $mm^2$ (e.g., a scar region that is within about 1-10 $mm^2$, 10-15 $mm^2$, 15-25 $mm^2$, and ranges therein) can be treated; (ii) skin outside of target regions do not need to be unnecessarily treated and the selective targeting of small regions can be achieved with respect to scars or other lesions (whether atrophic or not) where new collagen formation and re-epithelialization would provide the highest benefit; (iii) several embodiments provide a balance between aggressive treatments with high skin surface coverage that are characterized by long healing time and less aggressive treatments that have no effect; and (iv) several embodiments apply electromagnetic energy to selectively and uniformly heat small target regions that are near or below the spot size of the energy (e.g., light), while sparing other tissue.

In general, traditional methods involving light and lasers are promising for the treatment skin disorders, but are still insufficiently effective. Ultraviolet (UV)/blue light is approved by the FDA for the treatment of mild to moderate acne only, due to its anti-inflammatory effects mediated on skin cells (keratinocytes), potentially through the action of endogenous porphyrin photosensitizers within follicles. Exogenous porphyrin precursors such as 5-aminoluveulinic acid (5-ALA) have been formulated for topical or oral delivery and shown to accumulate within sebaceous follicles, absorb photons from red light exposure and form reactive oxygen species that directly damage cellular membranes and proteins. This procedure combining porphyrin application and high intensity red light, termed 'photodynamic therapy', has been demonstrated to reduce sebum production and acne by 50% for 20 weeks post-irradiation. However, high intensity energies (50-150 $J/cm^2$) are required to damage sebaceous gland skin structures, and transdermal porphyrin penetration leads to off-target side-effects which include sensitivity to light, pain, inflammation, hyper/hypo-pigmentation, and permanent scarring. Several embodiments of the invention are particularly advantageous because they locally induce photo-destruction in skin structures without affecting surrounding tissues.

Other advantages of several embodiments of the invention include reduced or no procedural pain and discomfort, post-procedural discomfort, lengthy recovery time, post-procedural infection, and unintended scarring. Additional advantages include reduced or no non-specific skin damage, skin irritation and scarring. Although many advantages are described herein, all of these advantages need not be present in any one embodiment. Several embodiments of the invention address the need to provide a procedure that enables patient-specific focusing of electromagnetic energy and heat in a manner to effectively damage small target regions while minimizing damage to surrounding tissue, thereby providing improved efficacy in remodeling target areas while substantially reducing or eliminating undesirable side effects such as procedural discomfort, post-procedural discomfort, a lengthy healing time, post-procedural infection, and unintended scarring. Several embodiments described herein provide the use of concentrated light for skin resurfacing and scar removal with less pain, and that is faster, easier and more efficacious.

Several embodiments of the invention are useful for hair removal and/or reduction. Light-based hair removal systems suffer from particularly low rates of efficacy at removing light hair (vellus, blonde, gray, red hair). Multiple (even 6 or more) treatments are insufficient to achieve a therapeutic result in blonde- gray- or red-haired patients, even with the use of topically applied chromophores such as carbon. In addition to light hair removal, thermoablative technology, as described in several embodiments of the invention herein, has untapped potential in the fields of wound healing, tissue remodeling, vascular repair, and acne treatment.

As described herein, many embodiments of the invention are used for treating acne and the scars that result from acne. Acne vulgaris results from obstruction of the pilosebaceous unit, consisting of the hair shaft, hair follicle, sebaceous gland and erector pili muscle, which leads to accumulation of sebum oil produced from the sebaceous gland and the subsequent colonization of bacteria within the follicle. Microcomedones formed as a result of accumulated sebum progress to non-inflamed skin blemishes (white/blackheads), or to skin blemishes which recruit inflammatory cells and lead to the formation of papules, nodules and pus-filled cysts. The sequelae of untreated acne vulgaris often include hyperpigmentation, scarring and disfiguration, as well as significant psychological distress. Therefore, acne treatments seek broadly to reduce the accumulation of sebum and microorganisms within follicles and the sebaceous gland. In several embodiments of the invention, reduction of microorganisms, via the photoactive particles (e.g., plasmonic nanoparticles) described herein, include, but is not limited to, inactivation of bacteria or other microorganisms, reduction in the number, growth, viability, and/or function etc. of bacteria or other microorganisms. This reduction can be accomplished by, for example, the heat generated by several of the embodiments described herein and/or the enhanced delivery of drugs and other substances. This reduction can be accomplished in target regions, including atrophic regions and small target regions as described herein.

In one aspect, described herein are compositions of matter. For example, in one embodiment, provided is a composition comprising a cosmetically acceptable carrier and a plurality of photoactive particles (e.g., plasmonic nanoparticles) in an amount effective to induce thermomodulation in a target tissue region with which the composition is topically contacted.

In some embodiments, the composition comprises, or consists essentially of photoactive particles (e.g., plasmonic nanoparticles) that are activated by exposure to energy delivered from a surface plasmon resonance excitation sources (e.g., nonlinear excitation surface plasmon resonance source) to the target tissue region. As discussed herein, at resonance wavelengths plasmonic nanoparticles can act as antennas, providing a "nonlinear excitation" at peak resonance or, in other words, an enhanced extinction cross section for a given physical cross-section of material when compared to non-plasmonic photoactive materials of the same dimension. Thus, in several embodiments, plasmonic materials are able pull more energy from delocalized electromagnetic waves surrounding the material at peak resonance than non-plasmonic photoactive material of the same dimension.

In further or additional embodiments, described herein are compositions comprising, or consisting essentially of, at least one photoactive particles (e.g., plasmonic nanoparticle) that comprises a metal, metallic composite, metal oxide, metallic salt, electric conductor, electric superconductor, electric semiconductor, dielectric, quantum dot or composite from a combination thereof. In further or additional embodiments, provided herein is a composition wherein a substantial amount of the photoactive particles (e.g., plasmonic particles) present in the composition comprise geometrically-tuned nanostructures. In certain embodiments, provided herein is a composition wherein photoactive particles (e.g., plasmonic particles) comprise any geometric shape currently known or to be created that absorb light and generate plasmon resonance at a desired wavelength, including nanoplates, solid nanoshells, hollow nanoshells, partial nanoshells, nanorods, nanorice, nanospheres, nanofibers, nanowires, nanopyramids, nanoprisms, nanostars, nanocrescents, nanorings, or a combination thereof. In yet additional embodiments, described herein is a composition wherein the photoactive particles (e.g., plasmonic particles) comprise silver, gold, nickel, copper, titanium, silicon, galadium, palladium, platinum, or chromium, as well as including metal alloys, composites, and amalgams.

In some embodiments, provided herein is a composition comprising a cosmetically acceptable carrier that comprises, or consists essentially of, an additive, a colorant, an emulsifier, a fragrance, a humectant, a polymerizable monomer, a stabilizer, a solvent, or a surfactant. In one embodiment, provided herein is a composition wherein the surfactant is selected from the group consisting of: sodium laureth 2-sulfate, sodium dodecyl sulfate, ammonium lauryl sulfate, sodium octech-1/deceth-1 sulfate, lipids, proteins, peptides or derivatives thereof. In one embodiment, provided is a composition wherein a surfactant is present in an amount between about 0.1 and about 10.0% weight-to-weight of the carrier. In yet another embodiment, the solvent is selected from the group consisting of water, propylene glycol, alcohol, hydrocarbon, chloroform, acid, base, acetone, diethylether, dimethyl sulfoxide, dimethylformamide, acetonitrile, tetrahydrofuran, dichloromethane, and ethylacetate. In one embodiment, the composition comprises, or consists essentially of, photoactive particles (e.g., plasmonic particles) that have an optical density of at least about 1 O.D. at one or more (e.g., 50 O.D.-10,000 O.D.) peak resonance wavelengths at, for example, infrared.

In further or additional embodiments, described herein is a composition wherein photoactive particles (e.g., plasmonic particles) comprise a hydrophilic or aliphatic coating, wherein the coating does not substantially adsorb to skin of a mammalian subject, and wherein the coating comprises polyethylene glycol, silica, silica-oxide, polyvinylpyrrolidone, polystyrene, polyquaternium(s), a protein or a peptide. In yet an additional embodiment, the thermomodulation comprises damage, ablation, thermoablation, lysis, denaturation, deactivation, activation, induction of inflammation, activation of heat shock proteins, perturbation of cell-signaling or disruption to the cell microenvironment in the target tissue region. Still further, in certain presentations the target tissue region comprises a sebaceous gland, a component of a sebaceous gland, a sebocyte, a component of a sebocyte, sebum, or hair follicle infundibulum. In further embodiments, the target tissue region comprises a bulge, a bulb, a stem cell, a stem cell niche, a dermal papilla, a cortex, a cuticle, a hair sheath, a medulla, an arrector pili muscle, a Huxley layer, or a Henle layer.

In another aspect, described herein are methods of performing targeted ablation of tissue. For example, in one embodiment, provided is a method for performing targeted ablation of a tissue to treat a mammalian subject in need thereof, comprising the steps of i) topically administering to a skin surface of the subject a composition of photoactive particles (e.g., plasmonic particles) ii) providing penetration means to redistribute the plasmonic particles from the skin surface to a component of dermal tissue; and iii) causing irradiation of the skin surface by light. In further or additional embodiments, provided is a method wherein the light source comprises excitation of mercury, xenon, deuterium, or a metal-halide, phosphorescence, incandescence, luminescence, light emitting diode, or sunlight. In still further or additional embodiments, provided is a method wherein the penetration means comprises high frequency ultrasound, low frequency ultrasound (e.g., frequencies of 1 kHz to 500 kHz, e.g., 1 kHz-100 kHz, 5 kHz-45 kHz, 20 kHz-50 kHz, 30 kHz-40 kHz, 30 kHz, 40 kHz, and any ranges or frequencies therein), massage (e.g., hand massage, vibration, mechanical vibration, and/or at frequencies of less than 1 kHz, 1 Hz-900 Hz, 5-500 Hz, 10-100 Hz, 1-80 Hz, 50-250 Hz, and any frequencies therein), iontophoresis, high pressure air flow, high pressure liquid flow, vacuum, pre-treatment with fractionated photothermolysis or dermabrasion, or a combination thereof, and/or pre-treatment with heat, massage, ultrasound or a combination thereof. In still further embodiments, provided is a method wherein the irradiation comprises light having a wavelength of light between about 200 nm and about 10,000 nm (e.g., 700 nm to 1,200 nm, 600 nm to 1,500 nm, 500 nm to 2,000 nm), a fluence of about 0.1 to about 100 joules/cm$^2$ (e.g., 1 to 60 joules/cm$^2$, 5 to 50 joules/cm$^2$ 10 to 30 joules/cm$^2$), a pulse width of about 1 femptosecond to about 1 second (e.g., 100 microsecond to 500 millisecond, 100 microsecond to 1000 microseconds, 1 millisecond to 10 millisecond, 10 millisecond to 100 millisecond, 100 millisecond to 500 millisecond), and a repetition frequency of about 1 Hz to about 1 THz (e.g., 1 Hz to 10 Hz, 1 Hz to 1 MHz, 1 Hz to 1 GHz).

In a further aspect, provided herein are some embodiments of compositions comprising a cosmetically acceptable carrier, an effective amount of sodium dodecyl sulfate, and a plurality of photoactive particles (e.g., plasmonic nanoparticles) in an amount effective to induce thermal damage in a target tissue region with which the composition is topically contacted, wherein the nanoparticles have an optical density of at least about 1 O.D. (e.g., 10 O.D., 50 O.D., 100 O.D., 1000 O.D., and/or 10,000 O.D.) at a resonance wavelength in the range of about 810 nanometers or 1064 nanometers, wherein the plasmonic particles comprise a silica coating from about 5 to about 35 nanometers, wherein the acceptable carrier comprises water and propylene glycol. In yet another aspect, provided are some embodiments of systems for laser ablation of hair or treatment of acne comprising a composition and a source of plasmonic energy suitable for application to the human skin.

In several embodiments, the invention comprises a method for reducing dermal scar tissue (e.g., in a human subject) comprising: i) identifying a target region of skin tissue on a human subject, wherein the target region comprises an epidermal surface and dermal scar tissue, wherein the target region does not exceed about 25 mm$^2$; (ii) contacting the epidermal surface of the target region with a non-dispersive composition comprising a photoactive material; and (iii) delivering to the target region energy in the 700 nm to about 1200 nm range in an amount sufficient to heat at least a portion of the dermal scar tissue to a temperature of at least 40 degrees Celsius for a period of time sufficient to reduce the dermal scar tissue. The temperature may be in the range of about 40 to 45, 40 to 50, 40 to 55, 40 to 60, 40 to 65, 40 to 70, 40 to 75, 40 to 80 or 40 to above 80. The time period may be in the range of 1 femtosecond to about 1 second (e.g., 100 microsecond to 1000 microseconds, 1 millisecond to 10 millisecond, 10 millisecond to 100 millisecond, 100 millisecond to 500 millisecond).

In some embodiments, the invention comprises a method for reducing dermal scar tissue (e.g., in a human subject) comprising: (i) identifying a target region of skin tissue on a human subject, wherein the target region comprises an epidermal surface and dermal scar tissue comprising a pathophysiological collagen deposition, dermal matrix, or epidermal surface, wherein the target region does not exceed about 25 mm$^2$; (ii) contacting the epidermal surface of the target region with a non-dispersive composition comprising a photoactive material; and (iii) delivering to the target region energy in the 700 nm to about 1200 nm range in an amount sufficient to heat at least a portion of the dermal scar tissue to a temperature sufficient to cause damage and regeneration, thereby reducing the dermal scar tissue.

For embodiments in which the target region (e.g., atrophic scar) does not exceed about 25 mm$^2$ the region may be sized in at least one dimension as follows: 0.1 mm$^2$ to 5 mm$^2$, 5 mm$^2$-10 mm$^2$, 10 mm$^2$-15 mm$^2$, 15 mm$^2$-25 mm$^2$, 0.1 mm$^2$-25 mm$^2$ overlapping ranges therein. These dimensions can apply, for example, to the surface area of the region (the inner surface area of an atrophic scar). The target region (e.g., atrophic scar) may also have at least one dimension (e.g., depth, length, width) in the following ranges: 0.01 mm-10 mm (e.g. 0.5 mm to 1.5 mm, 0.25 mm-2.5 mm, 1 mm to 8 mm, 5 mm to 10 mm, and overlapping ranges therein). In one embodiment, the target region (e.g., atrophic scar) is at least 0.25 mm mean thickness (e.g., 0.01-0.25 mm).

In several embodiments, the methods can be performed in any order, with any step repeated one or more times. In some embodiments of the methods, the contacting and/or delivering steps can be repeated 1, 2, 3, 4, 5, 6, 7, 8, 9, 10, 15, 20, 24, or more times. In several embodiments, the methods for treating the target regions are repeated one or more times on one or more additional target regions. For example, the procedure may be performed/repeated 1-24 times (e.g., 2, 3, 4, 5, 10 or more times). A single target region may be treated, or alternatively, multiple target regions may be treated sequentially or simultaneously.

In several embodiments, the dermal scar tissue comprises a scar resulting from an acne vulgaris infection. The dermal scar tissue may be atrophic (e.g., recessed). The target region of skin tissue is located on the face or neck of a human subject.

In several embodiments, the photoactive material comprises carbon. In several embodiments, the photoactive material comprises graphite. In several embodiments, the photoactive material comprises a plasmonic nanoparticle. In several embodiments, the photoactive material comprises a silver plasmonic nanoparticle. In several embodiments, the photoactive material comprises a silica-coated silver plasmonic nanoparticle. In several embodiments, the photoactive material is present at a concentration of from about 0.01% to about 10% volume to volume ratio, or greater than 10% volume to volume ratio (e.g., 0.01%-0.1%, 0.1%-1%, 1%-10%. In several embodiments, the photoactive material does not substantially penetrate the epidermal surface. In several embodiments, the energy comprises a spot diameter anywhere in the range of about 0.5 mm to about 20 mm at the epidermal surface.

In several embodiments, the non-dispersive composition comprises a volume of about 10 microliters with a diameter of less than about 5 mm at the epidermal surface for at least one minute after contacting of the non-dispersive composition with the epidermal surface. In several embodiments, the non-dispersive composition does not laterally migrate along the epidermal surface at a rate greater than about 1 mm per minute. In several embodiments, the non-dispersive composition comprises at least one of water, a humectant, a surfactant, a thickener, a dye, an antiseptic, an anti-inflammatory agent, an anti-oxidant, a vitamin, a fragrance, an oil, or a topical anesthetic. In several embodiments, the non-dispersive composition is contacted with the epidermal surface with a volume of about 1 to about 50 microliters of the non-dispersive composition.

In several embodiments, the methods further comprise the step of contacting the epidermal surface of the target region with an adhesive compound prior to contacting the epidermal surface with the non-dispersive composition, wherein the adhesive compound increases retention of the photoactive material at the target region.

In several embodiments, the invention comprises a means for delivering photoactive particles into small target regions. In several embodiments, the means for delivering includes an apparatus for delivering a formulation into a target region (e.g., an acne scar or other atrophic scar) of a human subject. As used herein, the terms formulation and composition can be used interchangeably. In several embodiments, the apparatus, comprises a supply of a liquid formulation comprising an photoactive material, which, when put in substantial physical contact with a target area of a skin surface of a human subject, with the target area comprising an acne scar or portion thereof, is capable of penetrating the skin surface at the target area to denature at least one pathophysiological collagen deposition present in the acne scar, by delivering sufficient thermal energy to the targeted area such that the temperature of the collagen deposition in the target area is elevated above the denaturation temperature of the collagen deposition. In several embodiments, the apparatus enables the liquid formulation, when the liquid formulation is put in contact with the target area, to be substantially retained in the target area, wherein the apparatus delivers the liquid formulation onto the target area in a volume of from about 0.01 ml to about 1 ml.

In several embodiments, the invention comprises a system for affecting collagen (e.g., denaturing collagen) present in a target region such as an atrophic region (e.g., acne scar) comprising: (i) an apparatus for delivering a formulation, and (ii) a light source. In several embodiments, the apparatus contains a supply of a liquid formulation comprising an photoactive material, which, when put in substantial physical contact with a target area of a skin surface of a human subject, the target area comprising an acne scar or portion thereof, is capable of penetrating the skin surface at the target area to denature at least one pathophysiological collagen deposition present in the acne scar, by delivering sufficient thermal energy to the targeted area such that the temperature of the collagen deposition in the target area is elevated above the denaturation temperature of the collagen deposition. In several embodiments the apparatus enables the liquid formulation, when the liquid formulation is put in contact with the target area, to be substantially retained in the target area, wherein the apparatus delivers the liquid formulation onto the target area in a volume of from about 0.01 ml to about 1 ml.

In several embodiments the a means for delivering photoactive particles into small target regions includes apparatus comprising a needle-nose applicator, a fine tip applicator, a pipette, a dropper, a brush, an applicator, a module, a capsule, a syringe, and/or a sprayer (e.g., a micro-sprayer such an airbrush). In several embodiments the apparatus is capable of delivering a volume of from about 1 to about 50 microliters (e.g., 1-10, 10-25, 25-50 microliters) of the formulation on the target area such that the surface area of the target area contacted by the formulation is less than about 25 mm$^2$. The formulation is liquid in many embodiments (and includes gelatinous formulations), but also includes solid forms, such as grains, granules, and/or fine powders. In several embodiments the light source comprises an infrared laser or intense pulsed light (IPL).

In some embodiments, the invention comprises a kit for treating the skin. The kit includes some or all of the following: a formulation of photoactive particles (such as nanoparticles and/or chromophores), means for delivering the formulation to the skin (e.g., to atrophic regions or other target regions), a light source, and instructions for use. In one embodiment, an energy source (such as light source) is also included. In some embodiments a means of removing the formulation of photoactive particles from the skin or modifying the distribution of the formulation on the skin is provided. In various embodiments, drugs or other substances to be delivered to the dermis and epidermis are provided which can either enhance the effects of the treatment, or decrease the side effects caused by partial damage of the epidermis and/or dermis, or both.

The methods summarized above and set forth in further detail below describe certain actions taken by a practitioner; however, it should be understood that they can also include the instruction of those actions by another party. Thus, actions such as "identifying a target region" can include "instructing the identification of a target region" and "delivering an energy" can include "instructing the delivery of an energy."

BRIEF DESCRIPTION OF THE DRAWINGS

FIG. 1 is illustrative of schematics depicting certain embodiments of the use of formulations for hair removal and acne treatment. Depicted is (A) for hair removal, the plasmonic nanoparticle formulation (black) is 1. applied topically to human skin, 2. delivered deep into the follicle and washed from the skin surface, 3. irradiated with a clinical laser at a wavelength resonant to the peak absorption wavelength of the plasmonic particle, and 4. shed from the follicle along with the damaged hair follicle; and (B) for acne treatment, the plasmonic nanoparticle formulation (black) is 1. applied topically to human skin, 2. delivered specifically into the sebaceous gland and washed from the skin surface, 3. irradiated with a clinical laser at a wavelength resonant to the peak absorption wavelength of the plasmonic particle, and 4. shed from the target site where the accumulated sebum and sebum-producing capabilities of the sebaceous gland are destroyed.

FIG. 17 is a table summarizing experimental data measuring the performance of three embodiments of delivery devices to deliver a single embodiment of the composition to various depths in tissue.

FIG. 18 illustrates images of the delivery of a composition in skin models with various embodiments of delivery devices.

DETAILED DESCRIPTION

Figure 2:
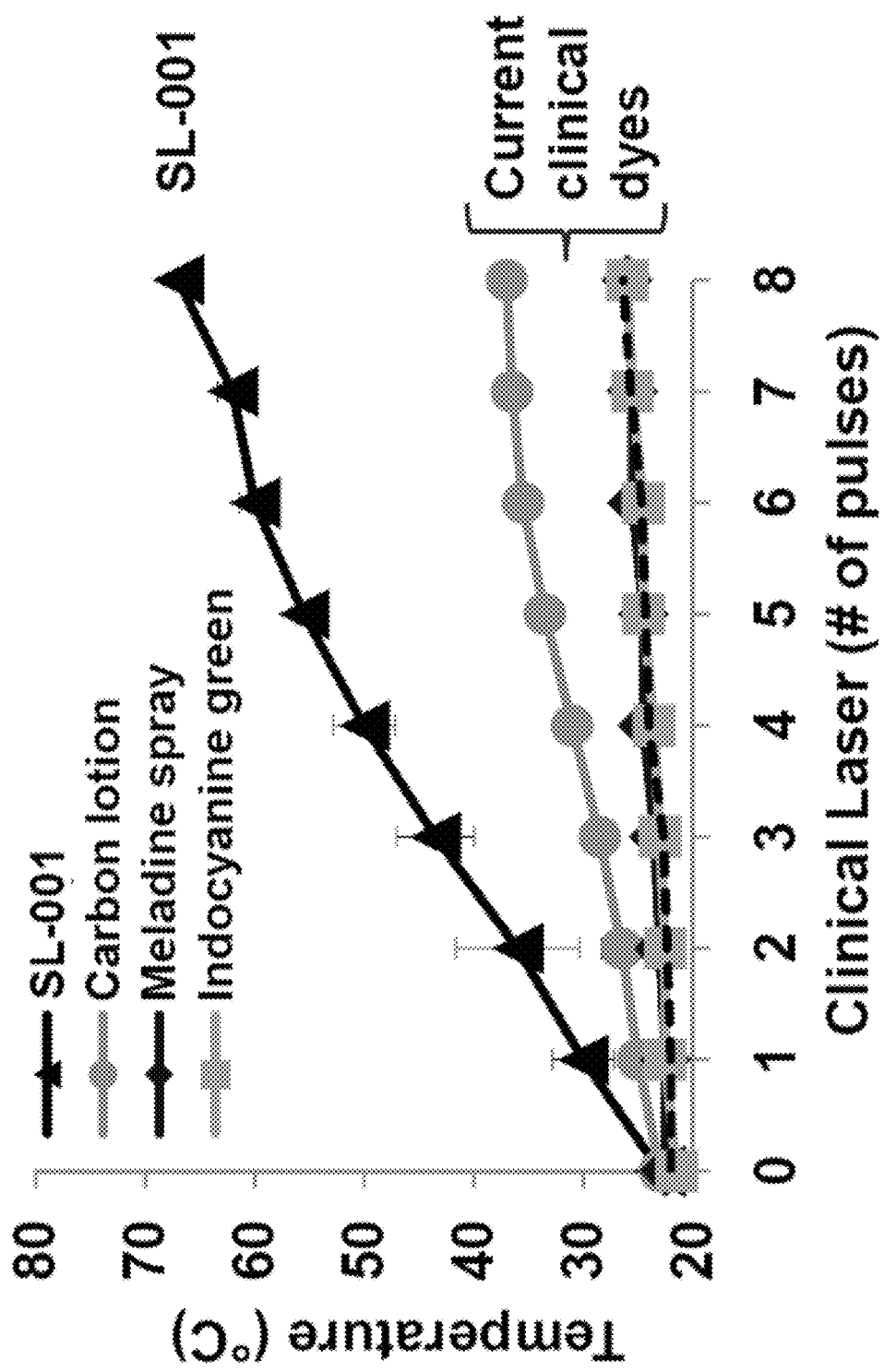
FIG. 2 is illustrative of a temperature profile of certain embodiments of the formulations of plasmonic nanoparticles (SL-001, triangles) provided herein compared to certain embodiments of clinical dyes carbon lotion (circles), meladine spray (diamonds), and indocyanine green (squares), after exposure to 1064 nm, 20 J/cm$^2$, 55 ms laser pulses. SL-001 and dyes were equally diluted at 1:1000 from clinical concentration (SL-001 1000 O.D., carbon 20-200 mg/ml, meladine 1 mg/ml, ICG 5 mg/ml). n=3, error S.D. of mean.

The biology of physiological and pathophysiological tissue growth and remodeling, and alterations in cell morphology is more complex than generally appreciated, involving an interacting network of biological compounds, physical forces, and cell types.

An object of the subject matter described herein is to provide compositions, methods and systems for noninvasive and minimally-invasive treatment of skin and underlying tissues, or other accessible tissue spaces with the use of photoactive compounds (including but not limited to photoactive particles such as nanoparticle, plasmonic nanoparticles, etc.). In some embodiments, the invention describes the development and utilization of compositions containing photoactive materials (e.g., nanoparticles and other materials) for the treatment of small target regions of skin including acne scars and other skin conditions. In one embodiment, such compositions are generally applied topically, through an apparatus that provides the composition in a form suitable for contact with and retention at a target region of skin in a manner that encompasses irradiating the skin with light (e.g., electromagnetic radiation) having a wavelength sufficient to ablate or otherwise damage the target region of skin and cause remodeling of the skin tissue. In various embodiments, the treatment includes, but is not limited to, hair removal, hair growth and regrowth, and skin rejuvenation or resurfacing, acne removal or reduction, wrinkle reduction, pore reduction, ablation of cellulite and other dermal lipid depositions, wart and fungus removal, thinning or removal of scars including hypertrophic scars and keloids, abnormal pigmentation (such as port wine stains), tattoo removal, and skin inconsistencies (e.g. in texture, color, tone, elasticity, hydration, and including sun spots, age spots, freckles, and other inconsistencies). Other therapeutic or preventative methods include but are not limited to treatment of hyperhidrosis, anhidrosis, Frey's Syndrome (gustatory sweating), Horner's Syndrome, and Ross Syndrome, actinic keratosis, sebhorreic keratosis, keratosis follicularis, dermatitis, vitiligo, pityriasis, psoriasis, lichen planus, eczema, alopecia, psoriasis, malignant or non-malignant skin tumors, onychomycosis, sebhorreic dermatitis, atopic dermatitis, contact dermatitis, herpes simplex, Human papillomavirus (HPV), and dermatophytosis.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting. Other features of the disclosure are apparent from the following detailed description and the claims.

"Administer" and "administration" as used herein, include providing or causing the provision of a material to a subject, such as by a topical, subdermal, subcutaneous, intradermal, enteral, parenteral, rectal, nasal, intravenous, intramuscularly, intraperitoneal, or other route.

A "carrier suitable for administration" to a subject is any material that is physiologically compatible with a topical or route of administration to a desired vertebrate subject. Carriers can include solid-based, dry materials for formulation; or the carrier can include liquid or gel-based materials for formulations into liquid or gel forms. The specific type of carrier, as well as the final formulation depends, in part, upon the selected route(s) of administration and the type of product.

A "comparable amount" is an amount that is measurably similar to a given reference or standard.

The "components" of a formulation include any products or compounds associated with or contained within it.

An "effective dose", "effective amount" or "therapeutic amount" is an amount sufficient to elicit the desired pharmacological, cosmetic or therapeutic effects, thus resulting in effective prevention or treatment of a disease or disorder, or providing a benefit in a vertebrate subject.

A "therapeutic effect" or "therapeutically desirable effect" refers to a change in a domain or region being treated such that it exhibits signs of being effected in the manner desired, e.g., cancer treatment causes the destruction of tumor cells or halts the growth of tumor cells, acne treatment causes a decrease in the number and/or severity of blemishes, hair removal treatment leads to evident hair loss, or wrinkle reduction treatment causes wrinkles to disappear.

An "isolated" biological component (such as a nucleic acid molecule, protein, or cell) has been substantially separated or purified away from other biological components in which the component was produced, including any other proteins, lipids, carbohydrates, and other components.

A "nanoparticle", as used herein, refers generally to a particle having at least one of its dimensions from about 0.1 nm to about 9000 nm. (e.g., 1 nm-500 nm, 10 nm-300 nm, 100 nm-500 nm.).

A "subject" or "patient" as used herein is any vertebrate species.

As used herein, a "substantially pure" or "substantially isolated" compound is substantially free of one or more other compounds.

A "target tissue" includes a region of an organism to which a physical or chemical force or change is desired. As described herein, various embodiments of target tissues for acne treatment include a sebaceous gland, while various embodiments of target tissues for hair removal include a pilosebaceous unit, a hair infundibulum, a hair follicle, or a non-follicular epidermis. Target tissues for sweat or hyperhidrosis include a sweat gland. A "region" of a target tissue includes one or more components of the tissue. In some embodiments, target tissue regions include the stem cell niche, bulge, sebaceous gland, dermal papilla, cortex, cuticle, inner root sheath, outer root sheath, medulla, Huxley layer, Henle layer or arrector pili muscle. A "domain" of a target tissue region includes basement membrane, extracellular matrix, cell-surface proteins, unbound proteins/analytes, glycomatrices, glycoproteins, or lipid bilayer.

A compound that is "substantially free" of some additional contents is largely or wholly without said contents.

A "plasmonic nanoparticle" is a nanometer-sized metallic structure within which localized surface plasmons are excited by light. These surface plasmons are surface electromagnetic waves that propagate in a direction parallel to the metal/dielectric interface (e.g., metal/air or metal/water).

A "light-absorbing nanomaterial" includes a nanomaterial capable of demonstrating a quantum size effect.

As described herein, provided are compositions that contain plasmonic nanoparticles to induce selective thermomodulation in a target tissue.

Plasmonic Nanoparticles.

In various embodiments, a composition comprises plasmonic nanoparticles. In various embodiments, such compositions contain from about 2 to about $1 \times 10^{18}$ or up to $10^{23}$ nanoparticles (e.g., $10^9$ to about $10^{16}$ nanoparticles), such as $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ particles, including such as ranges between about $10^9$ to $10^{23}$, $10^9$ to $10^{18}$, $10^9$ to $10^{16}$, $10^9$ to $10^{15}$, $10^9$ to $10^{14}$, $10^9$ to $10^{13}$, $10^9$ to $10^{12}$, $10^9$ to $10^{11}$, 10 $10^9$ to $10^{11}$ particles per ml. In one embodiment, the range is between about $10^5$ to $10^{18}$ per ml of composition or solution. In one embodiment, the range is between about $10^9$ to $10^{16}$ per ml of composition or solution The numbers of particles may include the number, or any range of any numbers disclosed. In some embodiments, a concentration of particles is expressed as the number of particles per milliliter of, for example, the solution. In one embodiment, the compositions contain about $10^{11}$ to $10^{13}$ particles so that the amount of particles localized to an effective 1 ml treatment volumes is from $10^9$ to $10^{11}$. In various embodiments, the compositions contain nanoparticles in a concentration of from about 1 O.D. to about 10,000 O.D. For embodiments wherein a greater concentration of nanoparticles to a target region is desired, compositions contain particle concentrations with optical densities of, for example, 10 O.D.-5000 O.D. more specifically 100 O.D.-1000 O.D., or optical densities greater than 1,000 O.D. In certain embodiments wherein increased concentration of nanoparticles to a target region is desired, compositions contain particle concentrations with optical densities (O.D.) of 10 O.D.-1000 O.D., or optical densities greater than 1,000 O.D. In some embodiments, the optical density of a composition is any of 100 O.D., plus or minus 10%, plus or minus 5%, and/or plus or minus 1%. In some embodiments, the optical density of a composition is 100 O.D. to 10,000 O.D. e.g., 1000 O.D., plus or minus 10%, plus or minus 5%, and/or plus or minus 1%. In some embodiments these correspond to concentrations of about 1-10% w/w (e.g., about 1, 2, 3, 4, 5, 6, 7, 8, 9, or 10%, or ranges within these numbers) or more of nanoparticles. Determination of O.D. units in a composition is determined using devices and analyses known in the art.

Nanoparticles may be homogenous or heterogeneous in size and other characteristics. The size of the nanoparticle is generally about 0.1 nm to about 50,000 nm (e.g., about 0.1 nm to about 5,000 nm) in at least one dimension. Some variation in the size of a population of nanoparticles is to be expected. For example, the variation might be less than 0.01%, 0.1%, 0.5%, 1%, 5%, 10%, 15%, 25%, 50%, 75%, 100%, 200% or greater than 200%, or any range between any numbers therein (e.g., 0.01%-200%, 0.1%-10%, 15%-75%, 0.1%-100%, etc.). In certain embodiments where optimal plasmonic resonance is desired, a particle size in the range of from about 10 nm to about 100 nm is provided. Alternatively, in embodiments where enhanced penetration of the nanoparticles into a target tissue region such as a hair follicle is desired, a particle size in the range of from about 100 nm to about 1000 nm is provided. Modulation of particle size present in the composition is also a useful means of concentrating the composition in a target domain. Further, as described herein, nanoparticles having a size range of from about 10 nm to about 100 nm can be used as component of a larger molecular structure, generally in the range of from about 100 nm to about 1000 nm. For example, the plasmonic nanoparticle can be surface coated to increase its size, embedded into an acceptable carrier, or it can be cross-linked or aggregated to other particles, or to other materials, that generate a larger particle. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., hair follicle) and limit delivery to non-target region (e.g. dermis). In one embodiment, the invention comprises a composition comprising at least about 1 O.D. (e.g., at least 10 O.D.) of coated plasmonic nanoparticles (e.g., comprising silica or polyethylene glycol (PEG)) having a mean length in at least one dimension greater than about 30 nanometers, wherein the coated nanoparticles are formulated in an acceptable carrier to be effective in induction of selective thermoablation in a target tissue region with which the composition is contacted, wherein the affinity of the coated nanoparticles for the target tissue region is substantially greater than the affinity of the coated nanoparticles for a non-target tissue region.

Some considerations when generating embodiments of nanoparticles include: 1) the zeta potential (positive, negative, or neutral) and charge density of the particles and resulting compositions; 2) the hydrophilicity/hydrophobicity of the particles and resulting compositions; 3) the presence of an adsorption layer (e.g., a particle slippage plane); and 4) target cell adhesion properties. Nanoparticle surfaces can be functionalized with thiolated moieties having negative, positive, or neutral charges (e.g. carboxylic acid, amine, hydroxyls) at various ratios. Moreover, anion-mediated surface coating (e.g. acrylate, citrate, and others), surfactant coating (e.g., sodium dodecyl sulfate, sodium laureth 2-sulfate, ammonium lauryl sulfate, sodium octech-1/deceth-1 sulfate, lecithin and other surfactants including cetyl trimethylammonium bromide (CTAB), lipids, peptides), or protein/peptide coatings (e.g. albumin, ovalbumin, egg protein, milk protein, other food, plant, animal, bacteria, yeast, or recombinantly-derived protein) can be employed. Block-copolymers are also useful. Further, one will appreciate the utility of any other compound or material that adheres to the surface of light-absorbing particles to promote or deter specific molecular interactions and improve particle entry into pores or follicles. In some embodiments, the particle surface is unmodified. Modulation of hydrophilicity versus hydrophobicity is performed by modifying nanoparticle surfaces with chemistries known in the art, including thiols, dithiolane, silanes, isothiocyanates, short polymers (e.g., PEG), or functionalized hydrocarbons. Polymer chains (e.g., biopolymers such as proteins, polysaccharides, lipids, and hybrids thereof; synthetic polymers such as polyethyleneglycol, PLGA, and others; and biopolymer-synthetic hybrids) of different lengths and packing density are useful to vary the adsorption layer/slippage plane of particles.

Optical Absorption.

In various embodiments, nanoparticles have optical absorption qualities of about 10 nm to about 10,000 nm, e.g., 100-500 nm, 500-750 nm, 600-900 nm, 700-1,000 nm, 800-1,200 nm, or 500-2,000 nm. In specific embodiments, the nanoparticles have optical absorption useful to excitation by standard laser devices or other light sources. For example, nanoparticles absorb at wavelengths of about 755 nm (alexandrite lasers), in the range of about 800-810 nm (diode lasers), or about 1064 nm (Nd:YAG lasers). Similarly, the nanoparticles absorb intense pulsed light (IPL), e.g., at a range of about 500 nm to about 1200 nm.

Assembly.

In various embodiments, the nanoparticles can contain a collection of unassembled nanoparticles. By "unassembled" nanoparticles it is meant that nanoparticles in such a collection are not bound to each other through a physical force or chemical bond either directly (particle-particle) or indirectly through some intermediary (e.g. particle-cell-particle, particle-protein-particle, particle-analyte-particle). In other embodiments, the nanoparticle compositions are assembled into ordered arrays. In particular, such ordered arrays can include any three dimensional array. In some embodiments, only a portion of the nanoparticles are assembled, e.g., 5, 10, 15, 20, 25, 30, 35, 40, 45, 50, 55, 60, 65, 70, 75, 80, 86, 90, 95, 99% or greater than 99% of the nanoparticles are assembled in an ordered array. The nanoparticles are assembled by a van der Walls attraction, a London force, a hydrogen bond, a dipole-dipole interaction, or a covalent bond, or a combination thereof.

"Ordered array"-"Ordered arrays" can take the form of a macrostructure from individual parts that may be patterned or unpatterned in the form of spheres, colloids, beads, ovals, squares, rectangles, fibers, wires, rods, shells, thin films, or planar surface. In contrast, a "disordered array" lacks substantial macrostructure.

Geometrically Tuned Nanostructures.

In various embodiments, the particles are formable in all shapes currently known or to be created that absorb light and generate a plasmon resonance at a peak-wavelength or composition of wavelengths from 200 nm to 10,000 nm. In non-limiting examples, the nanoparticles are shaped as spheres, ovals, cylinders, squares, rectangles, rods, stars, tubes, pyramids, stars, prisms, triangles, branches, plates or comprised of a planar surface. In non-limiting examples, the plasmonic particles comprise nanoplates, solid nanoshells, hollow nanoshells nanorods, nanorice, nanospheres, nanofibers, nanowires, nanopyramids, nanoprisms, or a combination thereof. Plasmonic particles present in the composition comprise a substantial amount of geometrically-tuned nanostructures defined as 5, 10, 15, 25, 50, 75, 80, 85, 90, 95, 98, 99, 99.9 or greater than 99.9% of particles.

Composition.

In various embodiments, the nanoparticle is a metal (e.g., gold, silver), metallic composite (e.g., silver and silica, gold and silica), metal oxide (e.g. iron oxide, titanium oxide), metallic salt (e.g., potassium oxalate, strontium chloride), intermetallic (e.g., titanium aluminide, alnico), electric conductor (e.g., copper, aluminum), electric superconductor (e.g., yttrium barium copper oxide, bismuth strontium calcium copper oxide), electric semiconductor (e.g., silicon, germanium), dielectric (e.g., silica, plastic), or quantum dot (e.g., zinc sulfide, cadmium selenium). In non-limiting examples, the materials are gold, silver, nickel, platinum, titanium, palladium, silicon, galadium. Alternatively, the nanoparticle contains a composite including multiple metals (e.g., alloy), a metal and a dielectric, a metal and a semiconductor, or a metal, semiconductor and dielectric.

Coating.

In some embodiments, the composition contains coated particles.

| Type of Material | Properties | Examples of Materials |
|---|---|---|
| Biorecognitive material | Moiety with affinity or avidity for a substrate or analyte | Antibody, peptide, phage, DNA, RNA |
| Bioactive material | Moiety (e.g., protein, analyte) that interrogates or modulates the activity of biologic entity or cell | Growth factor (e.g. VEGF), cytokine, cell surface receptors, receptor ligands, G-protein, kinase/phosphatase |
| Biological material | Material that is sourced from living matter | albumin, ovalbumin, egg protein, milk protein, other food, plant, animal, bacteria, yeast, or recombinantly derived protein; peptides; enzymes, lipids, fatty acids, sugars |

-continued

| Type of Material | Properties | Examples of Materials |
|---|---|---|
| Biocide material | Material that is active in killing, destroying, or disturbing biological matter | Synthetic or natural pesticides, synthetic or natural anti-microbials |
| Dielectric materials | An insulator that may be polarized by an electric field | Silicon, doped semiconductors |
| Chemorecognitive material | Material that is able to interact with a moiety for binding, biological or chemical reactions | Receptor, receptor ligand, chemical molecule |
| Chemical active material | Material that causes the transformation of a substance | Aldehyde, halogens, metals |
| Polymer/dendrimer | Long chain molecule (linear or branched, block or co-block) | PLGA, PEG, PEO, polystyrene, carboxylate styrene, rubbers, nylons, silicones, polysaccharides |
| Environmentally sensitive polymer | Surface molecule that changes by its environment (e.g. acid) | Ph sensitive bond, light sensitive bond, heat sensitive bond, enzyme sensitive bond, hydrolytic bond |
| Hydrogel | Polymer with high hydrophilicity and water "ordering" capacity | Synthetic 2-hydroxyethyl metacrylate (HEMA)-based, polyethylene glycol (PEG)-based, PLGA, PEG-diacrylate; Natural ionic gels, alginate, gelatin, hyaluronic acids, fibrin |
| Metal | Thin metal coating to achieve improved resonance and/or functionalization capacity | Gold, silver, nickel, copper, platinum, titanium, chromium, palladium. |
| Semiconductors | Semiconductor layer or core that enhance Plasmon resonance | Silicon and galadium. |
| Polymer containing a fluorescent marker | Fluorophore cross linked to a polymer coat or directly to the surface of the particle | Fluorescein, rhodamine, Cy5, Cy5.5, Cy7, Alexa dyes, Bodipy dyes |
| Matrix | Matrix coating that increases solubility of nanoparticles and/or reduces "stickiness" to biological structures | Silica, polyvinyl pyrrolidone, polysulfone, polyacrylamide, polyethylene glycol, polystyrene cellulose, pplyquaterniums, lipids, surfactants, carbopol. |

Biological Molecules.

In various embodiments, the composition may contain a peptide, a nucleic acid, a protein, or an antibody. For example a protein, antibody, peptide, or nucleic acid that binds a protein of a follicular stem cell (e.g., keratin 15), a protein, glycomatrix, or lipid on the surface of a cell or stem cell, a protein, peptide, glycomatrix of the extracellular matrix or basement membrane.

Charged Moieties.

In various embodiments, the coated nanoparticles may contain charged moieties whereby those charges mediate enhanced or diminished binding to components within or outside the hair follicle via electrostatic or chemical interactions.

| Class of Moiety | Properties | Examples of Moieties |
|---|---|---|
| Polar moieties | Neutral charge but increases hydrophilicity in water | Hydroxyl groups, isothiocyanates |
| Non-polar moieties | Increases hydrophobicity and or improves solubility | Hydrocarbons, myristoylated compounds, silanes, isothiocyanates |
| Charged moieties | Functional surface modifications that change the zeta potential, isoelectric point, or pKa, and impact adsorption/binding to complementary charge compounds | Amines, carboxylic acids, hydroxyls |
| Ionic moieties | Surface groups that have a single ion | Ammonium salts, chloride salts |
| Basic moieties | Groups that donate a hydrogen ions | Amides, hydroxides, metal oxides, fluoride |
| Acidic moieties | Moieties that accept hydrogen ions | Carboxylic acids, sulfonic acids, mineral acids |
| Oxidative moieties | Moieties that oxidize | Manganese ions, reactive oxygen species |
| Hydrophobic moieties | Moieties that improve solubility in non-aqueous solution and/or improve adsorption on the skin within a hair follicle | Hydrocarbons, myristoylated compounds, silanes |
| Hydrophilic moieties | Moieties that are water-loving and prevent adsorption | PEG, PEO, PLGA |
| Agnostic moieties | Moieties that bind a target cell, structure, or protein of interest | Antibodies, peptides, proteins |
| Antagonistic moieties | Moieties that block the binding to a target of interest | Antibodies, peptides, proteins |
| Reactive moieties | Moieties that react with biological or non-biological components with a resulting change in structure on the target | Aldehydes |

Description of Target Tissues.

Topical and Dermatological Applications.

In some embodiments, target tissues for topical and dermatological applications include the surface of the skin, the epidermis and the dermis. Diseases or conditions suitable for treatment with topical and dermatological applications include acne, warts, fungal infections, psoriasis, scar removal, hair removal, hair growth, reduction of hypertrophic scars or keloids, skin inconsistencies (e.g. texture, color, tone, elasticity, hydration), and malignant or non-malignant skin tumors.

As used herein, the term "acne" includes acne vulgaris as well as other forms of acne and related cutaneous conditions, including acne aestivalis, acne conglobata, acne cosmetic, acne fulminans, acne keloidalisnuchae, acne mechanica, acne miliarisnecrotica, acne necrotica, chloracne, drug-induced acne, excoriated acne, halogen acne, lupus miliaris disseminates faciei, pomade acne, tar acne, and tropical acne.

Subdermal Applications.

In some embodiments, target tissues for subdermal applications include the adipose tissue and connective tissue below the integumentary system. Diseases or conditions suitable for treatment with subdermatological applications include wrinkles and tattoos. Other applications with photoactive particles (e.g., plasmonic nanoparticles) include skin rejuvenation and/or resurfacing, the removal or reduction of stretch marks and fat ablation.

In some embodiments, a specific region of the target tissue that can be treated with the photoactive particles (e.g., plasmonic nanoparticles) descried herein is a hair follicle, a sebaceous gland, a merocrine sweat gland, an apocrine sweat gland, or an arrector pili muscle, within which a specific domain is targeted. For example, the bulge region of the hair follicle is targeted. Because in one embodiment the nanoparticles are useful to thermally ablate hair follicle stem cells for hair removal, regions containing hair follicle stem cells are of particular interest for targeting. Thus, the target tissue region may include a stem cell niche, bulge, sebaceous gland, dermal papilla, cortex, cuticle, inner root sheath, outer root sheath, medulla, Huxley layer, Henle layer or arrector pili muscle. Each of these regions may contain cells, stem cells, basement membrane, extracellular matrix, growth factors, analytes, or other biologic components that mediate hair follicle rejuvenation. Disruption or destruction of these components would have a therapeutic effect, e.g. slow or stop the processes that mediate hair regrowth, prevent the secretion of sebum from the sebaceous gland, damage or deter tumor cells, reduce the appearance of wrinkles. Structures can also be targeted that are in close proximity to a desired target for ablation, especially when capable of conducting heat effectively.

Localization Domains.

In one embodiment, compositions containing nanoparticles (e.g., plasmonic or non-plasmonic nanoparticles) that preferentially localize to a domain of a target tissue region of a mammalian subject to whom the composition is administered.

Targeting Moieties.

In some embodiments, nanoparticles (e.g., plasmonic or non-plasmonic nanoparticles) can be engineered to selectively bind to a domain of the target tissue. For example, the nanoparticles are operably linked to the domain via a biologic moiety, in order to effectively target the nanoparticles to the target tissue domain. Preferably, the moiety contains a component of a stem cell, a progenitor cell, an extracellular matrix component, a basement membrane component, a hair shaft component, a follicular epithelial component, or a non-follicular epidermal component. Biological moieties include proteins such as cell surface receptors, glycoproteins or extracellular matrix proteins, as well as carbohydrates, analytes, or nucleic acids (DNA, RNA) as well as membrane components (lipid bilayer components, microsomes).

Delocalization Domains.

In some embodiments, nanoparticles (e.g., plasmonic or non-plasmonic nanoparticles) present in the composition preferentially delocalize away from a domain of a target tissue region. Delocalization domains include specific regions of a tissue into which nanoparticles do not substantially aggregate, or alternatively, are removed from the domain more effectively. The delocalization domain, according to several embodiments, is a non-follicular epidermis, dermis, a component of a hair follicle (e.g., a hair stem cell, a stem cell niche, a bulge, a sebaceous gland, a dermal papilla, a cortex, a cuticle, an inner root sheath, an outer root sheath, a medulla, a Huxley layer, a Henle layer, an arrector pili muscle), a hair follicle infundibulum, a sebaceous gland, a component of a sebaceous gland, a sebocyte, a component of a sebocyte, or sebum Energy Sources.

Provided herein are various embodiments of energy sources to, for example, apply to or otherwise activate the photoactive particles. These include, but are not limited to, surface plasmon resonance excitation sources (e.g., nonlinear excitation surface plasmon resonance sources), various light sources and optical sources. Various embodiments of light sources include a laser (ion laser, semiconductor laser, Q-switched laser, free-running laser, or fiber laser), light emitting diode, lamp, the sun, a fluorescent light source or an electroluminescent light source. In several embodiments, the energy source is capable of emitting radiation at a wavelength from about 100, 200, 300, 400, 500, 1000, 2000, 5000 nm to about 10,000 nm or more. The surface plasmon resonance excitation sources (e.g., nonlinear excitation surface plasmon resonance source) is capable of emitting electromagnetic radiation, ultrasound, thermal energy, electrical energy, magnetic energy, or electrostatic energy. For example, the energy is radiation at an intensity from about $0.00005$ mW/cm$^2$ to about 1000 TW/cm$^2$. The optimum intensity is chosen to induce high thermal gradients from plasmonic nanoparticles in regions from about 10 microns to hundreds of microns in the surrounding tissue, but has minimal residual effect on heating tissue in which particles do not reside within a radius of about 100 microns or more from the nanoparticle. In certain embodiments, a differential heat gradient between the target tissue region and other tissue regions (e.g., the skin) is greater than 2-fold, 3-fold, 5-fold, 10-fold, 15-fold, 20-fold, 50-fold, 100-fold, or greater than 100 fold. With respect to nonlinear embodiments, at resonance wavelengths plasmonic nanoparticles can act as antennas, providing a nonlinear excitation at peak resonance or, in other words, an enhanced extinction cross section for a given physical cross-section of material when compared to non-plasmonic photoactive materials of the same dimension. Thus, in several embodiments, plasmonic materials may be able to pull more energy from delocalized electromagnetic waves surrounding the material at peak resonance than non-plasmonic photoactive material of the same dimension.

The energy can be tuned by monitoring thermal heat gradients on the surface of the skin with a thermal/infrared camera. As demonstrated herein, the methods and systems of the present disclosure provide superior efficacy when a surface plasmon is generated on the nanoparticles by the action of the radiation. Typically, the plasmon is generated in a one-photon mode or, alternatively, a two-photon mode, a multi-photon mode, a step-wise mode, or an up-conversion mode.

Delivery of Radiation.

In some embodiments, physical means of delivery of the light energy (e.g., laser, flash lamp, intense pulse, etc.) to the surface plasmon resonance excitation (e.g., nonlinear excitation surface plasmon resonance source) to the target tissue region include a fiber, waveguide, a contact tip, a microlens array, a digital micromirror array (DMA), or a combination thereof.

In some embodiments, optical sources include a CW optical source or a pulsed optical source, which may be a single wavelength polarized (or, alternatively, unpolarized) optical source capable of emitting radiation at a frequency from about 200 nm to about 10,000 nm. Alternatively, the optical source is a multiple wavelength polarized (or, alternatively, unpolarized) optical source capable of emitting radiation at a wavelength from about 200 nm to about 10,000 nm. The pulsed optical source is generally capable of emitting pulsed radiation at a frequency from about 1 Hz to about 1 THz. The pulsed optical source is capable of a pulse less than a millisecond, microsecond, nanosecond, picoseconds, or femtosecond in duration. For example, a source emitting radiation at a wavelength of 755 nm is operated in pulse mode such that the emitted radiation is pulsed at a duration of 0.25-300 milliseconds (ms) per pulse, with a pulse frequency of 1-10 Hz. In another example, radiation emitted at a wavelength of 810 nm is pulsed at 5-100 ms with a frequency of 1-10 Hz. In a further example, a source emitting radiation at a wavelength of 1064 nm is pulsed at 0.25-300 ms at a frequency of 1-10 Hz. In yet another example, a source emitting intense pulsed light at a wavelength of 530-1200 nm is pulsed at 0.5-300 ms at a frequency of 1-10 Hz. The optical source may be coupled to a skin surface cooling device to reduce heating of particles or structures on the skin surface and focus heating to components within follicles or tissue structures at deeper layers. In some embodiments, pulse widths range from 0.1 ms to 1 m, 1 ms-10 ms, 10 ms-100 ms, 100 ms-1000 ms, greater than 1000 ms.

Nanoparticle-Containing Compositions.

In order to provide optimal dermal penetration into the target tissue, photoactive particles (e.g., plasmonic nanoparticles) in certain embodiments are formulated in various compositions. In one embodiment, the nanoparticles are formulated in compositions containing 1-10% v/v surfactants (e.g. sodium dodecyl sulfate, sodium laureth 2-sulfate, ammonium lauryl sulfate, sodium octech-1/deceth-1 sulfate). Surfactants disrupt and emulsify sebum or other hydrophobic fluids to enable improved targeting of hydrophilic nanoparticles to the hair follicle, infundibulum, sebaceous gland, or other regions of the skin. Surfactants also lower the free energy necessary to deliver hydrophilic nanoparticles into small hydrophobic crevices such as the space between the hair shaft and follicle or into the sebaceous gland. Nanoparticle-containing compositions may also include emulsions at various concentrations (1-20% w/v) in aqueous solutions, silicone/oil solvents, polypropylene gel, propylene glycol or creams (e.g. comprising alcohols, oils, paraffins, colloidal silicas). In other embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Alternatively, a matrix component such as silica, polystyrene or polyethylene glycol is provided in the formulation. Other formulations include components of surfactants, a lipid bilayer, a liposome, microsome, polymersomes, or a polymer microcapsules. A nanoparticle may comprise a larger micron-sized particle.

Effective Doses.

In various embodiments, an effective dose of the nanoparticle-containing compositions includes an amount of particles required, in some aspects, to generate an effective heat gradient in a target tissue region, such that a portion of the target tissue region is acted upon by thermal energy from excited nanoparticles. A "minimal effective dose" is the smallest number or lowest concentration of nanoparticles in a composition that are effective to achieve the desired biological, physical and/or therapeutic effect(s). In some embodiments, the photoactive particles (e.g., plasmonic nanoparticles) have an optical density of 10 O.D.-1,000 O.D. (e.g., 10-100 O.D, 50-200 O.D, 20-300 O.D.) at one or a plurality of peak resonance wavelengths.

Cosmetically Acceptable Carriers.

In some embodiments, provided are cosmetic or pharmaceutical compositions with a plurality of photoactive particles (e.g., plasmonic nanoparticles) and a cosmetically or pharmaceutically acceptable carrier. Generally, the carrier and composition must be suitable for topical administration to the skin of a mammalian subject, such that the photoactive particles (e.g., plasmonic nanoparticles) are present in an effective amount for selective thermomodulation of a component of the skin. In one embodiment, the nanoparticles are formulated with a carrier containing 1-10% v/v surfactants (e.g. sodium dodecyl sulfate, sodium laureth 2-sulfate, ammonium lauryl sulfate, sodium octech-1/deceth-1 sulfate) to enable disruption of the epidermal skin barrier, emulsify sebum, improve mixing of hydrophilic nanoparticles with hydrophobic solutions, and reduce entropic barriers to delivering hydrophilic particles to hydrophobic regions of the skin (e.g. between the hair shaft and surrounding sheath or follicle). In some embodiments, the carrier contains a polar or non-polar solvent. For example, suitable solvents include alcohols (e.g., n-Butanol, isopropanol, n-Propanol, Ethanol, Methanol), hydrocarbons (e.g., pentane, cyclopentane, hexane, cyclohexane, benzene, toluene, 1,4-Dioxane), chloroform, Diethyl-ether, water, water with propylene glycol, acids (e.g., acetic acid, formic acid), bases, acetone, isooctanes, dimethyl sulfoxide (DMSO), dimethylformamide (DMF), acetonitrile (MeCN), tetrahydrofuran (THF), dichloromethane (DCM), ethylacetate, tetramethylammonium hydroxide, isopropanol, and others. In other embodiments, a stabilizing agent such as antioxidants, preventing unwanted oxidation of materials, sequestrants, forming chelate complexes and inactivating traces of metal ions that would otherwise act as catalysts, emulsifiers, ionic or non-ionic surfactants, cholesterol or phospholipids, for stabilization of emulsions (e.g. egg yolk lecithin, sodium stearoyl-lactylate, sodium bis(2-ethylhexyl-sulfosuccinate (AOT)), ultraviolet stabilizers, protecting materials, especially plastics, from harmful effects of ultraviolet radiation is provided. In further embodiments, a composition with a cosmetically acceptable carrier is generated such that the nanoparticles are substantially in a suspension.

Other components are also optionally included, including an emulsion, polymer, hydrogel, matrix, lipid bilayer, liposome, microsome, polymersome, or polymer microcapsule. Additionally, inclusion of a detectable colorant (e.g., a pigment), a fragrance, a moisturizer, and/or a skin protectant is optional. In some examples, the formulation has a viscosity of above, below or within 0.1-10,000 (e.g., $5e^{-4} \times 10^3$, 1,000), as measured in millipascal-seconds (mPa·s).

In some embodiments, nanoparticle quantities per milliliter in a composition are subject to modification for specific binding and can range from $10^9$ to $10^{18}$ particles but generally about $10^{11}$ to $10^{13}$ nanoparticles per milliliter. Nanoparticle quantities per milliliter in a formulation are subject to modification for specific binding but generally up to about $10^{23}$ nanoparticles per milliliter. In certain embodiments wherein increased concentration of nanoparticles to a target region is desired, compositions contain particle concentrations with optical densities of 10 O.D.-1000 O.D. (e.g., 10-100 O.D, 50-200 O.D, 20-300 O.D.), or optical densities greater than 1,000 O.D. (e.g., 1,200-1,500, 2,000) In some embodiments these correspond to concentrations of about 0.1-10% w/w or more of nanoparticles.

In one embodiment, prior to application of nanoparticle formulations (e.g., photoactive nanoparticles, such as plasmonic nanoparticles), skin and hair follicles can be pretreated to increase the delivery of nanoparticles to a target region. In some embodiments, hair shafts are cut or removed via shaving, waxing, sugaring, cyanoacrylate surface peels, calcium thioglycolate treatment, or other techniques to remove the hair shaft and/or hair follicle plugs and create a void wherein nanoparticles can accumulate. Orifices of active or inactive follicles can be blocked by plugs formed of corneocytes and/or other material (e.g. cell debris, soot, hydrocarbons, cosmetics). In some embodiments pre-treatment with surface exfoliation including mechanical exfoliation (e.g., salt glow or microdermabrasion) and chemical exfoliation (e.g., enzymes, alphahydroxy acids, or betahydroxy acids) removes plugs from the orifice of follicles to increase the targeting of nanoparticle formulations to target regions within the hair follicle.

In some embodiments, the nanoparticle formulations (e.g., photoactive nanoparticles, such as plasmonic nanoparticles) are formulated for application by a sponge applicator, cloth applicator, direct contact via a hand or gloved hand, spray, aerosol, vacuum suction, high pressure air flow, or high pressure liquid flow, roller, brush, planar surface, semi-planar surface, wax, ultrasound and other sonic forces (e.g., low frequency ultrasound via a transducer, acoustic horn, or sonotrode), mechanical vibrations, physical manipulation, hair shaft manipulation (including pulling, massaging), physical force, electrophoresis, iontophoresis, thermal manipulation, and other treatments. In several embodiments of the invention, massage (e.g., hand massage, vibration, mechanical vibration) can be applied at frequencies of less than 1 kHz, 1 Hz-900 Hz, 5-500 Hz, 10-100 Hz, 1-80 Hz, 50-250 Hz, and any frequencies therein. In some embodiments, nanoparticle formulation treatments are performed alone, in combination, sequentially or repeated 1-24 times. In other embodiments, the nanoparticles (e.g., photoactive nanoparticles, such as plasmonic nanoparticles) are capable of selectively localizing to a first component of the skin, where physical massage or pressure, ultrasound, or heat increase the selective localization of the nanoparticles to this first component. Additionally, the nanoparticles are selectively removable from components of the skin other than the first component, such removal accomplished with acetone, alcohol, water, air, peeling of the skin, chemical peeling, waxing, or reduction of the plasmonic compound. Further, in some embodiments the nanoparticles have a coat layer to increase solubility of the nanoparticles in the carrier and/or reduce "stickiness" and accumulation in non-target areas. The subject matter described herein also provides embodiments in which at least a portion of an exterior surface of the nanoparticle is modified, such as to include a layer of a polymer, polar monomer, non-polar monomer, biologic compound, a metal (e.g., metallic thin film, metallic composite, metal oxide, or metallic salt), a dielectric, or a semiconductor. Alternatively, the exterior surface modification is polar, non-polar, charged, ionic, basic, acidic, reactive, hydrophobic, hydrophilic, agonistic, or antagonistic. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., hair follicle) and limit delivery to non-target region (e.g. dermis).

Penetration Means

In some embodiments, the compositions of the instant disclosure are topically administered. Provided herein are means to redistribute plasmonic particles and other compositions described herein from the skin surface to a component of dermal tissue including a hair follicle, a component of a hair follicle, a follicle infundibulum, a sebaceous gland, or a component of a sebaceous gland using high frequency ultrasound, low frequency ultrasound, massage, iontophoresis, high pressure air flow, high pressure liquid flow, vacuum, pre-treatment with Fractionated Photothermolysis laser or derm-abrasion, or a combination thereof. In several embodiments of the invention, low frequency ultrasound can be applied at frequencies of 1 kHz to 500 kHz, e.g., 1 kHz-100 kHz, 5 kHz-45 kHz, 20 kHz-50 kHz, 30 kHz-40 kHz, 30 kHz, 40 kHz, and any ranges or frequencies therein.) In several embodiments of the invention, massage (e.g., hand massage, vibration, mechanical vibration) can be applied at frequencies of less than 1 kHz, 1 Hz-900 Hz, 5-500 Hz, 10-100 Hz, 1-80 Hz, 50-250 Hz, and any frequencies therein.

In some embodiments, a delivery device 200 is used to deliver, distribute, redeliver, redistribute, penetrate, drive, disperse, direct, and/or enhance movement of a composition 100 to a target location. In some embodiments, the delivery device 200 is a mechanical vibration device. In some embodiments, the delivery device 200 is a mechanical vibration device configured for mechanical mixing. In one embodiment, a mechanical vibration device vibrates at frequencies of less than 1 kHz, 1 Hz-900 Hz, 5-500 Hz, 10-100 Hz, 1-80 Hz, 50-250 Hz, and any frequencies therein. In some embodiments a mechanical vibration device vibrates, laterally, longitudinally, or radially. In one embodiment, a mechanical vibration device vibrates longitudinally. In one embodiment, a mechanical vibration device vibrates horizontally. In one embodiment, a mechanical vibration device vibrates radially. In one embodiment, a mechanical vibration device vibrates with a mix of one or more motions, longitudinal, horizontal, and/or radial. In one embodiment, a mechanical vibration device vibrates longitudinally at 80 Hz. In one embodiment, the delivery device 200 is a mechanical vibration device with 80 Hz longitudinal vibration. In one embodiment, the delivery device 200 is a Vibraderm with 80 Hz longitudinal vibration, configured to deliver a composition 100 to a depth of 1000 microns.

In some embodiments, the delivery device 200 is an ultrasound device. In some embodiments, the delivery device 200 is an ultrasound device with focused ultrasound energy. In some embodiments, the delivery device 200 is an ultrasound device with unfocused ultrasound energy. In some embodiments, the delivery device 200 is an ultrasound device that produces cavitation. In some embodiments, the delivery device 200 is an ultrasound device with pulsed energy. In some embodiments, the delivery device 200 is an ultrasound device with non-pulsed energy. In some embodiments, the delivery device 200 is an ultrasound device with surface localized energy such as that which can be generated by a Sonotrode. A sonotrode may refer to an acoustic horn, acoustic waveguide, ultrasonic probe, or ultrasonic horn. A sonotrode consists of a metal shaft, rod, horn, cone, taper, barbell, wedge, or other shape capable of translating and/or augment the amplitude produced by a low frequency ultrasonic transducer. The main function of a sonotrode is to deliver ultrasonic energy from a transducer into a gas, liquid, solid or tissue. In some embodiments, delivery device 200 is a sonotrode that is attached to an ultrasonic transducer or a stack of ultrasonic transducers. In some embodiments, the sonotrode delivery device 200 is designed to operate at frequencies between 15 kHz-100 kHz, e.g., 15 kHz-85 kHz, 15 kHz-75 kHz, 15 kHz-65 kHz, 15 kHz-55 kHz, 15 kHz-45 kHz, 15 kHz-35 kHz, 15 kHz-25 kHz, 25 kHz-60 kHz, 20 kHz-60 kHz, 20 kHz-50 kHz, 20 kHz-40 kHz, and any frequencies therein. In some embodiments of delivery device 200, the sonotrode is used to deliver ultrasonic energy into the composition, tissue, and/or surface of the tissue or any combination of the composition, tissue, and surface of the tissue. In some embodiments of delivery device 200, the power and amplitude of the sonotrode generates acoustic cavitation in the surrounding medium (e.g., composition, tissue, and/or surface of the tissue or any combination of the composition, tissue, and surface of the tissue). In some embodiments of the delivery device 200, the action of sonotrode generates heat, mixing, jetting, and streaming at or near the surface of the sonotrode in the surrounding medium. In some embodiments of delivery device 200, the acoustic waveguide within the sonotrode may also produce evanescent waves responsible for localized effects in the surrounding medium. One or more of the actions of the sonotrode are responsible for driving the delivery of the composition into the targeted area of the skin. Localized surface effects of the sonotrode include cavitation, jetting, mixing, and streaming.

In some embodiments, the delivery device 200 is a high frequency ultrasound device. In some embodiments, the delivery device 200 is a low frequency ultrasound device. In several embodiments of the invention, low frequency ultrasound can be applied at frequencies of 1 kHz to 500 kHz, e.g., 1 kHz-100 kHz, 5 kHz-45 kHz, 20 kHz-50 kHz, 30 kHz-40 kHz, 30 kHz, 40 kHz, and any ranges or frequencies therein.) In one embodiment, the delivery device 200 operates at a frequency of 20-50 kHz and more specifically 32.4 kHz with an axial amplitude between 1 micron-30 microns, e.g., 1 micron-20 microns, 1 micron-15 microns, 5 microns-15 microns, 5 microns-12 microns, 7 microns, 8 microns, 9 microns, 10 microns, 11 microns, 12 microns,-15 microns and any range of axial amplitudes therein. In one embodiment, the delivery device 200 operates at a frequency of 32.4 kHz with an axial amplitude between 1 micron-20 microns and a radial amplitude between 0 microns-5 microns, e.g., 0 microns, 1 micron, 2 microns, 3 microns, 4 microns, 5 microns, and any radial amplitude therein. In one embodiment, the delivery device 200 operates at a frequency of 32.4 kHz with an axial amplitude between 1 micron-20 microns, radial amplitude between 0 microns-5 microns, and is driven by an ultrasonic transducer with powers between 3 W-20 W, e.g., with surface localized energy configured to induce cavitation, configured to deliver a composition 100 to a depth of at least 1500 microns.

In one embodiment, the delivery device 200 is a low frequency ultrasound device that operates at a frequency of 30-60 kHz non-pulsed ultrasound configured to induce cavitation. In one embodiment, the delivery device 200 is a low frequency ultrasound device that operates at a frequency of 30-60 kHz non-pulsed ultrasound configured to induce cavitation from an unfocused transducer. In one embodiment, the delivery device 200 is a low frequency ultrasound device that operates at a frequency of 36 kHz non-pulsed ultrasound with a second harmonic at 55 kHz configured to induce cavitation at depth of approximately 8 mm and 18 mm in water from the face of the unfocused transducer, operating at a power between 2 W-15 W, and configured to deliver a composition 100 to a depth of at least 1000 microns.

In some embodiments, the delivery device 200 is configured to deliver a composition 100 to a depth of 1-100 microns, 1-1000 microns, 1-1500 microns, 1-2000 microns, 1-3000 microns, 1-4000 microns, and/or 1-5000 microns. In some embodiments, the delivery device 200 is configured to deliver a composition 100 to a depth of 1000-1500 microns. In some embodiments, the delivery device 200 is configured to deliver a composition 100 to a depth of 1000 microns. In some embodiments, the delivery device 200 is configured to deliver a composition 100 to a depth of 1500 microns. In some embodiments, the delivery device 200 is configured to deliver a composition 100 to a depth of 2000 microns. In some embodiments, the delivery device 200 is configured to deliver a composition 100 to a depth of 2500 microns. In some embodiments, the nanoparticles described herein are formulated to penetrate much deeper—up to several centimeters, or into the panniculus adiposus (hypodermis) layer of subcutaneous tissue. For example, the compositions can be administered by use of a sponge applicator, cloth applicator, spray, aerosol, vacuum suction, high pressure air flow, high pressure liquid flow direct contact by hand ultrasound and other sonic forces, mechanical vibrations, physical manipulation, hair shaft manipulation (including pulling, massaging), physical force, thermal manipulation, or other treatments. Nanoparticle formulation treatments are performed alone, in combination, sequentially or repeated 1-24 times.

Specific Types of Applications

Non-limiting descriptions of certain applications are provided below. The nanoparticles described may be plasmonic or non-plasmonic. For example, non-plasmonic, photoactive nanoparticles may be used.

Acne Treatment

Acne is caused by a combination of diet, hormonal imbalance, bacterial infection (*Propionibacterium acnes*), genetic predisposition, and other factors. The nanoparticle-based methods and systems described herein for acne treatment are able to focally target causative regions of the dermis, the sebaceous gland and the hair follicle, and thus have advantages compared to the existing techniques known in the art, including chemical treatment (peroxides, hormones, antibiotics, retinoids, and anti-inflammatory compounds), dermabrasion, phototherapy (lasers, blue and red light treatment, or photodynamic treatment), or surgical procedures.

In particular, laser-based techniques are becoming an increasingly popular acne treatment, but a substantial limitation is the lack of selective absorptive properties among natural pigments (e.g. fat, sebum) for specific wavelengths of light such that selective heating of one cell, structure, or component of tissue, particularly in the sebaceous glands, infundibulum, and regions of the hair follicle, is not achieved without heating of adjacent off-target tissue. The nanoparticles described herein provide significantly higher photothermal conversion than natural pigments enabling laser energy to be focused to specific cells, structures, or components of tissue within the sebaceous gland, infundibulum, or regions of the hair follicle for selective photothermal damage.

Using the materials and techniques described herein may provide acne treatments of greater duration than existing methodologies. In certain embodiments, tuned selective ablation of the sebaceous gland or infundibulum is achieved as described herein. In particular, plasmonic nanoparticles are specifically localized to regions of hair follicles in or proximate to the sebaceous gland or infundibulum.

Plasmonic nanoparticles exhibit strong absorption at wavelengths emitted by standard laser hair removal devices (e.g., 755 nm, 810 nm, 1064 nm) and intense pulse light (IPL) devices (e.g., 515-1200 nm range) relative to surrounding epidermal tissue. Thus, irradiation of targeted plasmonic nanoparticles with laser light or IPL induces heat radiation from the particles to the adjacent sebum, sebaceous gland, infundibulum, and other acne causing agents.

Hair Removal

The nanoparticle-based methods and systems described herein for skin treatment have advantages compared to the existing techniques known in the art, including laser-based techniques, chemical techniques, electrolysis, electromagnetic wave techniques, and mechanical techniques (e.g., waxing, tweezers). Such techniques fail to adequately provide permanent hair removal across a breadth of subjects. In particular, subjects having light to medium-pigmented hair are not adequately served by these techniques, which suffer from side-effects including pain and the lack of beneficial cosmetic affects including hair removal. Laser-based techniques are popular in a variety of applications, but a substantial limitation is the lack of selective absorptive properties among natural pigments (e.g. melanin) for specific wavelengths of light such that selective heating of one cell, structure, or component of tissue is achieved without heating of adjacent off-target tissues. The nanoparticles described herein provide significantly higher photothermal conversion than natural pigments enabling laser energy to be focused to specific cells, structures, or components of tissue for selective photothermal damage. The methods described herein are useful for hair removal of all types and pigmentations. For example, melanin, the predominant hair pigment, is an aggregation of chemical moieties including eumelanin and phaeomelanin. Eumelanin colors hair grey, black, yellow, and brown. A small amount of black eumelanin in the absence of other pigments causes grey hair. Types of eumelanin include black eumelanin and brown eumelanin, with black melanin being darker than brown. Generally, black eumelanin predominates in non-European subjects and aged Europeans, while brown eumelanin is in greater abundance in young European subjects. Phaeomelanin predominates in red hair. In another example, vellus hair ("peach fuzz") is a type of short, fine, light-colored, and usually barely noticeable hair that develops on much or most of a subject's body (excluding lips, palms of hand, sole of foot, navel and scar tissue). While the density of vellus hair is generally lower than that of other hair types, there is variation from person to person in the density, thickness, and pigmentation. Vellus hair is usually less than 2 mm long and the follicle containing the vellus hair is generally not connected to a sebaceous gland. Conditions associated with an overabundance of vellus hair include Cushing's syndrome and anorexia nervosa, such overgrowth being treatable using the methods and compositions described herein. Further, provided are methods of targeting hair growth at a given stage. Hair grows in cycles of various stages or phases. Growth phase is termed "anagen", while "catagen" includes the involuting or regressing phase, and "telogen" encompasses the resting or quiescent phase. Each phase has several morphologically and histologically distinguishable subphases. Generally, up to 90% of the hair follicles on a subject are in anagen phase (10-14% are in telogen and 1-2% in catagen). The cycle's length is governed by cytokines and hormones, and varies on different parts of the body. For eyebrows, the cycle is completed in around 4 months, while it takes the scalp 3-4 years to finish. The methods and compositions described herein are sufficient to treat hair of all growth stages or phases.

More permanent reduction or removal of all hair types is provided herein, relative to hair removal treatments known in the art. In certain embodiments, tuned selective ablation of the hair shaft and destruction of stem cells in the bulge region is provided, as described herein. In particular, plasmonic nanoparticles are specifically localized to regions of hair follicles in or proximate to the bulge region, a stem cell-rich domain of the hair follicle. Moreover, the plasmonic nanoparticles are localized in close approximation of ~50-75% of the hair shaft structure.

Plasmonic nanoparticles exhibit strong absorption at wavelengths emitted by standard laser hair removal devices (e.g., 755 nm, 810 nm, 1064 nm) and intense pulse light (IPL) devices (e.g., 515-1200 nm range) relative to surrounding epidermal tissue. Thus, irradiation of targeted plasmonic nanoparticles with laser light induces heat radiation from the particles to the adjacent stem cells (or in some cases, the architecture of the hair shaft itself), resulting in cell death and a disruption of the normal regenerative pathway.

Non-Malignant and Malignant Skin Tumors

Laser therapies for the prevention and treatment of non-malignant, malignant, melanoma and non-melanoma skin cancers have been focused largely on photodynamic therapy approaches, whereby photosensitive porphyrins are applied to skin and used to localize laser light, produce reactive oxygen species and destroy cancer cells via toxic radicals. For example, 5-ALA combined with laser treatment has been FDA-approved for the treatment of non-melanoma skin cancer actinic keratoses, and it is used off-label for the treatment of widely disseminated, surgically untreatable, or recurrent basal cell carcinomas (BCC). However, this procedure causes patients to experiences photosensitivity, burning, peeling, scarring, hypo- and hyper-pigmentation and other side effects due to non-specific transdermal uptake of porphyrin molecules. The nanoparticles described herein provide significantly higher photothermal conversion than natural pigments and dyes, enabling laser energy to be focused to specific cells, structures, or components of tissue for selective thermomodulation Using the materials and techniques described herein may provide cancer treatments of greater degree and duration than existing methodologies. In certain embodiments, tuned selective ablation of specific target cells, such as Merkel cells or Langerhans cells, as described herein. In particular, plasmonic nanoparticles are specifically localized to regions of hair follicles where follicular bulge stem cells arise to form nodular basal cell carcinomas and other carcinomas. Plasmonic nanoparticles may also be delivered to other target cells that cause tumors, for example, the interfollicular epithelium, which include the cell of origin for superficial basal cell carcinomas.

Plasmonic nanoparticles exhibit strong absorption at wavelengths emitted by standard laser hair removal devices (e.g., 755 nm, 810 nm, 1064 nm) and intense pulse light (IPL) devices (e.g., 515-1200 nm range) relative to surrounding epidermal tissue. Thus, irradiation of targeted plasmonic nanoparticles with laser light induces heat radiation from the particles to the adjacent keratinocyte, melanocyte, follicular bulge stem cell, cancer cell, or cancer cell precursor, resulting in cell death or inhibited cell growth for cancer prevention and treatment.

Subdermal Applications.

Target tissues for subdermal applications include the adipose tissue and connective tissue below the integumentary system. Diseases or conditions suitable for treatment with subdermatological applications include wrinkles and tattoos. Other applications include skin rejuvenation and/or resurfacing, the removal or reduction of stretch marks and fat ablation.

Vascular Applications.

Target tissues for vascular applications include arteries, arterioles, capillaries, vascular endothelial cells, vascular smooth muscle cells, veins, and venules. Diseases or conditions suitable for treatment with vascular applications include spider veins, leaky valves, and vascular stenosis. In particular, vein abnormalities account for a substantial proportion of cosmetic diseases or conditions affecting the vasculature. Individuals with vein abnormalities such as spider veins or faulty venous valves suffer from pain, itchiness, or undesirable aesthetics.

Additionally, there are several indication for which ablation of other vessels including arteries, arterioles, or capillaries could provide therapeutic or cosmetic benefit including: 1) ablation of vasculature supplying fat pads and/or fat cells, 2) ablation of vasculature supporting tumors/cancer cells, 3) ablation of vascular birth marks (port-wine stains, hemangiomas, macular stains), and 4) any other indication whereby ablation of vessels mediates the destruction of tissue and apoptosis or necrosis of cells supported by those vessels with therapeutic or cosmetic benefit. Provided herein are methods for using the compositions described herein for the selective destruction of component(s) of veins from plasmonic nanoparticles focally or diffusely distributed in the blood. Plasmonic nanoparticles are combined with a pharmaceutically acceptable carrier as described above and are introduced into the body via intravenous injection. Nanoparticles diffuse into the blood and, in some embodiments, localize to specific vascular tissues. Subsequently, the nanoparticles are activated with laser or light-based systems as known in the art for treating skin conditions such as hair removal or spider vein ablation. Alternatively, image or non-image guided fiber optic waveguide-based laser or light systems may be used to ablate vessel or blood components in larger veins. In one embodiment, a device with dual functions for both injecting nanoparticles and administering light through on optical waveguide may be used. Activated nanoparticles heat blood and adjacent tissue (vessels, vessel walls, endothelial cells, components on or in endothelial cells, components comprising endothelial basement membrane, supporting mesenchymal tissues, cells, or cell components around the vessel, blood cells, blood cell components, other blood components) to ablative temperatures (38-50 degrees C. or higher).

Provided herein is a composition comprising a pharmaceutically acceptable carrier and a plurality of plasmonic nanoparticles in an amount effective to induce thermomodulation of a vascular or intravascular target tissue region with which the composition is intravenously contacted. Furthermore, the composition of plasmonic nanoparticle may comprise a microvascular targeting means selected from the group consisting of anti-microvascular endothelial cell antibodies and ligands for microvascular endothelial cell surface receptors. Also provided is a method for performing thermoablation of a target vascular tissue in a mammalian subject, comprising the steps of contacting a region of the target vascular tissue with a composition comprising a plurality of plasmonic nanoparticles and a pharmaceutically acceptable carrier under conditions such that an effective amount of the plasmonic nanoparticles localize to a domain of the target vascular region; and exposing the target tissue region to energy delivered from a surface plasmon resonance excitation sources (e.g., nonlinear excitation surface plasmon resonance source) in an amount effective to induce thermoablation of the domain of the target vascular region.

Oral and Nasal Applications.

Target tissues for oral applications include the mouth, nose, pharynx, larynx, and trachea. Diseases or conditions suitable for treatment with vascular applications include oral cancer, polyps, throat cancer, nasal cancer, and Mounier-Kuhn syndrome. Other conditions suitable for treatment include allergies or voice disorders involving vocal chords.

Endoscopic Applications.

Target tissues for endoscopic applications include the stomach, small intestine, large intestine, rectum and anus. Diseases or conditions suitable for treatment with vascular applications include gastrointestinal cancer, ulcerative colitis, Crohn's disease, Irritable Bowel Syndrome, Celiac Disease, Short Bowel Sydrome, or an infectious disease such as giardiasis, tropical sprue, tapeworm infection, ascariasis, enteritis, ulcers, Whipple's disease, and megacolon.

Methods of Thermomodulation.

Provided are embodiments of methods for performing thermomodulation of a target tissue region. A nanoparticle composition comprising a plurality of plasmonic nanoparticles under conditions such that an effective amount of the plasmonic nanoparticles localize to a domain of the target tissue region; and exposing the target tissue region to energy delivered from a surface plasmon resonance excitation sources (e.g., nonlinear excitation surface plasmon resonance source) in an amount effective to induce thermomodulation of the domain of the target tissue region.

Removal of Non-Specifically Bound Nanoparticles.

In various embodiments, removing nanoparticles localized on the surface of the skin may be performed by contacting the skin with acetone, alcohol, water, air, a debriding agent, or wax. Alternatively, physical debridement may be performed. Alternatively, one can perform a reduction of the plasmonic or other compound.

Amount of Energy Provided.

In some embodiments, skin is irradiated at a fluence of 1-60 Joules per $cm^2$ with laser wavelengths of about, e.g., 750 nm, 810 nm, 1064 nm, or other wavelengths, particularly in the range of infrared light. Various repetition rates are used from continuous to pulsed, e.g., at 1-10 Hz, 10-100 Hz, 100-1000 Hz. While some energy is reflected, it is an advantage of the subject matter described herein is that a substantial amount of energy is absorbed by particles, with a lesser amount absorbed by skin. Nanoparticles are delivered to the hair follicle, infundibulum, or sebaceous gland at concentration sufficient to absorb, e.g., 1.1-100× more energy than other components of the skin of similar volume. This is achieved in some embodiments by having a concentration of particles in the hair follicle with absorbance at the laser peak of 1.1-100× relative to other skin components of similar volume.

To enable tunable destruction of target skin structures (e.g., sebaceous glands, infundibulum, hair follicles), some embodiments of light-absorbing nanoparticles are utilized in conjunction with a laser or other excitation source of the appropriate wavelength. The laser light may be applied continuously or in pulses with a single or multiple pulses of light. The intensity of heating and distance over which photothermal damage will occur are controlled by the intensity and duration of light exposure. In some embodiments, pulsed lasers are utilized in order to provide localized thermal destruction. In some such embodiments, pulses of varying durations are provided to localize thermal damage regions to within 0.05, 0.1, 0.5, 1, 2, 5, 10, 20, 30, 50, 75, 100, 200, 300, 500, 1000 microns of the particles. Pulses are at least femtoseconds, picoseconds, microseconds, or milliseconds in duration. In some embodiments, the peak temperature realized in tissue from nanoparticle heating is at least 5, 10, 15, 20, 25, 30, 40, 50, 60, 70, 80, 90, 100, 200, 300, or 500 degrees Celsius. In some embodiments that utilize pulsed heating, high peak temperatures are realized locally within the hair shaft without raising the macroscopic tissue temperature more than 0.1, 0.5, 1, 2, 3, 4, 5, 7, 9, 12, 15, or 20 degrees Celsius. In some embodiments short pulses (100 nanoseconds-1000 microseconds) are used to drive very high transient heat gradients in and around the target skin structure (e.g., sebaceous gland and/or hair follicle) from embedded particles to localize damage in close proximity to particle location. In other embodiments, longer pulse lengths (1-10 ms, or 1-500 ms) are used to drive heat gradients further from the target structure to localize thermal energy to stem cells in the bulge region or other components greater than 100 μm away from the localized particles. Fluences of 1-10 Joules per $cm^2$ or 1-30 Joules per $cm^2$ are generally sufficient to thermally ablate follicles that have high particle concentrations and thus higher absorbance than skin (e.g., 1.1-100 times per volume absorbance of skin). These fluences are often lower than what is currently employed (e.g., Diode: 25-40 $J/cm^2$, Alexandrite: 20 J/cm2, Nd:YAG: 30-60 $J/cm^2$) and lead to less damage to non-follicular regions, and potentially less pain.

Plasmon Resonance Systems.

Provided are embodiments of plasmon resonance systems containing a surface that includes a plurality of plasmonic nanoparticles, and a nonlinear excitation source. Optionally, the system contains a means to generate thermal heating of the surface. Preferably, the surface is a component of skin that is targeted for cosmetic or therapeutic treatment (e.g., bulge region for hair removal, infundibulum or sebaceous gland for acne prevention). Also provided as a component of the system is a means for delivering plasmonic nanoparticles to the skin surface, such as an applicator, a spray, an aerosol, vacuum suction, high pressure air flow, or high pressure liquid flow. Further provided are means of localizing plasmonic nanoparticles to a component of the skin (e.g., hair follicle, bulge region, sebaceous gland, infundibulum). Useful surface delivery means include a device that generates high frequency ultrasound, low frequency ultrasound, heat, massage, contact pressure, or a combination thereof. In several embodiments of the invention, low frequency ultrasound can be applied at frequencies of 1 kHz to 500 kHz, e.g., 1 kHz-100 kHz, 5 kHz-45 kHz, 20 kHz-50 kHz, 30 kHz-40 kHz, 30 kHz, 40 kHz, and any ranges or frequencies therein.) In several embodiments of the invention, massage (e.g., hand massage, vibration, mechanical vibration) can be applied at frequencies of less than 1 kHz, 1 Hz-900 Hz, 5-500 Hz, 10-100 Hz, 1-80 Hz, 50-250 Hz, and any frequencies therein.

Further provided are systems that contain a removal means for removing nanoparticles on a non-follicular portion of the skin. The removal means includes at least one of acetone, alcohol, water, air, chemical peeling, wax, or a compound that reduces the plasmonic compound.

In addition, the systems of the present disclosure provide nonlinear excitation source that generates a continuous wave optical source or a pulsed optical source. Alternatively, the nonlinear excitation source is capable of generating electromagnetic radiation, ultrasound, thermal energy, electrical energy, magnetic energy, or electrostatic energy. Provided are systems wherein the nonlinear excitation source is capable of irradiating the nanoparticles with an intensity from about 0.00005 $mW/cm^2$ to about 1000 $TW/cm^2$. Further, the nonlinear excitation source is capable of functioning in a one-photon mode, two-photon mode, multi-photon mode, step-wise mode, or up-conversion mode. A fiber, a waveguide, a contact tip, or a combination thereof may be used in the instant systems.

In some embodiments, the system contains a monitoring device such as a temperature sensor or a thermal energy detector. In other embodiments, the systems also contain a controller means for modulating the nonlinear excitation source (e.g., a "feedback loop controller"). In a related embodiment, the system contains a means for detecting a temperature of the surface or a target tissue adjacent to the surface, wherein the controller means modulates the intensity of the nonlinear excitation source and/or the duration of the excitation. In such embodiments, the controller means preferably modulates the intensity of the nonlinear excitation source such that a first component of the hair follicle is selectively thermoablated relative to a second component of the hair follicle. In further embodiments, a cooling device is directly contacted with the skin during irradiation to minimize the heating of nanoparticles or skin at the surface, while nanoparticles that have penetrate more deeply into the follicle, skin, or sebaceous gland heat to temperatures that selectively ablate the adjacent tissues.

Skin is one embodiment of a target tissue. The skin preferably contains a hair follicle and/or a sebaceous gland, where the nonlinear excitation source generates energy that results in heating the skin in an amount effective to induce thermomodulation of a hair follicle, a infundibulum, a sebaceous gland, or a component thereof, such as by heating sufficient to cause the temperature of the skin to exceed 37° C., such as 38° C., 39° C., 40° C., 41° C., 42° C., 43° C., 44° C., 45° C., 46° C., 47° C., 48° C., 49° C., to about 50° C. or greater.

Methods of Formulation.

In some embodiments, methods for formulating the nanoparticles of the present disclosure into a form suitable for use are described herein. In one embodiment, the nanoparticle compositions are generated by:
a) forming a first mixture containing a plurality of nanoparticles and a first solvent;
b) exchanging the first solvent for a second solvent to form a second mixture; and
c) combining the second mixture and a cosmetically or pharmaceutically acceptable carrier; thereby forming a nanoparticle composition.

The exchanging step is optionally performed using liquid chromatography, a solvent exchange system, a centrifuge, precipitation, or dialysis. Preferably, the nanoparticles are surface modified through a controlled reduction step or an oxidation step. Such surface modification may involve a coating step, such as the adsorbance of a monomer, polymer, or biological entity to a surface of the nanoparticle. Typically, the coating step involves contacting the nanoparticles with an oxidative environment. Further, the coating step may include monomer polymerization to create polymer coat.

In one embodiment, the methods described herein may also include the steps of dissolving the nanoparticles in a non-polar solvent and subsequently mixing the dissolved nanoparticles with a polar solvent so as to encapsulate the nanoparticles in an emulsion. Further, the addition of surfactants (e.g. sodium dodecyl sulfate, sodium laureth 2-sulfate, ammonium lauryl sulfate, sodium octech-1/deceth-1 sulfate) at concentrations of 0.1-10% may be used to disrupt the epidermal skin barrier, emulsify the sebum and enable improved mixing of hydrophilic nanoparticles in aqueous solutions. Further, a concentration of the nanoparticles such as centrifugation or lyophilization may be employed. Further, the nanoparticles may be pretreated with heat or radiation. Also provided is the optional step of conjugating a biological entity or plurality of biological entities to the nanoparticles. Such a conjugating step may involve a thiol, amine, or carboxyl linkage of the biological entities to the nanoparticles.

Diseases and Disorders.

Several embodiments of the present disclosure can be used on human (or other animal) skin for the treatment of wrinkles and other changes related to photo-aging or chronologic aging (generally termed skin rejuvenation), for the treatment of diseases including skin diseases, for the reduction of acne and related disorders such as rosacea, folliculitis, pseudofolliculitis barbae or proliferative or papulosquamous disorders such as psoriasis, for the stimulation or reduction of hair growth, and for reduction of cellulite, warts, hypopigmentation such as port-wine stain (PWS; nevus flammeus), birthmarks, hyperhidrosis, varicose veins, pigment problems, tattoos, vitiligo, melasma, scars, stretch marks, fungal infections, bacterial infections, dermatological inflammatory disorders, musculoskeletal problems (for example, tendonitis or arthritis), to improve healing of surgical wounds, burn therapy to improve healing and/or reduce and minimize scarring, improving circulation within the skin, and the like.

Several embodiments of the present disclosure can also be useful in improving wound healing, including but not limited to chronic skin ulcers, diabetic ulcers, gastric ulcers, thermal burn injuries, viral ulcers or disorders, periodontal disease and other dental disease. The present disclosure can be useful in treating the pancreas in diabetes. The present disclosure can be useful for in vitro fertilization enhancement, and the like. The present disclosure, in certain embodiments, is also useful in enhancing the effects of devices that create an injury or wound in the process of performing cosmetic surgery including non-ablative thermal wounding techniques for treating skin wrinkles, scars, stretch marks and other skin disorders. Under such circumstances, it may be preferable to use conventional non-ablative thermal treatments in combination with the methods of the present disclosure. The instant application, in certain embodiments, are used in conjunction with micro- or surface abrasion, dermabrasion, or enzymatic or chemical peeling of the skin or topical cosmeceutical applications, with or without nanoparticle application to enhance treatment, as the removal of the stratum corneum (and possibly additional epithelial layers) can prove beneficial for some treatment regimen. The methods of the present disclosure are particularly applicable to, but are not limited to, acne treatment, hair removal, hair growth/hair follicle stimulation, reduction/prevention of malignant and non-malignant skin tumors, and skin rejuvenation, as described herein.

The dermatologically therapeutic methods described herein may be formed using nanoparticle irradiation alone, nanoparticle irradiation in combination with nano- or microparticles, or nanoparticle irradiation with a composition comprising nano- or microparticles and one or more therapeutic agents. Such nanoparticle irradiation may be produced by any known nanoparticle generator, and is preferably a focused nanoparticle generator capable of generating and irradiating focused nanoparticle waves. Additionally, nanoparticle waves can be focused in tissues to provide damage to local areas with a desirable size and shape.

Several embodiments of the invention describe the development and utilization of compositions containing photoactive materials (e.g., nanoparticles and other materials) for the treatment of small target regions of skin including acne scars and other skin conditions. In some embodiments, such compositions are generally applied topically, through an apparatus that provides the composition in a form suitable for contact with and retention at a target region of skin in a manner that encompasses irradiating the skin with light (e.g., electromagnetic radiation) having a wavelength sufficient to ablate or otherwise damage the target region of skin and cause remodeling of the skin tissue. Without being bound by theory, it is believed that the damage to the skin resulting from heat transfer from the photoactive material after interaction with the radiation induces a wound healing response, including new extracellular matrix (e.g., collagen) production and remodeling, neovascularization, and epidermal normalization. As provided herein, "thermal injury" encompasses cell death in one or more regions of the dermal tissue of interest ("lethal damage"), or stimulation of the release of cytokines, heat shock proteins, and other wound healing factors without stimulating necrotic cell death ("sub-lethal damage").

In one embodiment, provided are methods for reducing dermal scar tissue, typically in order to improve the appearance of the skin tissue containing the scar, in a human subject using photoactive materials. While humans are provided as one example of mammalian subjects, one of skill in the art would recognize that other mammals are suitable for treatment herewith.

Typical dermal scar tissue can result from acne infection or other acute or chronic damage or injuries, such as burns, puncture or abrasive injury, surgery, or from conditions caused by environmental conditions or inherited genetic aberrations.

While scars are three dimensional in nature, description of the epidermal surface of the scar on the surrounding skin tissue can be accomplished by provision of a depth, length and a width of the scar, each of which may be, e.g., less than about 1 mm, or about 2, 3, 4, 5, 6, 7, 8, 9, 10 mm or greater than 10 mm, or provision of the surface area encompassed by the scar, e.g., under about 5 mm$^2$, such as about 10 mm$^2$, 15 mm$^2$, 20 mm$^2$, 25 mm$^2$, 30 mm$^2$, 35 mm$^2$, 40 mm$^2$, 45 mm$^2$, 50 mm$^2$, or greater than about 50 mm$^2$. Dermal scars generally have a non-uniform depth, and are generally described as extending from the epidermal layer into the dermis, and optionally through the dermis. Typically, an acne scar on the chin, cheek, forehead or other facial area is at least 0.01 mm, 0.25 mm, 0.50 mm, 1 mm, 2 mm, 3 mm, 4 mm, or 5 mm in median thickness, or any thickness in the range of 0.01 mm to 5 mm.

Skin Tissue.

In preferred embodiments, a region of skin tissue on a human subject, herein a "target region", is subjected to the methods provided herein. Optionally, more than one target region is treated during a treatment regimen, and such treatment regimens may happen once, or more than once, e.g., once or several times per month, once or several times per week, once or several times per day, within hours or within less than one hour. A target region contains an epidermal surface, which contains the skin feature to be treated, such as an acne scar or other dermal scar tissue (also termed a "lesion" herein). The scar tissue may be newly present (e.g., within days, weeks, or a few months of formation following the damage or injury) or may be of longer duration (e.g., several months, or years). In some embodiments, a "small target region" is treated, meaning a dermal scar region that does not exceed 25 mm$^2$, and or does not have a longest surface dimension greater than 5 mm; such small target regions are generally located on the face or neck after acne vulgaris infection, or one of many inflammatory diseases such as chicken pox or small pox. Small target regions of dermal scars may be atrophic, hypertrophic, keloidal, or may lay largely within the planar surface of the skin, but have irregular texture, contour, or edges, in various embodiments, small target regions of dermal scars are termed rolling scars, ice-pick scars, and box-car scars.

Photoactive Materials.

Photoactive materials, particles or nanoparticles (also termed "photoresponsive" materials and "photoabsorbable" materials) include chromophores and plasmonic nanoparticles. A chromophore is able to selectively absorb a chosen wavelength of light thereby enhancing the effectiveness of the irradiation, such as laser light.

In one embodiment, photoactive materials include plasmonic nanoparticles with a nanoparticular metallic structure within which localized surface plasmons are excited by light. These surface plasmons are surface electromagnetic waves that propagate in a direction parallel to the metal/dielectric interface (e.g., metal/air or metal/water). At resonance wavelengths plasmonic nanoparticles are non-linear absorbers of energy, whereby both incident light energy and energy from light not directly incident on the particle is coupled to and absorbed by the particle. In various embodiments, nanoparticle compositions, and formulations containing nanoparticle compositions, contain from about $10^9$ to about $10^{16}$ nanoparticles per ml, such as $10^9$, $10^{10}$, $10^{11}$, $10^{12}$, $10^{13}$, $10^{14}$, $10^{15}$, or $10^{16}$ particles. In one embodiment, the compositions contain a sufficient concentration of particles so that the amount of particles localized to an effective 0.01-0.05 ml treatment volumes is from $10^7$ to $10^{13}$. In certain embodiments wherein increased concentration of nanoparticles to a target region is desired, compositions contain particle concentrations with optical densities (O.D.) of 10 O.D.-1,000 O.D., or optical densities greater than 1,000 O.D. In some embodiments these correspond to concentrations of about 0.01-10% w/w or more of nanoparticles.

Nanoparticles may be homogenous or heterogeneous in size and other characteristics. In certain embodiments where optimal plasmonic resonance is desired, a particle size in the range of from about 10 nm to about 200 nm is provided. Alternatively, in embodiments where enhanced penetration of the nanoparticles into a target tissue region such as a scar is desired, a particle size in the range of from about 200 nm to about 1000 nm is provided. Modulation of particle size present in the composition is also a useful means of concentrating the composition in a target domain. Further, as described herein, nanoparticles having a size range of from about 10 nm to about 100 nm can be used as component of a larger molecular structure, generally in the range of from about 100 nm to about 1000 nm or more. For example, photoactive particles, such as plasmonic nanoparticles, can be surface coated to increase its size, embedded into an acceptable carrier, or it can be cross-linked or aggregated to other particles, or to other materials, that generate a larger particle. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., scar tissue) and limit delivery to non-target region (e.g. surrounding non-scar epidermis).

Composition of Particles.

In various embodiments, the photoactive particle (e.g., nanoparticle) is a metal (e.g., gold, silver), metallic composite (e.g., silver and silica, gold and silica), metal oxide (e.g. iron oxide, titanium oxide), metallic salt (e.g., potassium oxalate, strontium chloride), intermetallic (e.g., titanium aluminide, alnico), electric conductor (e.g., copper, aluminum), electric superconductor (e.g., yttrium barium copper oxide, bismuth strontium calcium copper oxide), electric semiconductor (e.g., silicon, germanium), dielectric (e.g., silica, plastic), and/or a quantum dot (e.g., zinc sulfide, cadmium selenium). In non-limiting examples, the materials are gold, silver, nickel, copper, platinum, titanium, palladium, silicon, galadium, including any alloys, composites, and amalgams of these metals. Alternatively, the nanoparticle contains a composite including a metal and a dielectric, a metal and a semiconductor, or a metal, semiconductor and dielectric.

In one embodiment, the composition contains coated particles (e.g., nanoparticles). Such coatings include a biorecognitive such as an antibody, a bioactive moiety such as a protein, or a biological material that is sourced from living matter. In one embodiment the composition contains an insulator such as silicon, or a thin metal coating such as gold, silver, nickel, platinum, titanium, or palladium. The composition may contain a peptide, a nucleic acid, a protein, or an antibody, or may contain charged moieties, whereby those charges mediate enhanced or diminished binding to the target skin.

Optical Absorption.

In several embodiments, particles have optical absorption qualities of about 10 nm to about 10,000 nm, e.g., 200-700 nm, 700-1200 nm. In specific embodiments, the particles have optical absorption useful to excitation by standard laser devices or other light sources. For example, in some embodiments, particles absorb at wavelengths of about 755 nm (alexandrite lasers), in the range of about 800-810 nm (diode lasers), or about 1064 nm (Nd:YAG lasers). Similarly, in some embodiments, the particles absorb intense pulsed light (IPL), e.g., at a range of about 500 nm to about 1200 nm Other chromophores can be useful in the present invention. The term "chromophore" shall be given its ordinary meaning and shall also include compounds having chromophoric groups such as nitro groups, azo, alkylene units, esters, carbonyl groups, aldehydes, alkynes, aromatic rings, heterocyclics, carboxylic acids and the like. Photoactive materials function as therapeutic or cytotoxic agents upon irradiation but are substantially inert prior to irradiation. A photoactive material may be a substance (solid, liquid, or gas) that has color or imparts a color to the intact nanoparticles or microparticles (including when the substance itself lacks color, for example, a clear gas, but scatters electromagnetic waves, for example, light, and thus may appear colored, for example, white, blue, green, or yellow, depending on its scattering properties) under some conditions, for example, all of the time or after exposure to a certain wavelength (such as in a fluorescent substance). For example, a chromophore can be a fluorescent, phosphorescent, wavelength up-converting, or other substance that may normally be substantially invisible, but that emits ultraviolet, visible, or infrared wavelengths during and/or after exposure to wavelengths from a particular region of the electromagnetic spectrum. A chromophore can also be a substance that reversibly or irreversibly changes color spontaneously or in response to any stimulus. The chromophore can be or include rifampin, β-carotene, tetracycline, indocyanine green, India ink, Evan's blue, methylene blue, FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), or FD&C Yellow No. 6 (Sunset Yellow FCF). The chromophore can be any colored substance approved by the United States Food and Drug Administration for use in humans. In certain embodiments, the chromophore can be detected by the naked eye under normal lighting conditions or when exposed to UV, near-UV, IR, or near-IR radiation.

In various embodiments, photoactive particle (e.g., chromophores) may be provided as a microparticle or a nanoparticle. As used herein, a microparticle may be a particle of a relatively small size, not necessarily in the micron size range; the term is used in reference to particles of sizes that can be implanted to form tissue markings and thus can be less than 50 nm to 100 microns or greater. A micro- or nanoparticle may be of composite construction and is not necessarily a pure substance; it may be spherical or any other shape. Microparticles include, but are not limited to, (i) an indispersible, biologically inert coating, (ii) a core enveloped within the coating, wherein the core includes the chromophore which is detectable through the coating and is dispersible in the tissue upon release from the microparticle, and, optionally, (iii) an absorption component that absorbs the specific energy and that is located in the coating or the core, or both; and the specific property is the absorption of the specific energy to rupture the microparticle, releasing the chromophore which disperses in the tissue, thereby changing or removing, or both, the detectable marking, wherein the coating, the core, or the optional absorption component, or any combination thereof, provides the specific property.

In various embodiments, chromophores can be made from any appropriate solid, liquid, or gaseous material that has chromophoric properties. In general, useful chromophores include stains, dyes, colored drugs and proteins, and other materials. In many embodiments, chromophores are biologically inert and/or non-toxic (ideally they are non-carcinogenic, non-allergenic, and non-immunogenic) such as those approved by the FDA for use within the body.

In various embodiments, chromophores may be mixed in combinations before or after optional encapsulation, so that it may only be necessary to select a small number of different chromophores to obtain a broad range of colors for various tissue marking purposes. For example, the pure chromophores can be encapsulated separately and afterwards different colors may be mixed to form intermediate colors and shades (yellow microparticles may be mixed with blue microparticles to form a green mixture). Combinations of two or more unreactive chromophores can be mixed to form desired colors and shades, and then encapsulated to form microparticles. Optionally, pure chromophores may be separately encapsulated to form sub-microparticles, and then different colored sub-microparticles can be mixed together (or with unencapsulated chromophores) to form desired colors and shades. The mixture can then be encapsulated in coating to form a microparticle having a perceived color resulting from the blend of the differently colored chromophores.

In various embodiments, useful dispersible chromophores include, but are not limited to: drugs and dyes such as rifampin (red), β-carotene (orange), tetracycline (yellow), indocyanine green (such as Cardio-Green™), India ink, Evan's blue, methylene blue; soluble inorganic salts such as copper sulfate (green or blue), $Cu(NH_3)_2^{2+}$ (dark blue), $MnO_4$ (purple), $NiCl_2$ (green), $CrO_4$ (yellow), $Cr_2O_7^{2-}$ (orange); proteins such as rhodopsin (purple and yellow forms) and green fluorescent protein (fluoresces green under blue light); and any of the Food and Drug Administration (FDA) approved dyes used commonly in foods, pharmaceutical preparations, medical devices, or cosmetics, such as the well-characterized non-toxic sodium salts FD&C Blue No. 1 (Brilliant Blue FCF), FD&C Green No. 3 (Fast Green FCF), FD&C Red No. 3 (Erythrosine), FD&C Red No. 40 (ALLURA™ Red AC), FD&C Yellow No. 5 (Tartrazine), and FD&C Yellow No. 6 (Sunset Yellow FCF). Of these FD&C dyes, Yellow No. 5 is known to produce occasional allergic reactions. Additional FDA approved dyes and colored drugs are described in the Code of Federal Regulations (CFR) for Food and Drugs (see Title 21 of CFR chapter 1, parts 1-99).

In various embodiments, dispersible chromophore nanoparticles can be made from certain inert, normally indispersible colored substances that have been reduced to nanoparticles about 50 nm and smaller (e.g., 0.1-5 nm, 5-25 nm, 25-50 nm, and overlapping ranges therein). Although diffuse nanoparticles might have different optical properties from the macroscopic material, when concentrated within the confined space of a microparticle core (that is, nanoparticles are closer together than the wavelength of visible light, about 500 nm), they act as a single light scatterer and/or absorber, and thus have the appearance of the original indispersible material from which they are derived. Useful dispersible chromophore nanoparticles may be made from graphite, iron oxides, and other materials with small particle size, for example, less than 50 nm, less than 5 nm, etc.

In some embodiments, like the coating material, chromophores can be a material, or can include specific absorption components, which strongly absorbs radiation of specific wavelength(s), particularly in the near-infrared spectral region from about 800 to 1800 nm. Absorption properties of the chromophore or specific absorption component allow the microparticle core to be selectively heated by pulses of near-infrared radiation, thus rupturing the microparticle and releasing the previously encapsulated chromophores.

Visibly colored near-infrared absorbing materials can be used as the chromophore(s) (to provide the desired detectable color) or as specific absorption component(s) in conjunction with another chromophore (to contribute to the detectable color, if desired). The infrared-absorbing visible chromophore should be rendered invisible upon exposure of the microparticles to the radiation, for example, through dispersal. Examples of useful colored near-infrared absorbing materials include, but are not limited to, graphite and amorphous forms of carbon (black), iron oxides (black or red), silicon (black), germanium (dark gray), cyanine dyes (including indocyanine green and other colors), phthalocyanine dyes (green-blue), and pyrylium dyes (multiple colors). See also U.S. Pat. No. 5,409,797, herein incorporated by reference.

Near-infrared absorbing materials used as specific absorption component(s) can also be visibly transparent or nearly transparent at the concentrations and sizes used within the microparticles so that they do not affect the perceived color of the microparticle or of the tissue after microparticle disruption even if the material is indispersible. Useful examples include particles of filter glass (such as those manufactured by Schott, Inc.) and plastics such as polymethylmethacrylate (PMMA), as well as low concentrations of nanoparticulate graphite or other carbon. These materials can be mixed with chromophores having a desired color and then encapsulated.

In various embodiments, materials with other properties (such as absorption of ultraviolet, visible, microwave, radio wave and other wavelengths) can also be used to construct the photoactive materials. For example, visible materials can be incorporated into the microparticles as chromophores, or as specific absorption components within the chromophore or coating material. Then visible radiation can be applied to rupture the microparticles. Useful materials include, but are not limited to, all of the visible colored dispersible chromophores listed above and other materials rendered invisible upon exposure of the microparticles to the visible radiation, for example, Oil Nile Blue N dyes, fluorescein dyes, porphyrin dyes, and coumarin dyes.

In another embodiment, chromophores can be materials that are rendered invisible (or whose color changes) upon exposure of the microparticles to specific electromagnetic radiation without necessarily rupturing the microparticle. Bleachable chromophores (which react with a bleaching agent released by the radiation), photobleachable chromophores (altered by the radiation) or thermolabile chromophores (altered by heat produced by radiation absorption) may be used. Most of the chromophores listed above are suitable, because they can be oxidized and rendered invisible by bleaching agents, for example, peroxides, hypochlorites (such as sodium hypochlorite, or household bleach), excited oxygen species, or free radicals. For example, a microparticle can be constructed with core chromophore FD&C Red No. 40 and sub-microparticle(s) 90 containing sodium hypochlorite as the bleaching agent, which is released upon exposure of the microparticle to specific electromagnetic radiation. The chromophore FD&C Red No. 40 is rendered invisible upon exposure of the microparticle to this radiation and mixing with the bleach. Bleachable chromophores, which are pH-sensitive can also be used, because they can be rendered invisible if the pH within the microparticle is changed. For example, a microparticle can be constructed with core chromophore phenolphthalein (pink to red above pH 9) in a basic alcohol solution and sub-microparticle(s) 90 containing hydrochloric acid as bleaching agent 100 which is released upon exposure of the microparticle to specific electromagnetic radiation. The chromophore phenolphthalein is rendered invisible upon exposure of the microparticle to this radiation because of reduction in pH within the microparticle.

Photobleachable chromophores that are colored until they are rendered invisible by exposure to a specific type, wavelength, and/or intensity of electromagnetic radiation include, but are not limited to, phthalocyanine (such as the zinc or chloroaluminum complexes which are green or blue); porphycenes which can be green or purple; chlorin which is a chlorophyll derivative; rhodamine dyes which can appear red, yellow, or orange and are bleached upon exposure to near-ultraviolet light; porphyrins (such as porfimer sodium, for example, PHOTOFRIN™ (Quadra Logic Technologies, Vancouver, British Columbia, Canada), a green chromophore bleached by near-ultraviolet light); Rose Bengal, bleached upon exposure to near-ultraviolet light or high intensity visible light (such as in the megawatts/cm$^2$ range); and infrared-bleached dye-paired ion compounds, cationic dye-borate anion complexes, 3-position-substituted coumarin compounds, and bis(diiminosuccinonitrilo)-metal complexes, as described in U.S. Pat. No. 5,409,797, herein incorporated by reference. Some chromophores are only photobleached upon simultaneous absorption of multiple photons, and are therefore unaffected by diffuse solar radiation.

Formulations.

In several embodiments, photoactive materials may be lipophilic or non-lipophilic. Generally, a lipophilic photoactive material is dissolved in a pharmaceutically acceptable oil and applied directly to the area of skin one wishes to treat. A lipophilic photoactive material is dissolved in oil at a final concentration as described herein. As provided herein, the photoactive materials are formulated into a non-dispersive composition in order to retain the photoactive materials at the target region. In certain embodiments, the non-dispersive composition contains at least one of water, a humectant, a surfactant, a thickener, a dye, an antiseptic, an anti-inflammatory agent, an anti-oxidant, a vitamin, a fragrance, an oil, or a topical anesthetic.

In other embodiments, the thermal damage to the epidermis resulting from the photoactive material reduces the efficacy of the barrier function of the epidermis, in particular decreasing the stratum corneum. This facilitates the delivery of drugs or other substances to the dermis and epidermis, which can either enhance the effects of the treatment, or decrease the side effects caused by partial damage of the epidermis and/or dermis, or both. Such beneficial ingredients (such as drugs and other substances), which may enhance the efficacy of skin remodeling include, but are not limited to, growth factors, collagen byproducts, collagen precursors, hyaluronic acid, vitamins, antioxidants, amino acids, retinoids, retinoid-like compounds, and supplemental minerals among others. Groups of drugs and substances, which may decrease side effects, can be steroidal anti-inflammatory drugs, non-steroidal anti-inflammatory drugs, antioxidants, antibiotics, antiviral drugs, antiyeast drugs and antifungal drugs. In an embodiment of the present invention, the vitamins that are used may be vitamin C and/or vitamin E. The supplemental minerals used may be copper and zinc. The antioxidants can be, for example, vitamin C and/or vitamin E. Skin lightening, whitening, or brightening agents are also provided. In several embodiments, one or more of the ingredients described herein are included in the same formulation as the photoactive particles. In other embodiments, these ingredients are provided after treatment with the photoactive particles. In one embodiment, the efficacy of these ingredients are enhanced when used in combination with the photoactive particles.

In further embodiments the epidermis may be treated with sealing or bonding agents to restore barrier function on the skin to prevent infection or scarring. Alternatively bonding agents can be used to tighten, pull, bond, close or otherwise change the mechanical forces within or around the lesion or scar (e.g. reducing tension) during or after treatment to direct the wound healing response, including the deposition of new collagen and re-epithelialization in response to tension. Sealing or bonding agents known in the art include, but are not limited to, cyanoacrylates and other adhesives.

In order to provide effective dermal penetration into the target tissue, the photoactive particles (e.g., plasmonic nanoparticles) in certain embodiments are formulated in various compositions. Preferentially, the nanoparticles are formulated in compositions containing 1-10% v/v surfactants (e.g. sodium dodecyl sulfate, sodium laureth 2-sulfate, ammonium lauryl sulfate, sodium octech-1/deceth-1 sulfate). Surfactants disrupt and emulsify sebum or other hydrophobic fluids to enable improved targeting of hydrophilic nanoparticles to a target region of the skin containing a scar or other feature to be targeted for treatment. Surfactants also lower the free energy necessary to deliver hydrophilic nanoparticles into small hydrophobic crevices. Compositions may also include emulsions of particles at various concentrations (1-20% w/v) in aqueous solutions, silicone/oil solvents, propylene glycol or creams (e.g. comprising alcohols, oils, paraffins, colloidal silicas). In other embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Alternatively, a matrix component such as silica, polystyrene or polyethylene glycol is provided in the formulation. Other formulations include components of surfactants, a lipid bilayer, a liposome, or a microsome. A particle may comprise a larger micron-sized particle.

Applicator Devices.

A benefit of various embodiments of the present invention is the effective treatment of scar tissue, while minimizing adjacent epidermal tissue damage. In various embodiments, the photoactive materials are formulated for dispensing (including but not limited to from an applicator device 300) in a volume of less than about 1 nanoliter to greater than 100 microliters, such as 1 nanoliters, or 10, 20, 30, 40, 50, 60, 70, 80, 90, 100, 110, 120, 130, 140, 150, 160, 170, 180, 190, 200, 210, 220, 230, 240, 250, 300, 350, 400, 450, 500 or above about 500 nanoliters, such as 600, 700, 800, 900 nanoliters, or 1, 2, 3, 4, 5, 6, 7, 8, 9, 10, 11, 12, 13, 14, 15, 16, 17, 18, 19, 20, 21, 22, 23, 24, 25, 30, 35, 40, 45, 50 or above about 50 microliters, such as 75, 100, 150, 200, 250, 300, 400, 500, 600, 700, 800, 900, 1000, or above 1000 microliters, and any ranges between any numbers therein.

In one embodiment, such formulations are in viscous compositions (herein termed "non-dispersive compositions") such that lateral movement across the surface of the skin is reduced or prevented. A non-dispersive composition is substantially retained at the epidermal site of application for a period of time sufficient for the light source to be directed to the target region and one or more exposures of the light source to be completed.

In one embodiment, the apparatus is capable of delivering a volume of a non-dispersive composition of from about 100 nanoliters to about 50 microliters of the liquid formulation on the target area such that the surface area of the target area contacted by the liquid formulation is less than about 50 $mm^2$, e.g., 25 $mm^2$ or less.

In one embodiment, the non-dispersive composition in a volume of about 0.1-2 microliters (e.g., about 0.5 microliters) has a diameter of less than about 2-10 m, (e.g., about 5 mm) at the epidermal surface for at least one minute after contacting of the non-dispersive composition with the epidermal surface. In several embodiments, the photoactive material does not substantially penetrate the epidermal surface.

In one embodiment, the non-dispersive composition does not laterally migrate along the epidermal surface upon which it has been applied at a rate greater than about 1 mm per minute.

In one embodiment, a thickener is added to the composition to achieve a viscosity that provides non-dispersive properties to the formulation.

In some embodiments, the formulations are dispensed using a needle-nose or fine tip applicator, such as those used for dispensing epoxy or other viscous materials. Alternatively, the formulations are dispensed using a pipette, such as a glass or plastic-tipped pipet.

In certain embodiments, an apparatus for delivering a formulation into an acne scar of a human subject contains a supply of a liquid (or semi-liquid such as a gel, or semi-solid such as a paste) formulation containing an photoactive material, which, when put in substantial physical contact with a target area of a skin surface of a human subject, is capable of penetrating the skin surface at the target area (such as an acne scar) to denature at least one pathophysiological collagen deposition present in the acne scar. The supply of the formulation containing the photoactive material may contain sufficient material for a single administration or multiple administrations (e.g., to a single target region multiple times or to multiple target regions one or more times).

Other embodiments for the targeted delivery of photoactive material to small target regions of dermal scar tissue will be apparent to those skilled in the art, in particular those versed in the field of make-up artistry. Applicators for the delivery of photoactive material my include, but are not limited to, a pen, pencil, stencil, brush, powder, metered dosing applicator, sponge, cloth, hand, spray device and other applicators known in the field.

Further provided herein are systems containing an apparatus and a light source. In several embodiments, systems are useful for treating acne scars by denaturing collagen present in an acne scar of a human subject, containing a light source (e.g., a laser light) and an apparatus that contains a supply of a liquid formulation containing a photoactive material, which, when a volume of from about 0.01 ml to about 1 ml is applied in substantial physical contact with a target area of a skin surface of a human subject, is retained in the target area and is capable of penetrating the skin surface at the target area to denature at least one pathophysiological collagen deposition present in the acne scar, by delivering sufficient thermal energy to the targeted area such that the temperature of the collagen deposition in the target area is elevated above the denaturation temperature of the collagen deposition.

In some embodiments the formulations are applied to larger areas beyond the target area, either by painting, swabbing, spraying, or pouring the photoactive formulations on this larger area, and then the formulation is removed, such as by wiping, blotting, suction, or otherwise, from the non-target regions. In some embodiments, an adhesive material is applied to the target skin region in order to enhance retention of the photoactive material at the target skin. Alternatively, a material is applied to a non-target region that diminishes or prevents the photoactive material from adhering to the area outside of the target region.

In some embodiments compositions are formulated to enable photoactive compounds to be easily removed from non-target regions or domains after initial application. For example, "non-sticky" surface coatings may be applied to photoactive material to reduce binding to the skin surface and/or components thereof. Coatings include, but not limited to, silica, polyvinyl pyrrolidone, polysulfone, polyacrylamide, polyethylene glycol, polystyrene cellulose, carbopol or other polymers, monolayers, or compounds that modify charge, alter hydrophobicity, render a surface aliphatic, or otherwise change the binding nature of a material with the skin. In other embodiments the carrier solution may be modified by the addition of surfactants or solvents that change the binding properties of photoactive materials within the formulation.

In some embodiments a device is used to redistribute photoactive material once applied. This redistribution may include expanding the coverage area of the applied composition, increasing the depth of penetration of material in a small crevice or pitted scar, removing volume from applied composition, removing material from non-target skin areas or other patterns of redistribution. Devices that can be advantageous for redistributing material include, but are not limited to, a swab, brush, sponge, cloth, wipe, knife, fine tip applicator and other devices known in the art.

In one embodiment, the mixture is contacted with the skin for about 1 minute to about 1 hour prior to irradiation, though embodiments wherein the solution is contacted beyond 1 hour are provided. In one embodiment, the radiation is administered using a laser capable of delivering one or more wavelengths.

While the invention can be performed, according to several embodiments, using intense pulsed light (IPL) systems, in general narrower range(s) of wavelengths are administered by the laser as compared to broad wavelength ranges delivered with intense pulsed light devices. The administration of more discrete wavelengths permits more accurate control of laser effects than is easily performed when using broad spectrum IPL sources, and moreover, the accurate determination of the proper amount of energy to be provided to a target skin region of a patient is easier with a laser than with and IPL source.

In one embodiment, the energy can be tuned by monitoring thermal heat gradients on the surface of the skin with a thermal/infrared camera. As demonstrated herein, the methods and systems of the present disclosure provide superior efficacy when a surface plasmon is generated on the nanoparticles by the action of the radiation. Typically, the plasmon is generated in a one-photon mode or, alternatively, a two-photon mode, a multi-photon mode, a step-wise mode, or an up-conversion mode.

In various embodiments, the target region is exposed to light of a frequency, for a duration, and for a number of repetitions to provide an amount of heating of all or a substantial portion of the target region that is sufficient to heat at least a portion of the dermal scar tissue to a temperature of at least 40 degrees Celsius, such as 45, 50, 55, 60, 65, 70, 75, 80 or above 80 degrees Celsius for a period of time sufficient to be effective, meaning to cause lethal damage and/or sublethal damage to surrounding parts of the target region, and to reduce the dermal scar tissue. Provided herein are single or multiple exposures useful to achieve the appropriate thermal damage in particular target regions.

The optical source may be coupled to a skin surface cooling device to reduce heating of particles or structures on the skin surface outside of the target region to thereby focus heating to a target region. For example, the treatment incorporates some form of epidermal cooling, which can be administered to the entire face or entire cosmetic unit (e.g., the cheek, chin, nose, or forehead). In various embodiments, cooling devices may include, but are not limited too, refrigerated air, forced air, cryogen spray, cryogen based dynamic cooling, contact cooling (e.g. sapphire window), and other skin surface cooling systems known in the art.

Methods of Treatment.

In some embodiments, the photoactive materials are applied non-dispersively to a target region of skin that has an epidermal surface and dermal scar tissue, which typically contains a single acne scar. In one embodiment, the target region does not exceed about 25 mm$^2$. Energy in the 700 nm to about 1200 nm range is delivered to the target region in an amount sufficient to heat at least a portion of the dermal scar tissue to a temperature of at least 40 degrees Celsius for a period of time sufficient to reduce the dermal scar tissue.

In another embodiment, provided are methods for reducing dermal scar tissue in a human subject, that involve first identifying a target region of skin tissue on a human subject, where the target region comprises an epidermal surface and dermal scar tissue comprising a pathophysiological collagen deposition, dermal matrix, or epidermal surface, and generally where the target region does not exceed about 25 mm$^2$. Pre-identification and selection of the target region is a significant advantage to the present invention as it prevents or substantially reduces injury to non-target regions, thus increasing efficacy, patient comfort, and healing time. The epidermal surface of the identified target region is contacted with a non-dispersive composition containing a photoactive material, and energy is delivered to the target region in the 700 nm to about 1200 nm range in an amount sufficient to heat at least a portion of the dermal scar tissue to a temperature sufficient to cause damage and regeneration, thereby reducing the dermal scar tissue.

In some embodiments, provided are methods for preventing the formation of dermal scar tissue or reducing its progression that involve identifying target regions of inflammatory acne lesions on a human subject, contacting the region with a non-dispersive composition containing photoactive material, and delivering energy to the target region in the 700 nm to about 1200 nm range in an amount sufficient to heat at least a portion of the inflammatory acne lesion to a temperature sufficient to cause damage and regeneration, thereby treating the inflammatory lesion and or reducing the dermal scar tissue resulting from the lesion.

In several embodiments, excessive sweating (e.g., hyperhidrosis is treated) with the application of photoactive particles. In one embodiment, the method includes i) topically administering to a skin surface of the subject a composition of photoactive particles (e.g., plasmonic particles) ii) providing penetration means to redistribute the plasmonic particles from the skin surface to the sweat glands (e.g. eccrine sweat glands, apocrine sweat glands) and iii) causing irradiation of the skin surface by light to activate photoactive materials and thereby heat, damage, treat or otherwise modulate the sweat gland to reduce excessive sweating.

The application of the photoactive material and delivery of energy thereto may be performed once or may repeated one or more times on the same target region, or alternatively, to one or more additional target regions. While the target region of skin can be located anywhere on the human subject's body, acne vulgaris scars are most prominent on the face or neck of the human subject.

EXAMPLES

Example 1. Generation of Plasmonic Nanoparticles for Thermomodulation

In one embodiment, plasmonic nanoparticles, including nanorods, hollow nanoshells, silicon nanoshells, nanoplates, nanorice, nanowires, nanopyramids, nanoprisms, nanoplates and other configurations described herein and known to those skilled in the art, are generated in size ranges from 1-1000 nm under conditions such that surface properties that facilitate deep follicular penetration. Surface properties can be varied on one or multiple (2, 3, or 4) different dimensions to increase nanoparticle concentration in a target tissue domain. Penetration into follicular openings of 10-200 um can be maximized using the nanoparticles described herein. Here, nanoparticles sized in the range of about 10 to about 100 nm are generated, and are preferably assembled or formulated into multiparticle structures having a size in the range of 100-300 nm. Alternatively, a coating (e.g., silica) is grown on uniparticular structures to increase the particle size to the range of 100-300 nm or more.

Surface-Modified Plasmonic Nanoparticles.

An embodiment of a preparation of surface-modified plasmonic nanoparticles is provided as follows. Plasmonic nanoparticles are synthesized with stable cetyltrimethylamonium bromide (CTAB) coating and concentrated from an optical density of 1 O.D. to 100, 200, 300, 400, or 500 O.D. through one to three cycles of centrifugation at 16,000 rcf, with supernatant decanting. Alternatively, CTAB-coated nanoparticles are concentrated and resuspended in 250 Amol/L 5-kDa methyl-polyethylene glycol (PEG)-thiol to make PEG-coated nanoparticles. Verification that PEG polymer stocks are fully reduced is performed using spectrophotometry to measure the thiol activity of polymer-thiols with 5,5-dithiobis(2-nitrobenzoic acid) against a DTT gradient. The solution of methy-PEG-thiol and CTAB-coated nanoparticles is mixed at room temperature for 1 h then dialyzed against 5 kDa MWCO in 4 L distilled water for 24 h. Dialyzed samples are processed through 100-kDa filters to remove excess polymer. Quantification of the number of PEG polymers per particle is performed by surface-modifying nanoparticles with amino-PEG-thiol polymer and quantifying the number of amines with an SPDP assay. For test formulations, 100 O.D. solutions of CTAB-coated plasmonic nanoparticles are made in distilled water, and 100 O.D. PEG-coated plasmonic nanoparticles are made in distilled water, ethanol, DMSO, or mineral oil. Plasmonic nanoparticles with silica shells are created by reacting nanoparticles with silicates such as tetra-ethyl-ortho-silicate (TEOS), sodium silicate, aminopropyletriethoxysilane (APTS), etc. to thicknesses of 5-50 nm or more. Control, vehicle-only formulations contain no nanoparticles.

Embedded Nanoparticles.

In one embodiment, nanoparticles are embedded (or encapsulated) in materials, which allows for the generation of a diverse range of sizes to tune their size. Particle sizes in the range of 100-2000 nm or 200-2000 nm have been shown to enter the hair follicle without penetrating the dermis. Nanoparticles are encapsulated in silica, a synthetic polylactide/co-glycolide co-polymer, porous lauryllactame/caprolactam nylon co-polymer, hydroxyethylcellulose, polyelectrolyte monolayers, or alternatively, in natural hydrogels such as hyaluronic acid, without significantly altering plasmon resonance properties. Nanoparticles are embedded within 100-2000 nm materials or 200-2000 nm materials without covalent attachment or by cross-linking of amines, carboxyls or other moieties on the nanoparticle surface to the polymer structure. The surface of the 100-2000 nm material or 200-2000 nm material may be modified for an optimal zeta potential, hydrophilicity/hydrophobicity, and/or adsorption layer through techniques described herein. Furthermore, the shape of the aspect ratio of the polymer can be modified from low to high to increase concentrations and depths of penetration of the embedded plasmonic nanoparticles. The nanoparticles advantageously have an aspect ratio greater than about 1.

Example 2. Formulation of Thermoablative Plasmonic Nanoparticles for Topical Delivery In another embodiment, nanoparticles are generated as in Example 1 using an appropriate solvent (e.g., water, ethanol, dimethyl sulfoxide). The mixture comprising a plurality of nanoparticles in water is concentrated to about 100-500 O.D. and exchanged for a new solvent by liquid chromatography, a solvent exchange system, a centrifuge, precipitation, or dialysis. The solvent may include an alcohol (e.g., n-Butanol, isopropanol, n-Propanol, Ethanol, Methanol), a hydrocarbon (e.g., pentane, cyclopentane, hexane, cyclohexane, benzene, toluene, 1,4-Dioxane), chloroform, Diethyl-ether, water, an acid (e.g., acetic acid, formic acid), a base, acetone, dimethyl sulfoxide (DMSO), dimethylformamide (DMF), acetonitrile (MeCN), tetrahydrofuran (THF), dichloromethane (DCM) or ethylacetate. The new solvent is combined with a cosmetically or pharmaceutically acceptable carrier, thereby forming a nanoparticle composition. Generally, the particles and carrier will form an emulsion.

Plasmonic nanoparticle formulations are provided that amplify or expedite the penetration of nanoparticles into hair follicles. In some embodiments, nano- and micro-emulsions facilitate partitioning within lipid-rich skin compartments such as the hair follicle. In some embodiments, nanoparticles are formulated in compositions containing 0.5-2% v/v surfactants to enable disruption of the epidermal skin barrier, emulsification of sebum, and improved mixing of hydrophilic nanoparticles in hydrophobic solutions or targeting to hydrophobic space in the skin (e.g. between the hair shaft and surrounding follicle). Formulations of nanoparticles are also provided at various concentrations (1-20% w/v) in aqueous solutions, silicone/oil solvents, polypropylene gel, propylene glycol or creams (e.g. containing alcohols, oils, paraffins, colloidal silicas). In some embodiments, light-absorbing nanoparticles are utilized in solutions having tailored pH, temperature, osmolyte concentration, viscosity, volatility, and other characteristics to improve light-absorbing nanoparticle entry into hair follicles.

Formulations are prepared to maximize nanoparticle stability (degree of aggregation in solution), nanoparticle concentration, and nanoparticle absorbance (degree of laser-induced heating at different concentrations).

When formulations of plasmonic nanoparticles are illuminated with a clinical laser with a wavelength coincident to the peak absorption wavelength of the particle, the formulation heats to thermoablative temperatures more rapidly and to a greater degree than conventional clinical absorptive dyes. FIG. 2 compares the temperature profile of plasmonic particles (1020 nm peak absorption wavelength) to conventional clinical dyes carbon lotion, meladine spray and indocyanine green after exposure to 1064 nm, 20 J/cm$^2$, 55 ms laser pulses. The temperature increase caused by pulsed 1064 nm laser light was more than 2.5 times greater for the plasmonic solution, compared to conventional clinical dyes used at the same dilution (1:1000 dilution from clinical concentration, where clinical concentrations are as follows: carbon 20-200 mg/ml, meladine 1 mg/ml, indocyanine green 5 mg/ml).

Example 3. Use of Plasmonic Nanoparticles for Thermomodulation of Hair

Individuals having blonde, red, gray, or lightly-colored hair are not adequately treated with existing traditional light-based hair removal techniques. Provided herein are methods for using the compositions described herein for the selective removal or reduction of untreated blonde, red, gray, or lightly-colored hair. In one embodiment, plasmonic nanoparticles generated and formulated as described above are introduced into a target tissue region, generally a skin region, and activated with laser-based hair removal systems as known in the art in order to achieve effective hair removal.

To achieve maximal penetration depth and concentration of plasmonic nanoparticles in the hair follicle and/or near components of the sebaceous gland including the sebaceous duct, the sebum, the epithelial linking of the sebaceous gland, and/or near the bulge region including the stem cells, stem cell niche, epithelial lining of the bulge region, and/or near the follicular bulb, an optimal particle size of 30-800 nm (e.g., 100-800 nm) containing one or several plasmonic nanoparticles is constructed. Nanoparticles encapsulating plasmonic nanoparticles can be formulated from any number of polymers or matrices. In some embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Preferentially, a matrix component such as silica, polystyrene or polyethylene glycol is provided in the formulation to improve particle stability and enable facile removal from the skin surface after application and follicle targeting. Other formulations include component of surfactants (e.g. sodium dodecyl sulfate, sodium laureth 2-sulfate, ammonium lauryl sulfate, sodium octech-1/deceth-1 sulfate), a lipid bilayer, a liposome, or a microsome. Plasmonic nanoparticles including nanorods, nanoshells, nanospheres, nanoplates, or nanorice can be encapsulated within a the polymer or lipid-based nanoparticle or matrix or deposited on the particle surface. Alternatively, nanoparticles in the size range of 100-250 nm, 250-500 nm, 800 nm-1500 nm, or greater than 1500 nm can be used.

Pre-treatment of skin with mechanical or chemical exfoliation is used in some embodiments to remove hair-plugs and "open" the follicle for particle delivery. Additionally, hairs can be shaven or waxed to create a void in the hair follicle for particles to fill. The use of physical or thermal force amplifies or expedites the penetration of light absorbing nanoparticles and conjugates thereof into hair follicles, in part by causing dilation of the hair follicle prior to application of the nanoparticles. For example, ultrasound and other sonic forces, mechanical vibrations, hair shaft manipulation (including pulling), physical force, thermal manipulation, and other treatments are utilized to improve entry of light-absorbing nanoparticles into hair follicles. Nanoparticle formulation treatments are performed alone, in combination, sequentially or repeated 1-24 times.

An applicator is used to uniformly apply the composition of nanoparticles into follicles. The applicator can be a sponge, a cloth, direct contact from a finger, a tube, a syringe, a device that applies suction, an aerosol, a spray, or other means known in the art. In one example, a formulation of 1 ml of plasmonic nanoparticles at a concentration of 100 O O.D. with peak resonance of 810 nm is applied to approximately 200 $cm^2$ area of the skin of an adult human subject with a syringe. A cloth is used to evenly distribute solution across the skin area and into the hair follicles. Deep massage from a mechanical vibrator for 2 minutes with or without 1 MHz ultrasound for 5 minutes, is applied to drive particles deep into the follicle. Particles penetrate 50-75% down the full length of the hair shaft at concentrations sufficient to heat skin in a 100 μm radius at incremental temperatures of 5-20-fold greater than is generated in similar volumes of adjacent skin when irradiated by a Diode (810 nm) laser. Acetone, ethanol, or a debriding agent can be used to remove all particles from the surface of the skin that have not deposited in the follicle, in order to reduced or prevent non-follicular heating of the skin.

Nanoparticle formulations are tested in ex vivo animal samples, ex vivo human skin samples, and in vivo human skin including the assessment of: 1) depth of nanoparticle penetration into hair follicles; 2) particle concentration achieved; 3) degree of heating achieved at delivered nanoparticle concentrations; and 4) efficacy of photothermal destruction including temporary and permanent hair removal, 5) clearance of nanoparticles after treatment. To assess nanoparticle penetration depths, plasmonic nanoparticles surface-functionalized with fluorescent molecules are visualized by fluorescence microscopy after histological sectioning or follicular biopsy (removal of hair shaft). Alternatively, plasmonic nanoparticles are directly visualized by dark field microscopy after histological sectioning or follicular biopsy. To assess nanoparticle concentrations at various depths along the follicle, excised skin samples are separated by tape stripping or heat-based techniques, samples are dissolved for bulk analysis of metal concentration by ICP-MS (inductively coupled plasma-mass spectrometry). The macroscopic degree of heating is validated by infrared thermography of skin samples, and by assessment of skin sections subject to laser exposure for thermal damage markers. Finally, one can measure efficacy of photothermal destruction at the nanoparticle accumulation site by analyzing histological cellular lesions at the target site, including the follicular hair shaft, inner root sheath, outer room sheath, and bulge region containing the stem cell niche, which contains the stem cells that contribute to new hair growth. As the bulge region is generally localized about midway (~50% down the length of) the hair shaft, permanent hair removal is sufficiently achieved by accumulation of plasmonic nanoparticles to this depth. In some situations, nanoparticle delivery may also generate a heat gradient emitting further down the hair shaft. Animal studies are useful to demonstrate the efficacy of unpigmented hair removal by comparing heat profiles, thermal ablation of hair shaft, and thermal damage of bulge stem cells in treated hairless rodents, albino rodents and dark-haired rodents. Efficacy on live human skin is measured by measuring hair counts at 3 and 12 month follow ups. Biopsies are taken from select patients at 2, 4, and 6 week follow ups to verify that nanoparticles are cleared from the skin without embedding in the dermis.

Hair Follicle Penetration of Fluorescently-Labeled Nanoparticles Determined Using Porcine Skin Explants and Confocal Imaging.

Figure 3:
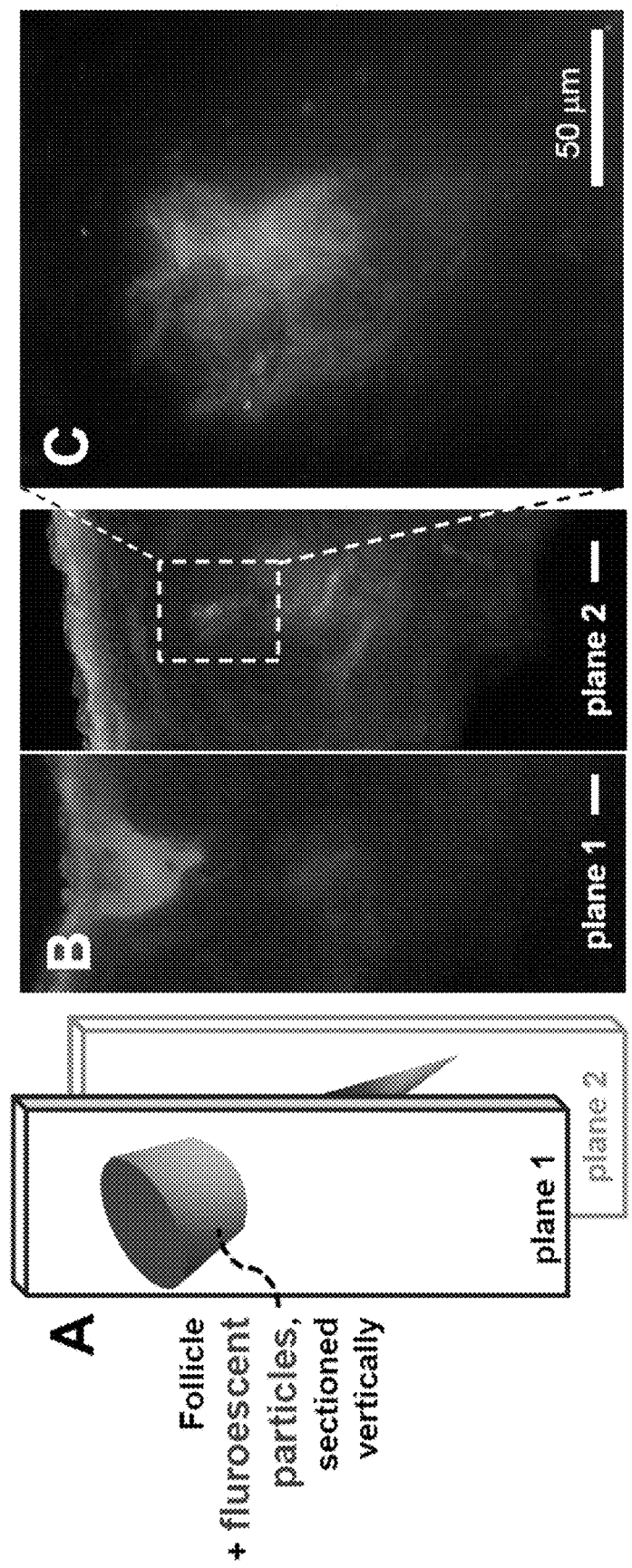
FIG. 3 is illustrative of hair follicle penetration of fluorescently-labeled nanoparticles determined using porcine skin explants and confocal imaging of certain embodiments of the subject matter described herein. Depicted is (A) schematic of treated porcine skin, sectioned and imaged at an angle to the follicle, in two serial 60 µm planes: 'plane 1' (showing follicle infundibulum) and 'plane 2' (showing deep follicle); (B) representative confocal images show red fluorescent nanoparticles (548 nm) within superficial and deep follicle, but not in underlying dermis; and (C) red fluorescent nanoparticles retained in the deep follicle (~400 µm) at high magnification. Green is tissue autofluorescence.

A 25 mg/ml aqueous solution silicon dioxide-coated nanoparticles (200 nm diameter) was contacted with freshly thawed porcine skin, after which excess nanoparticle suspension was removed and manual massage was performed for three minutes. The explant was sectioned and subjected to confocal imaging. As shown in FIG. 3A, explant sections were imaged at angles to the hair follicles in 60 μm planes; Plane 1 shows the follicle infundibulum, while Plane 2 shows the distal regions of the follicle. FIG. 3B demonstrates representative confocal images showing that red nanoparticles (548 nm absorbance) are visible within both the superficial and deep follicles, but are not detectable in dermal layers beneath the follicles. FIG. 3C shows high-magnification imaging of red nanoparticles localized to and retained within a deep follicle (~400 μm). Green color indicates tissue autofluorescence (488 nm).

Hair Follicle Penetration of Plasmonic Nanoparticles Determined Using Porcine Skin and Dark Field Imaging.

Figure 4:
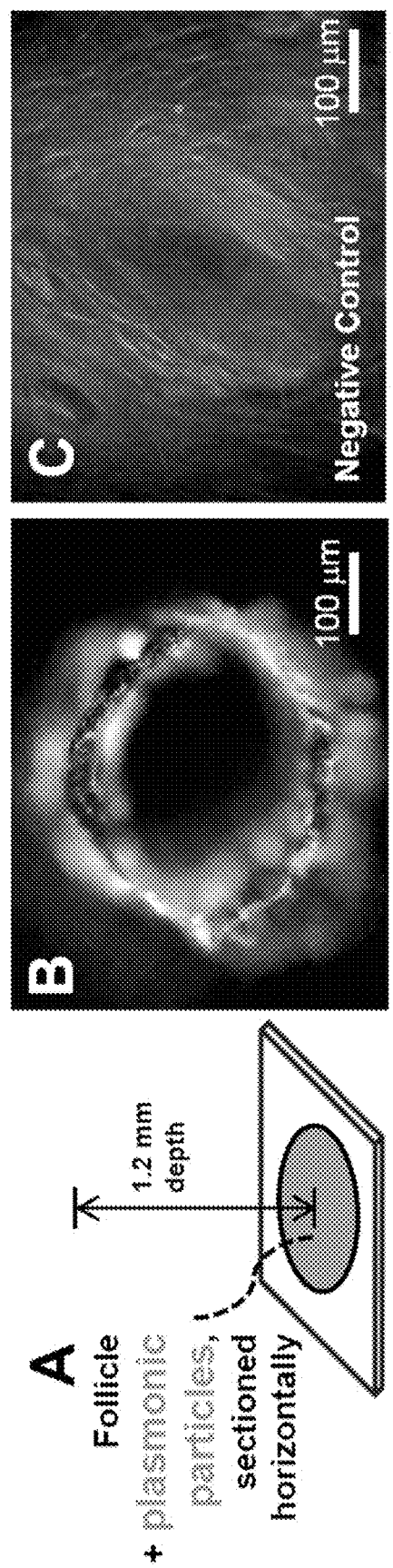
FIG. 4 is illustrative of a hair follicle penetration of plasmonic nanoparticles determined using porcine skin explants and dark field imaging. Shown is (A) schematic of treated porcine skin, sectioned and imaged horizontal to the follicle; (B) bright blue plasmonic particles are visible in a 1.2 mm deep section, and are differentiated from (C) untreated (negative control) porcine skin, where no pigments are visible.

A 100 O.D. suspension of plasmonic nanoparticles (200 nm diameter) was contacted with freshly thawed porcine skin, after which excess nanoparticle suspension was removed and manual massage performed for three minutes. The procedure was repeated for a total of 3 applications, and surface residue removed with several 3-5 applications of alternating water and ethanol. The skin sample was excised, fixed, sectioned along horizontal plane and subjected to dark field imaging. As shown in FIG. 4A, skin samples were sectioned and imaged horizontal to the hair follicle at various depths. In skin section images, plasmonic nanoparticles were observed as bright blue color point sources at depths up to 1.2 mm deep in porcine follicle spaces (FIG. 4B). Control samples with no plasmonic nanoparticles were clearly differentiated (FIG. 4C). ICP-MS is also performed on skin sections to assess nanoparticle concentrations at various depths along the follicle.

Hair Follicle Penetration of Nanoparticles in Hairless Rodents, Albino Rodents and Dark-Haired Rodents.

White-haired Swiss Webster mice (n=3) at 8 weeks old are anesthetized with injectable ketamine/xylazine anesthetic solution and dorsal back skin and hair washed and dried. Prior to formulation administration, three 10 cm×10 cm areas are demarcated by permanent marker on each mouse and subjected to hair removal by 1) electric razor, 2) Nair depilation reagent, or 3) warm wax/rosin mixture application and stripping. Each mouse is treated by pipette with up to 3 nanoparticle formulations, in quadruplicate 5-µl spot sizes per demarcated skin area (up to 12 spots per area or 36 spots per mouse). Precise spot locations are demarcated with pen prior to pipetting. Duplicate treatment spots on the dorsal left side are massaged into skin for 5 minutes, while duplicate treatment spots on the dorsal right side are applied without massage. Thirty minutes after application, mice are sacrificed by carbon dioxide asphyxiation and cervical dislocation, and skin is carefully excised and punched into sections along spot size demarcations. Skin biopsies are fixed in 10% paraformaldehyde, paraffin-embedded, and cut into 5-um sections on a microtome in transverse directions. Slides with mounted paraffin sections are deparaffinized and stained with hematoxylin and eosin (H&E) or kept unstained for dark field microscopy. Using H&E staining, light microscopy and/or dark field microscopy, greater than 50 follicles per formulation are imaged, and scoring is performed for skin sections for visible macroscopic nanoparticle accumulation in the follicle, along the hair shaft, at the site of the putative bulge stem cell niche, and at the depth of the follicle bulb. On serial histological sections, a silver enhancement staining kit based on sodium thiosulfate may be used to enlarge the plasmonic nanoparticle signal via the precipitation of metallic silver. Phase and dark field micrographs are captured and used to record the depths of follicular penetration for each nanoparticle formulation and method of application. ICP-MS is also performed on skin sections to assess nanoparticle concentrations at various depths along the follicle.

Assessment of Photothermal Destruction at the Nanoparticle Accumulation Site.

Treated areas of pig, human or mouse skin are irradiated with a laser coincident with the peak absorption wavelength of nanoparticles (e.g. 1064 nm YAG laser for 1020 nm plasmonic particles) using clinical parameters (1 s exposure of 30-50 J/cm$^2$ and a pulse width of 10-50 ms). To determine microscopic photothermal damage of target skin structures such as the hair follicle and hair follicle bulge stem cells, at ten days after application and irradiation, human subjects receive lidocaine injections to numb treatment areas and skin is carefully excised and punched into sections along spot size demarcations. Fresh human skin biopsies or explanted human and animal skin samples are fixed in 10% paraformaldehyde, paraffin-embedded, and cut into 5-um sections on a microtome in transverse directions, or they are fixed in Zamboni's solution with 2% picric acid and cryosectioned by freezing sliding microtome. Slides with mounted paraffin sections are deparaffinized and stained with hematoxylin and eosin (H&E). Histological sections are examined at various depths for markers of thermal damage and inflammation. Hematoxylin and eosin (H&E) is used to image skin and follicle microanatomy and indicate degeneration of hair shafts, atrophy of sebaceous glands, and cell vacuolization (indicating cellular damage). Nitro blue tetrazolium chloride (NBTC), a lactate dehydrogenase stain that is lost upon thermal injury to cells, is used to assess damage to keratinocytes. Cellular damage in follicles of skin samples receiving plasmonic nanoparticle plus laser treatment is scored and compared to those receiving laser treatment alone. Live treated human skin areas are also followed clinically for 2 weeks to 3 months following plasmonic nanoparticle+laser treatment, or during repeated plasmonic nanoparticle+laser treatments, and compared to baseline digital photograph taken prior to first treatment, and to negative control laser only treatments. Clinical observations of hair removal, as well as erythema, edema, discomfort, irritation or scarring, are noted to determine degree of non-specific thermal damage.

Effect of Plasmonic Particle Coating on Specificity of Delivery and Photothermal Heating.

Figure 5:
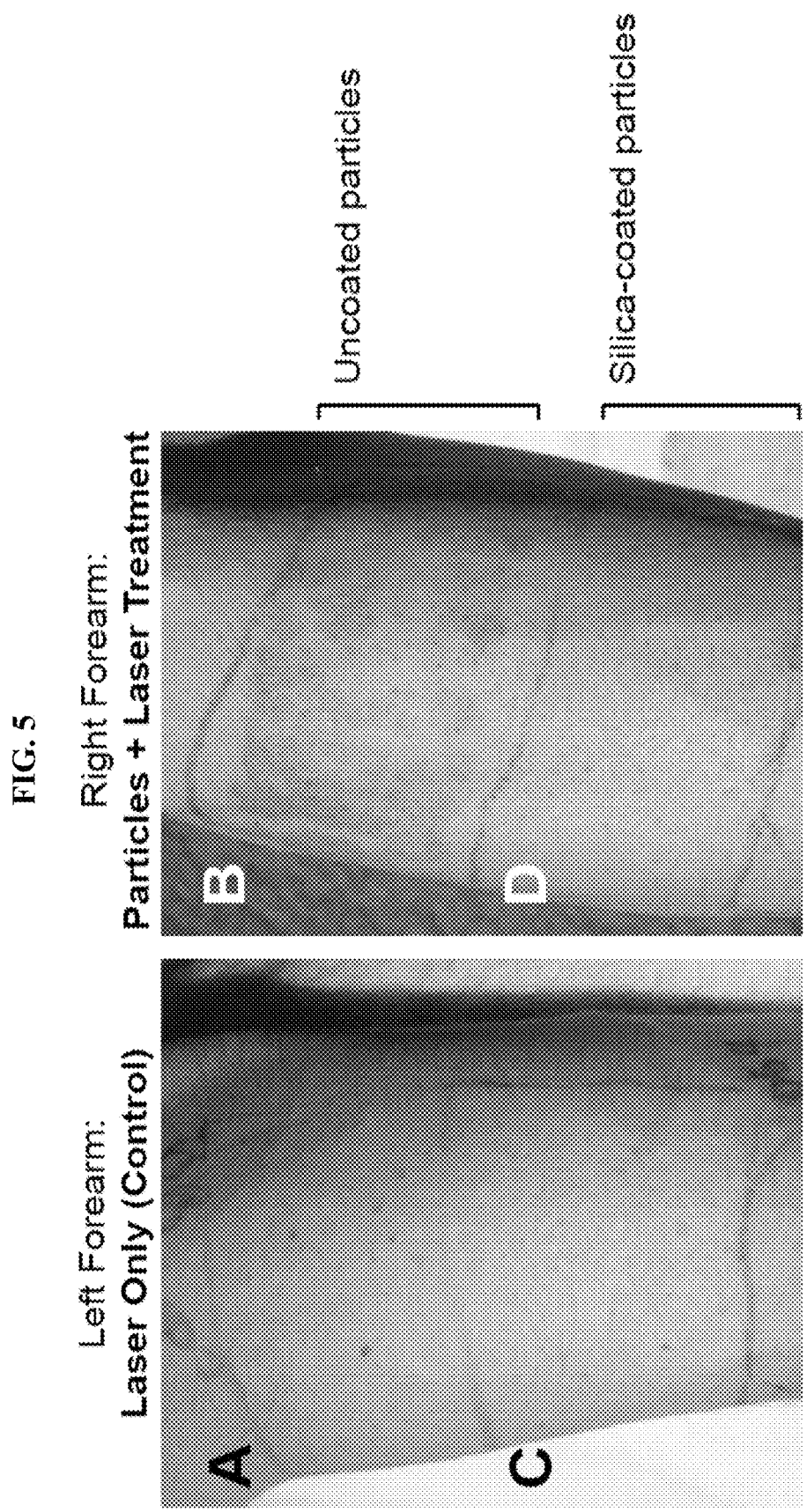
FIG. 5 depicts clinical observations in live human skin treated with Laser Only (left forearm) or Plasmonic Particles+Laser (right forearm) demonstrates non-specific and specific photothermal damage. (A,B) In the top panel, human skin was irradiated with 810 nm laser pulses (30 J/cm2, 30 ms, 2 passes) alone (A), or after treatment with a formulation of 830 nm resonant, Uncoated plasmonic nanoparticles in 20% propylene glycol (B). The plasmonic nanoparticle formulation was applied with 3 minute massage, and the skin surface wiped with 3 applications of alternative water and ethanol before laser irradiation. In several embodiments of the invention, massage (e.g., hand massage, vibration, mechanical vibration) can be applied at frequencies of less than 1 kHz, 1 Hz-900 Hz, 5-500 Hz, 10-100 Hz, 1-80 Hz, 50-250 Hz, and any frequencies therein. At 30 minutes following laser irradiation, non-specific clinical burns were observed in B compared to A, due to significant photothermal heating of residual, uncoated particles on the skin surface. (C,D) In the bottom panel, human skin was irradiated with 1064 nm laser pulses (40 J/cm2, 55 ms, 3 passes) alone (C), or after treatment with a formulation of 1020 nm resonant, Silica-coated plasmonic nanoparticles in 20% propylene glycol (D). The plasmonic nanoparticle formulation was applied with 3 minute massage, and the skin surface wiped with 3 applications of alternative water and ethanol before laser irradiation. At 30 minutes following laser irradiation, no evidence of burning of the skin or erythema was observed in D or C, as Silica-coated particles could be sufficiently wiped from the skin surface. Magnified photography of D showed specific photothermal damage (perifollicular erythema and edema) in the nanoparticle-targeted site.
Figure 6:
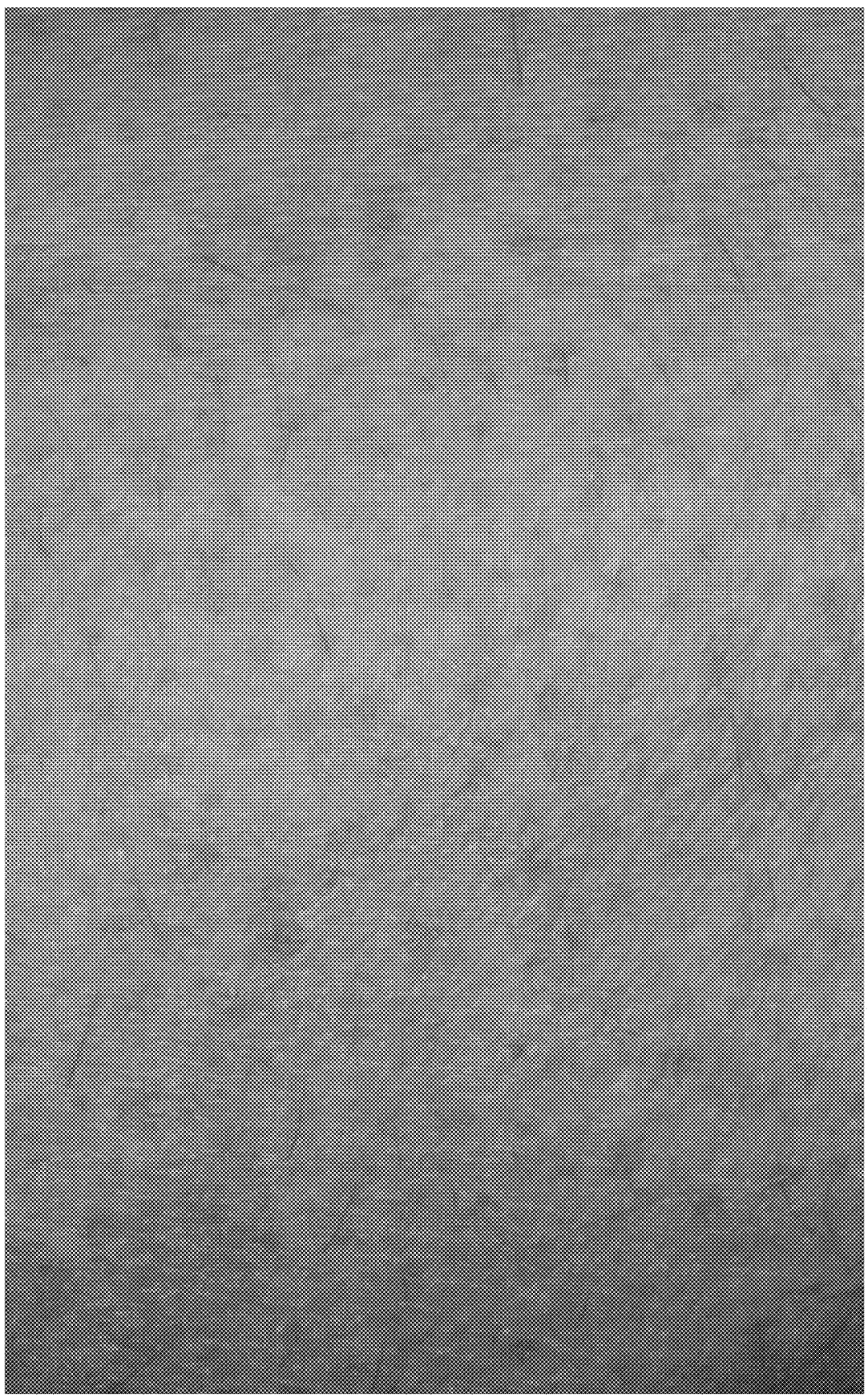
FIG. 6 is a photograph showing nanoparticle-targeted photothermal damage in live human skin treated with a plasmonic nanoparticle formulation and clinical laser. A formulation of 1020 nm resonant, silica-coated (200 nm-diameter) plasmonic nanoparticles in 20% propylene glycol and 3 minute massage was contacted with live human skin. The procedure was repeated 3 times, and skin surface wiped with 3 applications of alternating water and ethanol to remove residual particles. The treated skin was irradiated with 1064 nm laser pulses (40 J/cm$^2$, 55 ms, 3 passes). Following laser irradiation, clinical observation of perifollicular erythema and edema was visible at hair follicles where nanoparticles were targeted, but not visible in surrounding or non-particle-treated tissues.

Preferentially, a matrix component such as silica, polystyrene or polyethylene glycol is provided in the formulation to improve particle stability and enable facile removal from the skin surface after application and follicle targeting. Acetone, ethanol, or a debriding agent can be used to remove all particles from the surface of the skin that have not deposited in the follicle, in order to reduced or prevent non-follicular heating of the skin. In FIG. 5, live human skin was treated with uncoated plasmonic particles compared to silica-coated plasmonic particles, prior to laser-irradiation and comparison to no particle treatment (laser only) controls. Pre-treatment of skin, including shaving with razor and microdermabrasion (15 sec, medium setting) to remove hair-plugs and "open" the follicle for particle delivery, was performed on both forearms. Human forearm skin was irradiated with 810 nm laser pulses (30 J/cm$^2$, 30 ms, 2 passes) alone (FIG. 5A), or after treatment with a formulation of 830 nm resonant, Uncoated plasmonic nanoparticles in 20% propylene glycol (FIG. 5B). The plasmonic nanoparticle formulation was applied with 3 minute massage and repeated 3 times, and the skin surface wiped with 3 applications of alternative water and ethanol before laser irradiation. At 30 minutes following laser irradiation, non-specific clinical burns were observed due to significant photothermal heating of residual, uncoated particles on the skin surface (FIG. 5B). Live human skin was also irradiated with 1064 nm laser pulses (40 J/cm$^2$, 55 ms, 3 passes) alone (FIG. 5C), or after treatment with a formulation of 1020 nm resonant, Silica-coated plasmonic nanoparticles in 20% propylene glycol (FIG. 5D). The plasmonic nanoparticle formulation was applied with 3 minute massage and repeated 3 times, and the skin surface wiped with 3 applications of alternative water and ethanol before laser irradiation. At 30 minutes following laser irradiation, no evidence of burning of the skin or erythema was observed, as Silica-coated particles could be sufficiently wiped from the skin surface (FIG. 5D). Magnified photography of the skin area treated with Silica-coated particles+Laser shows specific photothermal damage (perifollicular erythema and edema) in the nanoparticle-targeted site, without damage to surrounding or non-particle-treated tissues (FIG. 6).

Example 4. Use of Plasmonic Nanoparticles for Acne Treatment

In one embodiment, provided herein are methods for using the compositions described herein for the treatment of acne vulgaris and other *acnes* and acne-like skin conditions, but the selective targeting of sebaceous follicles, particularly the sebaceous glands and/or hair follicles. Plasmonic nanoparticles generated and formulated as described above are introduced into a target tissue region, generally a skin region, and activated with laser-based systems as known in the art in order to achieve effective hair removal.

To achieve maximal penetration depth and concentration of plasmonic nanoparticles in the hair follicle and/or near components of the sebaceous gland including the sebaceous duct, the sebum, the epithelial linking of the sebaceous gland, and/or near the bulge region including the stem cells, stem cell niche, epithelial lining of the bulge region, and/or near the follicular bulb, an optimal particle size of 100-800 nm containing one or several plasmonic nanoparticles is constructed. Nanoparticles encapsulating plasmonic nanoparticles can be formulated from any number of polymers or matrices. In some embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Preferentially, a matrix component such as silica, polystyrene or polyethylene glycol is provided in the formulation to improve particle stability and enable facile removal from the skin surface after application and follicle targeting. Preferentially, formulations include surfactants (e.g. sodium dodecyl sulfate, sodium laureth 2-sulfate, ammonium lauryl sulfate, sodium octech-1/deceth-1 sulfate), components of a lipid bilayer, a liposome, or a microsome. Surfactants disrupt the epidermal skin barrier, emulsify sebum, improve mixing of hydrophilic nanoparticles with hydrophobic solutions, and reduce entropic barriers to delivering hydrophilic particles to hydrophobic regions of the skin (e.g. between the hair shaft and surrounding sheath or follicle). Plasmonic nanoparticles including nanorods, nanoshells, nanospheres, or nanorice can be encapsulated within the polymer nanoparticle or matrix or deposited on the particle surface. Alternatively, nanoparticles in the size range of 100-250 nm, 250-500 nm, 800 nm-1500 nm, or greater than 1500 nm can be used.

The use of physical or thermal force amplifies or expedites the penetration of light absorbing nanoparticles and conjugates thereof into hair follicles and/or sebaceous glands, in part by causing dilation of the hair follicle prior to application of the nanoparticles. For example, ultrasound and other sonic forces, mechanical vibrations, hair shaft manipulation (including pulling), physical force, thermal manipulation, and other treatments are utilized to improve entry of light-absorbing nanoparticles into hair follicles and/or sebaceous glands. Nanoparticle formulation treatments are performed alone, in combination, sequentially or repeated 1-24 times.

Prior to application of the plasmonic nanoparticles, a pre-treatment step of removing excess sebum from the surface of the skin may be performed using chemical and/or mechanical means. Pre-treatment of skin with mechanical or chemical exfoliation is used in some embodiments to remove hair-plugs and "open" the follicle for particle delivery. Additionally, hairs can be shaven or waxed to create a void in the hair follicle for particles to fill.

An applicator is used to uniformly apply the composition of nanoparticles into follicles. The applicator can be a sponge, a cloth, direct contact from a finger, a tube, a syringe, a device that applies suction, an aerosol, a spray, or other means known in the art. In one example, a formulation of 1 ml of plasmonic nanoparticles at a concentration of 100 O.D. with peak resonance of 810 nm is applied to approximately 200 cm² area of the skin of an adult human subject with a syringe. A cloth is used to evenly distribute solution across the skin area and into the hair follicles. Massage from a mechanical vibrator for 2 minutes with or without ultrasound at 1 MHz for 5 minutes is applied to drive particles deep into the follicle. Particles penetrate ~50% down the full length of the hair shaft at concentrations sufficient to heat skin in a 100 um radius at incremental temperatures of 5-20-fold greater than is generated in similar volumes of adjacent skin when irradiated by a Diode (810 nm) laser. Acetone, ethanol, or a debriding agent can be used to remove all particles from the surface of the skin that have not deposited in the follicle, in order to reduced or prevent non-follicular heating of the skin.

Delivery of Plasmonic Nanoparticles to the Sebaceous Gland Determined Using Human Abdominoplasty Skin and Dark Field Imaging.

Figure 7:
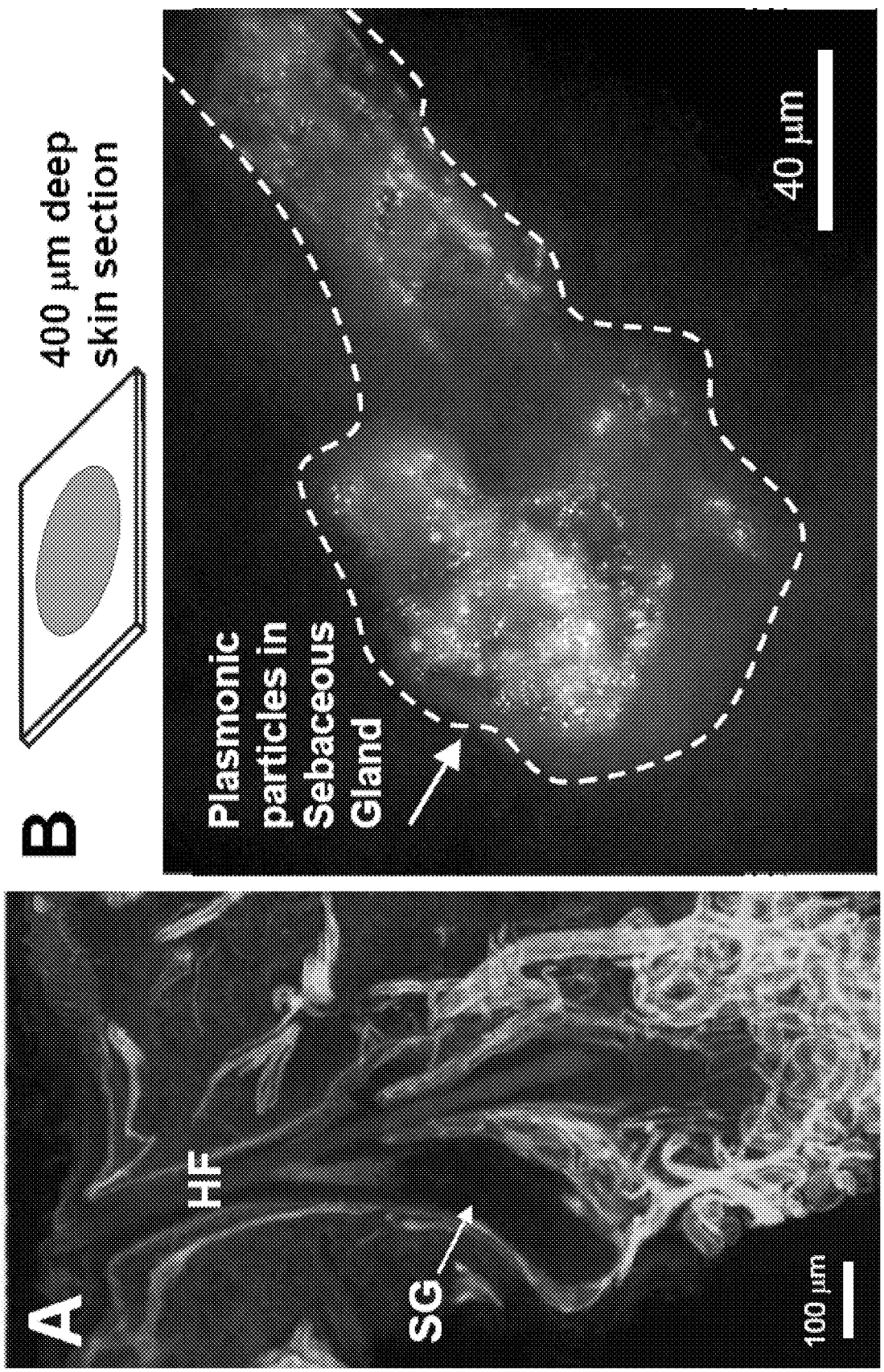
FIG. 7 is illustrative of a plasmonic nanoparticle formulation delivery to human skin sebaceous gland. (A) Confocal microscope image of a human skin biopsy and section, immunostained for Collagen IV basement membrane (blue) and PGP 9.5 nerve marker (green), shows hair follicle (HF) and sebaceous gland (SG) microanatomy. Red is silica nanoparticles (200 nm). (B) Schematic and dark field microscope image of excised human skin treated with plasmonic nanoparticle formulation, then sectioned and imaged horizontal to the follicle. Bright blue plasmonic particles are visible up to 400 µm deep and within the human sebaceous gland.

The human sebaceous gland exists within the pilosebaceous unit consisting of the hair, hair follicle, arrector pili muscle and sebaceous gland. In FIG. 7A, a human skin biopsy is immunostained with antibodies against Collagen IV (basement membrane marker, blue) and PGP 9.5 (nerve marker, green) to visualize representative pilosebaceous unit microanatomy, including the hair follicle (HF), sebaceous gland (SG) and arrector pili muscle. To deliver nanoparticles to the hair follicle and sebaceous gland, skin was first pre-treated with shaving to remove extruding hair, microdermabrasion (15 sec, medium setting) to remove hair-plugs and corneocytes, and chemical depilation to "open" follicle microwells for particle delivery. A 100 O.D. suspension of plasmonic nanoparticles (200 nm diameter), formulated in 1% sodium dodecyl sulfate (SDS) and 20% propylene glycol (PG) was contacted with excised human abdominoplasty skin, after which excess nanoparticle suspension was removed and manual massage performed for three minutes, followed by ultrasound (1 MHz) for 5 minutes. The procedure was repeated for a total of 3 applications, and surface residue removed with 3-5 applications of alternating water and ethanol. The skin sample was excised, fixed, sectioned along horizontal planes and subjected to dark field imaging. As assessed by dark field imaging of horizontal skin sections, compositions of plasmonic nanoparticles with a cosmetically acceptable carrier of 1% SDS/20% PG administered with massage and ultrasound can be delivered 400-600 µm deep into the human follicle and specifically into the sebaceous gland (FIG. 7B).

Cosmetic Formulations for Follicle and Sebaceous Gland Delivery in Human Skin.

Figure 8:
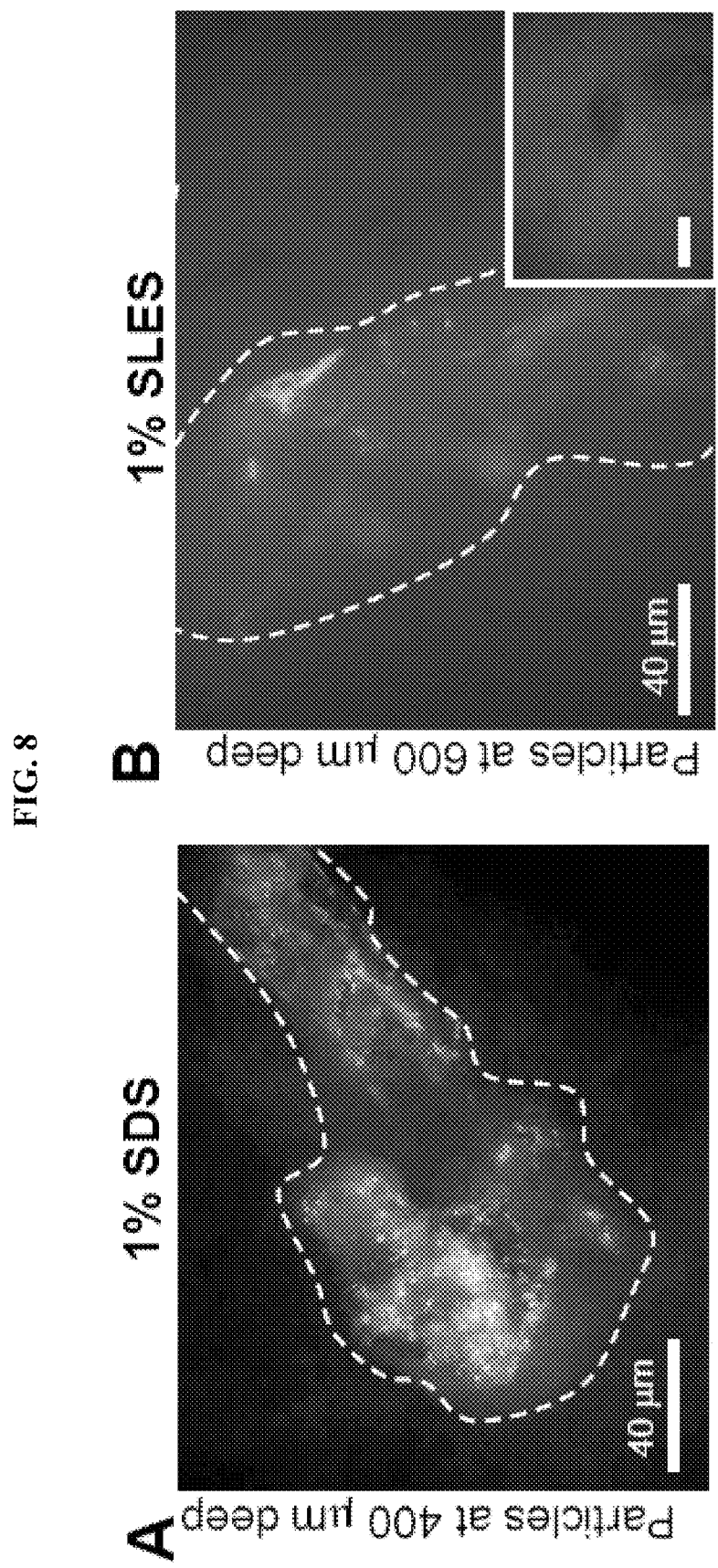
FIG. 8 is illustrative of cosmetic formulations of plasmonic nanoparticles for sebaceous gland targeting that include surfactants. Silica-coated nanoparticles (200 nm diameter, 100 O.D.) were formulated in 20% propylene glycol with the addition of surfactants sodium dodecyl sulfate (SDS) or sodium laureth-2 sulfate (SLES), applied to human skin with massage+ultrasound, and skin was sectioned in horizontal planes for dark field microscopy. (A) Formulations of plasmonic particles in 1% SDS/20% PG penetrated sebaceous gland down to 400 um as in FIG. 7. (B) Formulations of plasmonic particles in 1% SLES/20% PG penetrated sebaceous gland down to 600 um. Inset shows a skin section without visible particles (scale bar 40 um). Sebaceous gland is pseudo-outlined.

Preferentially, formulations include surfactants (e.g. sodium dodecyl sulfate, sodium laureth 2-sulfate, ammonium lauryl sulfate, sodium octech-1/deceth-1 sulfate), components of a lipid bilayer, a liposome, or a microsome. Surfactants disrupt the epidermal skin barrier and emulsify the sebum to enable improved mixing of hydrophilic nanoparticles in hydrophobic solutions. Humectants such as propylene glycol are used to help improve topical viscosity and maintain physiological pH. To demonstrate the efficacy and mechanism of embodiments of cosmetic formulations for human sebaceous gland delivery, skin was first pre-treated with shaving to remove extruding hair, microdermabrasion (15 sec, medium setting) to remove hair-plugs and corneocytes, and chemical depilation to "open" follicle microwells for particle delivery. Two separate 100 O.D. suspensions of plasmonic nanoparticles (200 nm diameter) were formulated in 1% sodium dodecyl sulfate and 20% propylene glycol (SDS/PG) or in 1% sodium laureth-2-sulfate and 20% propylene glycol (SLES/PG). Formulations were contacted with two separate excised human abdominoplasty skin samples, and massage for 3 minutes followed by ultrasound (1 MHz) for 5 min was performed to drive particles deep into the follicles. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of plasmonic nanoparticles with a cosmetically acceptable carrier of 1% SLES/20% administered with massage and ultrasound can be delivered 400-600 µm deep into the human follicle and specifically into the sebaceous gland (FIG. 8B).

Impact of Massage Vs. Ultrasound on Nanoparticle Delivery to Human Follicles and Sebaceous Gland.

Figure 9:
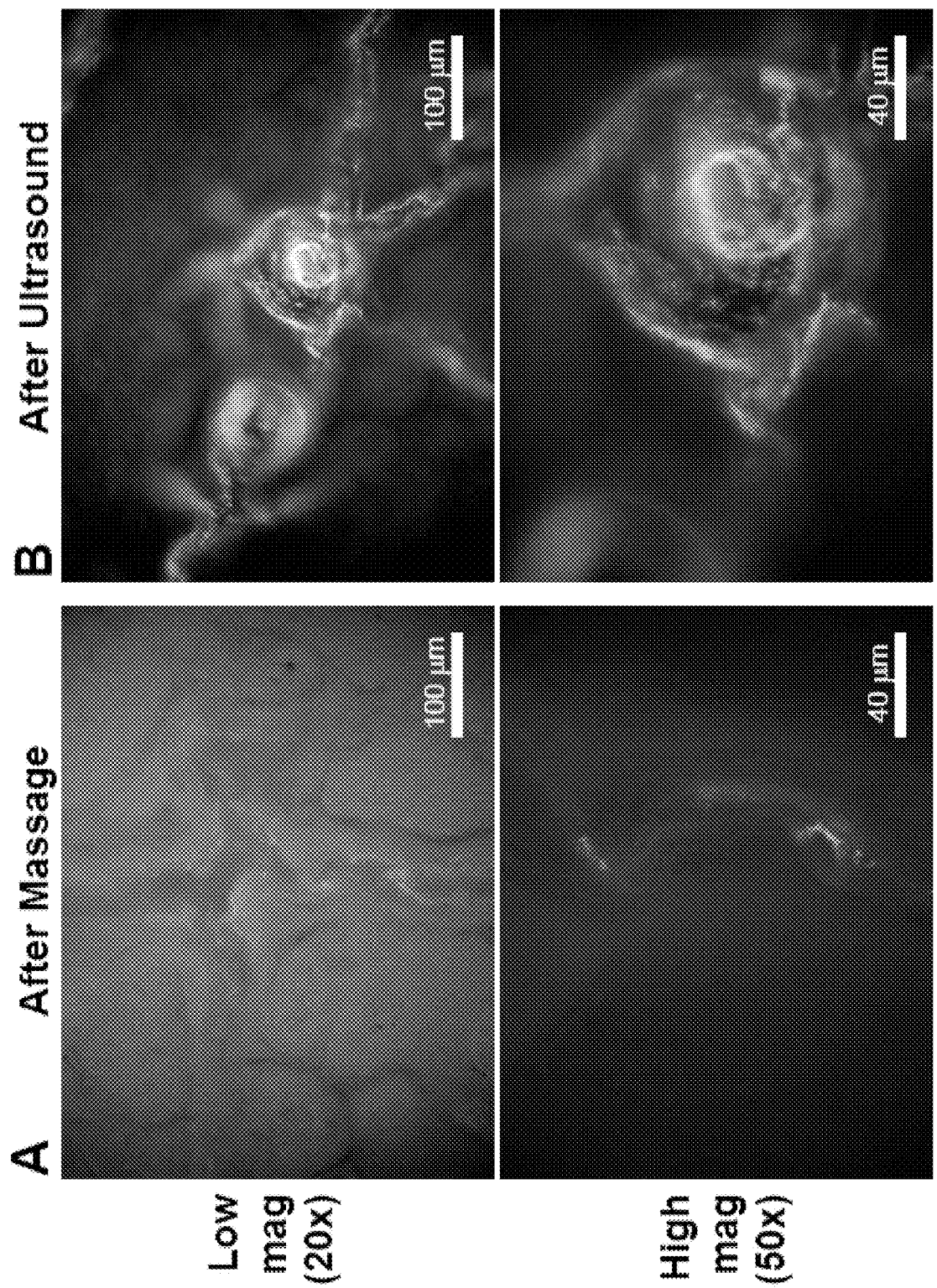
FIG. 9 is an image depicting impact of massage vs. ultrasound on nanoparticle targeting to the human follicle and sebaceous gland. Silica-coated nanoparticles (200 nm diameter, 100 O.D.) were formulated in 1% SDS/20% propylene glycol and applied to human skin with massage or ultrasound. Dark field images of horizontal planar sections taken at low (20×) and high (50×) magnification show (A) little to no accumulation of plasmonic particles into follicle infundibulum after massage alone, compared to (B) follicle infundibulum expansion and significant plasmonic particle accumulation after ultrasound alone. In several embodiments of the invention, low frequency ultrasound can be applied at frequencies of 1 kHz to 500 kHz, e.g., 1 kHz-100 kHz, 5 kHz-45 kHz, 20 kHz-50 kHz, 30 kHz-40 kHz, 30 kHz, 40 kHz, and any ranges or frequencies therein.) In several embodiments of the invention, massage (e.g., hand massage, vibration, mechanical vibration) can be applied at frequencies of less than 1 kHz, 1 Hz-900 Hz, 5-500 Hz, 10-100 Hz, 1-80 Hz, 50-250 Hz, and any frequencies therein.

In some embodiments, ultrasound and/or other sonic forces, mechanical vibrations, hair shaft manipulation (including pulling), physical force, thermal manipulation, and other treatments are utilized to improve entry of light-absorbing nanoparticles into hair follicles and/or sebaceous glands. Mechanical massage improves follicular penetration through hair shaft 'pumping' mechanisms, while ultrasound enhances transdermal drug delivery through temporary disruption of the skin's lipid bilayer, bubble formation, and liquid microstreaming. To characterize the effects of massage decoupled from ultrasound, skin was first pre-treated with shaving to remove extruding hair, microdermabrasion (15 sec, medium setting) to remove hair-plugs and corneocytes, and chemical depilation to "open" follicle microwells for particle delivery. A 100 O.D. suspension of plasmonic nanoparticles (200 nm diameter), formulated in 1% sodium dodecyl sulfate (SDS) and 20% propylene glycol (PG), was contacted with three separate excised human abdominoplasty skin samples. In the three treated human skin samples, massage only was performed for 3 minutes, ultrasound only (1 MHz) was performed for 5 minutes, or massage followed by ultrasound was performed to drive particles deep into the follicles. In a fourth sample, no particles were applied to skin. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of plasmonic nanoparticles with a cosmetically acceptable carrier of 1% SLES/20% administered via ultrasound deliver more plasmonic nanoparticles to the infundibulum versus massage, albeit both mechanisms facilitate delivery (FIG. 9).

Additional Plasmonic Nanoparticle Formulations for Follicle and Sebaceous Gland Delivery in Human Skin.

Figure 10:
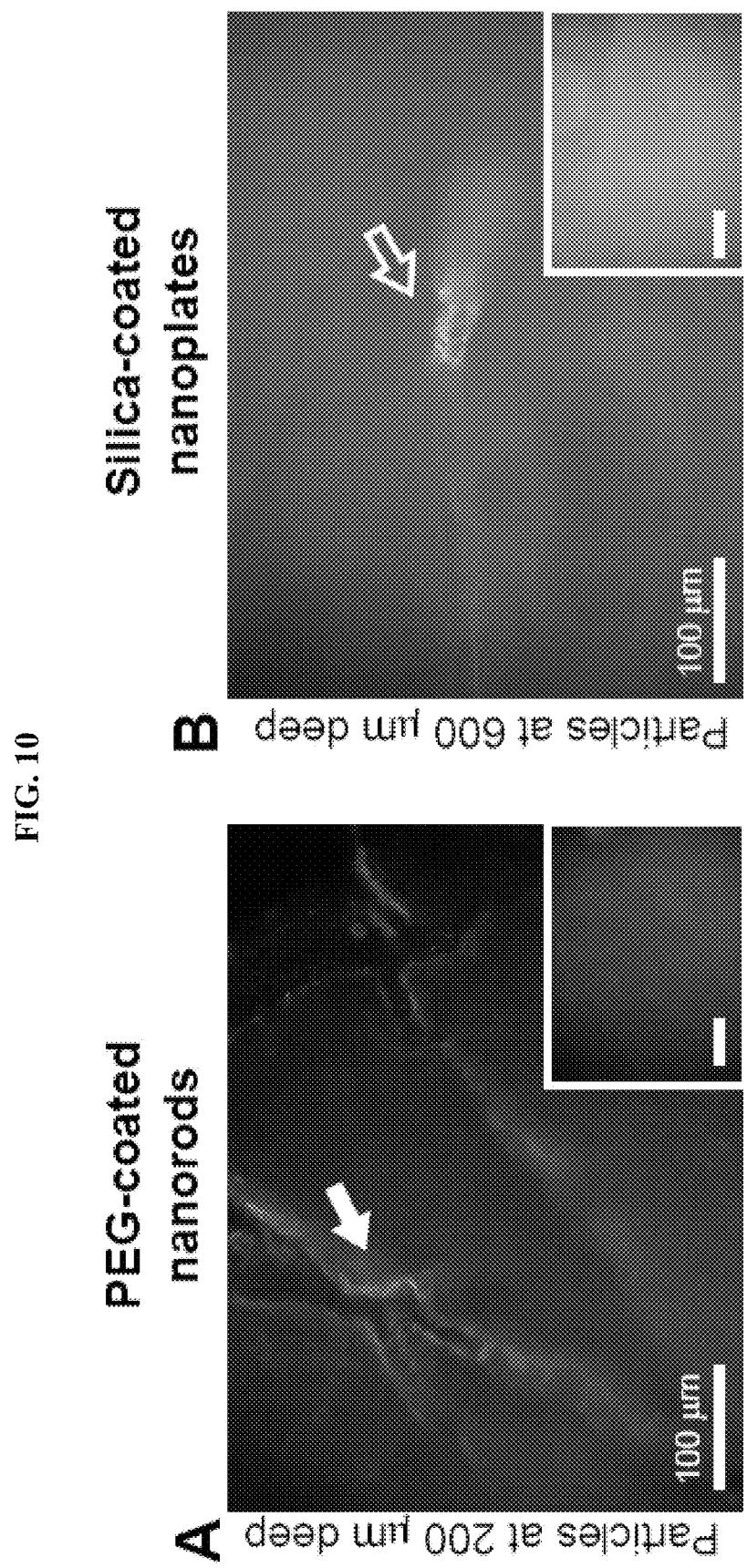
FIG. 10 depicts an embodiment of the plasmonic nanoparticle cosmetic formulations for sebaceous gland targeting. Plasmonic nanoparticles comprising different shapes and coatings were formulated in 1% SDS/20% propylene glycol and applied to human skin with massage+ultrasound, and skin was sectioned in horizontal planes for dark field microscopy. (A) Polyethylene glycol (PEG)-coated nanorods (gold, 15×30 nm dimension) were observed within the follicle infundibulum up to 200 um deep (white arrow). (B) Lower concentration (10 O.D.) Silica-coated nanoplates (silver, 200 nm diameter) were observed up to 600 um deep in the follicle and in the sebaceous gland (open arrow). Inset shows skin sections without visible particles (scale bar 100 um).

In some embodiments, plasmonic nanoparticles include nanorods, nanoshells, nanospheres, or nanorice, or plasmonic nanoparticles encapsulated within the polymer nanoparticle or matrix or deposited on the particle surface. Preferentially, a matrix component such as silica, polystyrene or polyethylene glycol is provided in the formulation to improve particle stability and enable facile removal from the skin surface after application and follicle targeting. To demonstrate the formulation of additional plasmonic nanoparticle shapes and concentrations for follicle, infundibulum, and sebaceous gland delivery, skin was first pre-treated with shaving to remove extruding hair, microdermabrasion (15 sec, medium setting) to remove hair-plugs and corneocytes, and chemical depilation to "open" follicle microwells for particle delivery. Separately, 10 O.D. suspensions of Silica-coated nanoplates, 30 O.D. suspensions of polyethylene-glycol coated plasmonic nanorods, and fluorescent silica particles were formulated in 1% sodium dodecyl sulfate and 20% propylene glycol. Formulations were contacted with three separate excised human abdominoplasty skin samples, and massage for 3 minutes followed by ultrasound (1 MHz) for 5 min was performed to drive particles deep into the follicles. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of Polyethylene glycol (PEG)-coated nanorods (gold, 15×30 nm dimension) in cosmetically acceptable carrier, administered via ultrasound and massage, were observed within the follicle infundibulum at 200 um deep (FIG. 10A). Compositions of plasmonic nanoparticles (Silica-coated nanoplates) at lower concentration (10 O.D.), were apparent at 400-600 um deep in the follicle and in the sebaceous gland (open arrow), albeit at lower concentration than comparable particles in a similar cosmetic carrier at 100 O.D (FIG. 10B).

Assessment of Photothermal Destruction of Sebaceous Gland and Targeted Skin Structures.

Nanoparticle formulations are tested in ex vivo animal skin samples, ex vivo human skin samples, and in vivo human skin as described in Example 3. One can measure efficacy of photothermal destruction at the nanoparticle accumulation site by measuring thermal damage to sebocytes and reduction in sebum production in the treated sebaceous follicles. To assess photothermal destruction, human skin is first pre-treated with shaving to remove extruding hair, microdermabrasion (15 sec, medium setting) to remove hair-plugs and corneocytes, and chemical depilation to "open" follicle microwells for particle delivery. Skin is contacted with a 100 O.D. suspension of 810 nm resonant plasmonic nanoparticles (200 nm diameter), and is massaged for 3 minutes followed by ultrasound (1 MHz) for 5 min to drive particles deep into the follicles. The procedure is repeated for a total of 3 applications, and surface residue removed with 3-5 applications of alternating water and ethanol. Treated human skin samples are laser irradiated with 810 nm laser (40 J/cm$^2$, 30 ms, 5 pulses), and compared to laser only treated human skin. Human skin is biopsied, fixed in Zamboni's solution with 2% picric acid, and cryo-sectioned by freezing sliding microtome. Slides with mounted paraffin sections are deparaffinized and stained with hematoxylin and eosin (H&E). Histological sections are examined at various depths for markers of thermal damage and inflammation. Hematoxylin and eosin (H&E) is used to image skin and follicle microanatomy and indicate degeneration of hair shafts, atrophy of sebaceous glands, and cell vacuolization (indicating cellular damage). Nitro blue tetrazolium chloride (NBTC), a lactate dehydrogenase stain that is lost upon thermal injury to cells, may also be used to assess damage to keratinocytes vs. sebocytes. An intracellular stain, Oil-Red-O, may be used to determine lipid and sebum oil content in treated samples. Sebum excretion rates are measured on in vivo skin at 1-3 months follow up using sebum-absorbant tapes to demonstrate functional change in sebum flow. Clearance and prevention of acne lesions is measured by patient reported outcomes and counting acne lesions at 1-3 months follow up.

Example 5. Formulation of Thermoablative Plasmonic Nanoparticles for Vascular Ablation In one embodiment, formulations are prepared to maximize nanoparticle stability (degree of aggregation in solution), nanoparticle concentration, and nanoparticle absorbance (degree of laser-induced heating at different concentrations) once injected into the blood stream. Nanoparticles are generated as in Example 1 using an appropriate solvent. The mixture comprising a plurality of nanoparticles in water is concentrated to about 100-500 OD at peak absorbance and exchanged for a new solvent by liquid chromatography, a solvent exchange system, a centrifuge, precipitation, or dialysis. Typical exchange solvent is 0.15 mol/L NaCl, 0.1 mol/L Na phosphate buffer (pH 7.2).

Example 6. Use of Plasmonic Nanoparticles for Thermoablation of Component(s) of Vessels and Microvessels In one embodiment, nanoparticle-containing compositions are administered, typically intravascularly. Subsequent to such administration of plasmonic nanoparticles, a laser matched to the peak plasmonic resonance of the particles (e.g., 755 nm, 810 nm, or 1064 nm) is applied to heat nanoparticles and surrounding tissue. Pulse widths of 10-100 ns, 100 ns-1 ms, 1-10 ms, 10-100 ms, 100-1000 ms or continuous wave irradiation is used to achieve thermal heat gradients and localized heating in the vicinity of particle or particles of 20-200 nm. 200 nm-2 µm, 2-20 µm, 20-200 µm, 200 µm-2 mm. Thermal gradients of 20-200 nm are achieved from individual particles. Supra millimeter thermal gradients are achieved by the collective heat deposition of many particles in veins with diameters of several hundred microns or more. Irradiation is applied from 1 pulse to many pulses over seconds to minutes. A cooling device for epidermal layers is used concomitant to irradiation to reduce pain and prevent thermal damage elsewhere. Laser position, fluence, wavelength, angle of incidence, pattern of irradiation is modified to achieve irradiation of vessels at specific depths between 0-10 mm, while avoiding heating of non-target vasculature. Alternatively, laser or light is administered through fiber optic waveguide administered via a catheter to heat the particles in larger veins.

In one embodiment a flank of the tissue is irradiated with 2 W/cm$^2$, 810 nm, 1 cm beam diameter after injection of PEG-nanorods with peak plasmon resonance at 810 nm. Thermographic imaging is used to assess surface temperature of tissue immediately after irradiation.

Assessment of thermal damage to component(s) of vessels, microvessels, or capillaries. Thirty minutes after application, target vessels and the surrounding supporting tissue (e.g. skin) are removed. Biopsies are fixed in 10% paraformaldehyde, paraffin-embedded, and cut into 5-um sections on a microtome in transverse directions. Slides with mounted paraffin sections are deparaffinized and stained with hematoxylin and eosin (H&E) or silver enhancement staining. Using H&E staining and light microscopy, one or several vessels, microvessels, and capillaries can be imaged. Scoring is performed for visible thermal damage of the vessel structures. Additionally, vessel staining (e.g. CD31 stain) is performed to clearly identify vascular structures within tissue samples.

Example 7. Determination of Efficiency of Conversion of Light to Thermal Energy

Figure 11A:
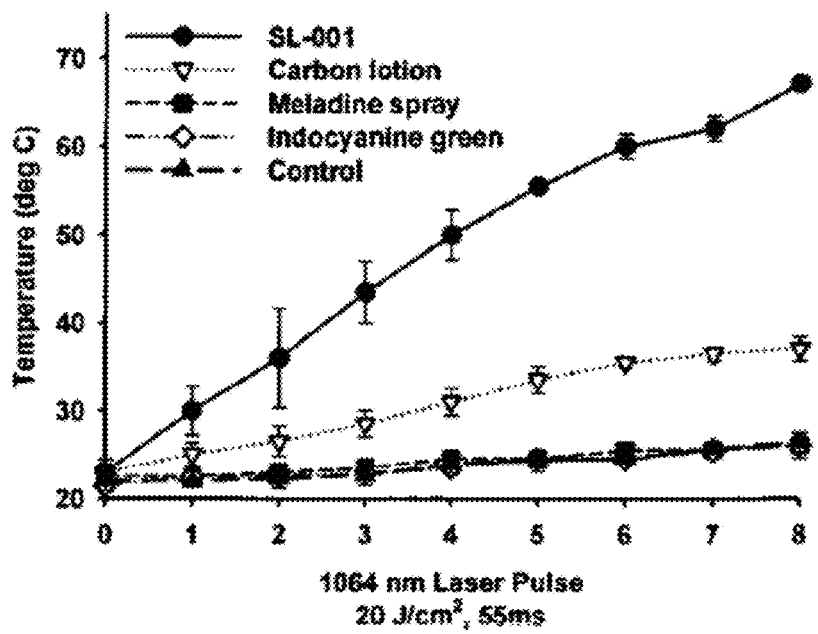
FIG. 11A is illustrative of temperature profiles of certain embodiments of plasmonic nanoparticle formulations compared to other commercial and research chromophores as a function of number of pulses from a 20 J/cm² 1064 nm laser (55 ms pulses).
Figure 11B:
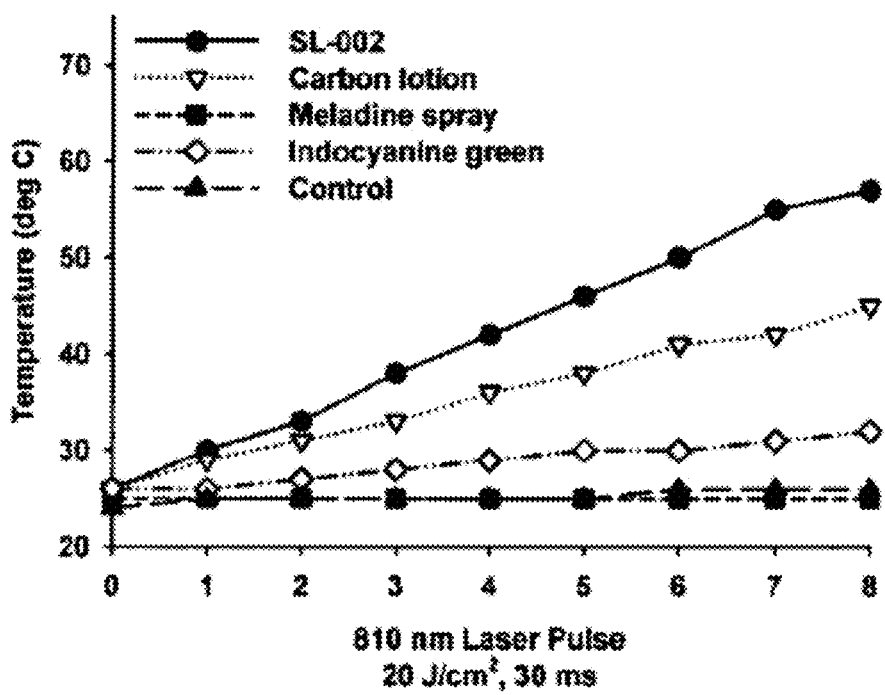
FIG. 11B is illustrative of temperature profiles of certain embodiments of plasmonic nanoparticle formulations compared to other commercial and research chromophores as a function of number of pulses from a 20 J/cm² 810 nm laser (30 ms pulses).

In one embodiment, a suspension of plasmonic nanoparticles (silica-coated nanoplates having a diameter of about 100-200 nm, as described here) was prepared by formulating the plasmonic nanoparticles in 20% propylene glycol in water to a concentration of about 1000 O.D., and the ability of this suspension to convert laser light to thermal energy was determined. Available commercial and research products, e.g., stock solutions of carbon lotion (20-200 mg/ml carbon, TelsarSoftLight), Meladine spray (1 mg/ml melanin, Creative Technologies), Indocyanine green (5 mg/ml in water, Sigma Aldrich), and vehicle control (20% propylene glycol in water) were also tested. All solutions were diluted 1:1 000 from their indicated stock solution concentration, loaded at 90 µl per well into a 96-well plate, and baseline temperatures were measured by K thermocouple with micrometer (ExTech Instruments, Waltham Mass.) and recorded. Solutions were then irradiated with repeated laser pulses at various wavelengths (e.g., 1064 nm, 810 nm, and 755 nm), fluence (e.g., 10, 20, and 30 J/cm2) and pulse sequence parameters (e.g., 30 ms and 55 ms). Following each sequential laser pulse, up to a total of 8 pulses, solution temperatures were measured and recorded. As shown in FIGS. 11A-11B, a series of plasmonic nanoparticle (PNP) formulations (labeled SL-001 and SL-002) exhibited ultra-high absorption compared to existing commercial and research chromophores. (FIG. 11A, B) Rate of temperature increase over sequential laser pulses for PNP formulation SL-001 (FIG. 11A, closed circle), resonant at 1064 nm laser wavelength, upon irradiation with 1064 nm laser (A), and SL-002 (FIG. 11B closed circle), resonant at 810 nm laser wavelength, upon irradiation with 810 nm laser (B). Control solutions are as follows: Carbon lotion (open triangle), Meladine spray (closed square), Indocyanine green (open diamond), and 20% propylene glycol (closed triangle). All solutions were diluted 1:1000 from stock clinical concentration for laser irradiation and temperature measurements. For A, n=2 and error bars are s.d. of the mean.

Example 8. Quantitation of Nanoparticle Delivery into Target Tissues

Figure 12A:
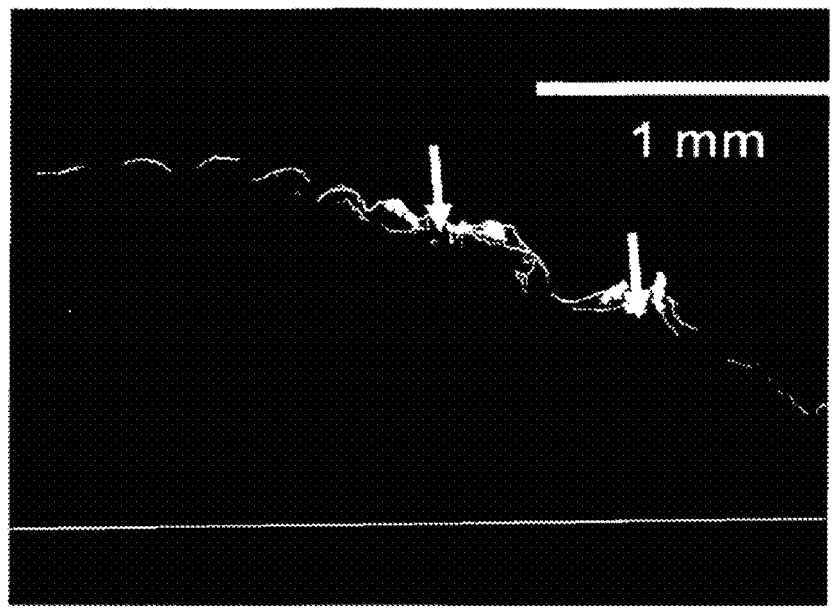
FIGS. 12A and 12B are images of embodiments of nanoparticle formulations in porcine skin.
Figure 12B:
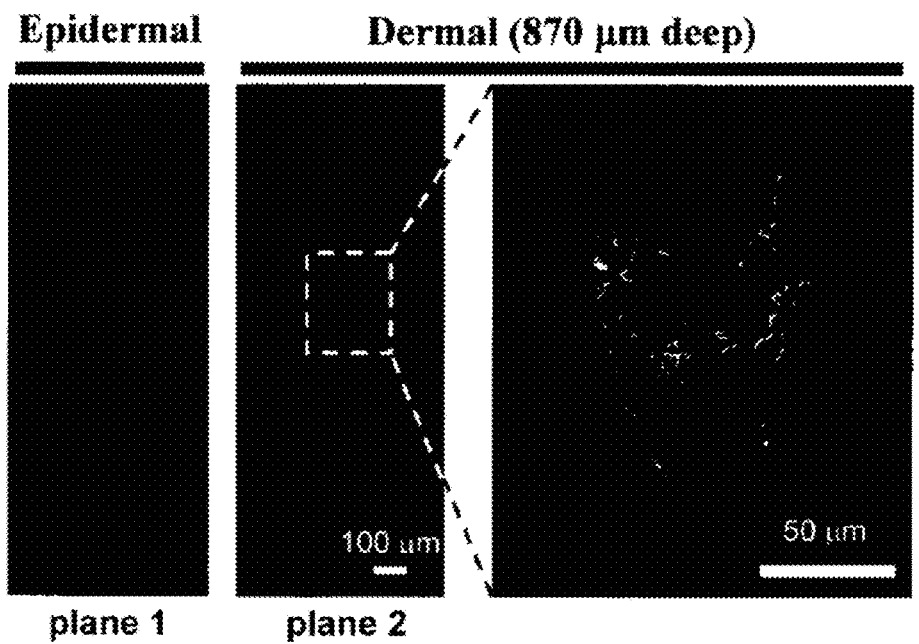

In one embodiment, red fluorescent nanoparticles (Corpuscular Inc., Cold Spring, N.Y.) were contacted with isolated porcine skin explants as follows. A 2.5 mg/ml solution of SiO$_2$, 200 nm diameter, 548 nm emission particles in 20% propylene glycol was pipetted onto the skin surface and mechanically massaged into the tissue explant. An ethanol wipe was used to remove non-penetrating particles. As shown in FIGS. 12A-12B, the provided formulations of nanoparticles (NPs) deeply and specifically penetrate ex vivo porcine skin. FIG. 12A demonstrates representative survey fluorescence image of porcine skin, treated with red fluorescent NPs and histologically sectioned. Red (light contrast) NPs are imaged after penetrating the hair follicle infundibulum (arrows) and deep follicle, but not in the underlying dermis. FIG. 12B shows representative confocal images show red NPs within superficial and deep follicle (–870/–tm) at high and low magnification. Green (dark contrast) is tissue autofluorescence (488 nm emission). Scale bars as labeled 1 mm (A), 10 µm (B, left), 50 µm (B, right).

Figure 13A:
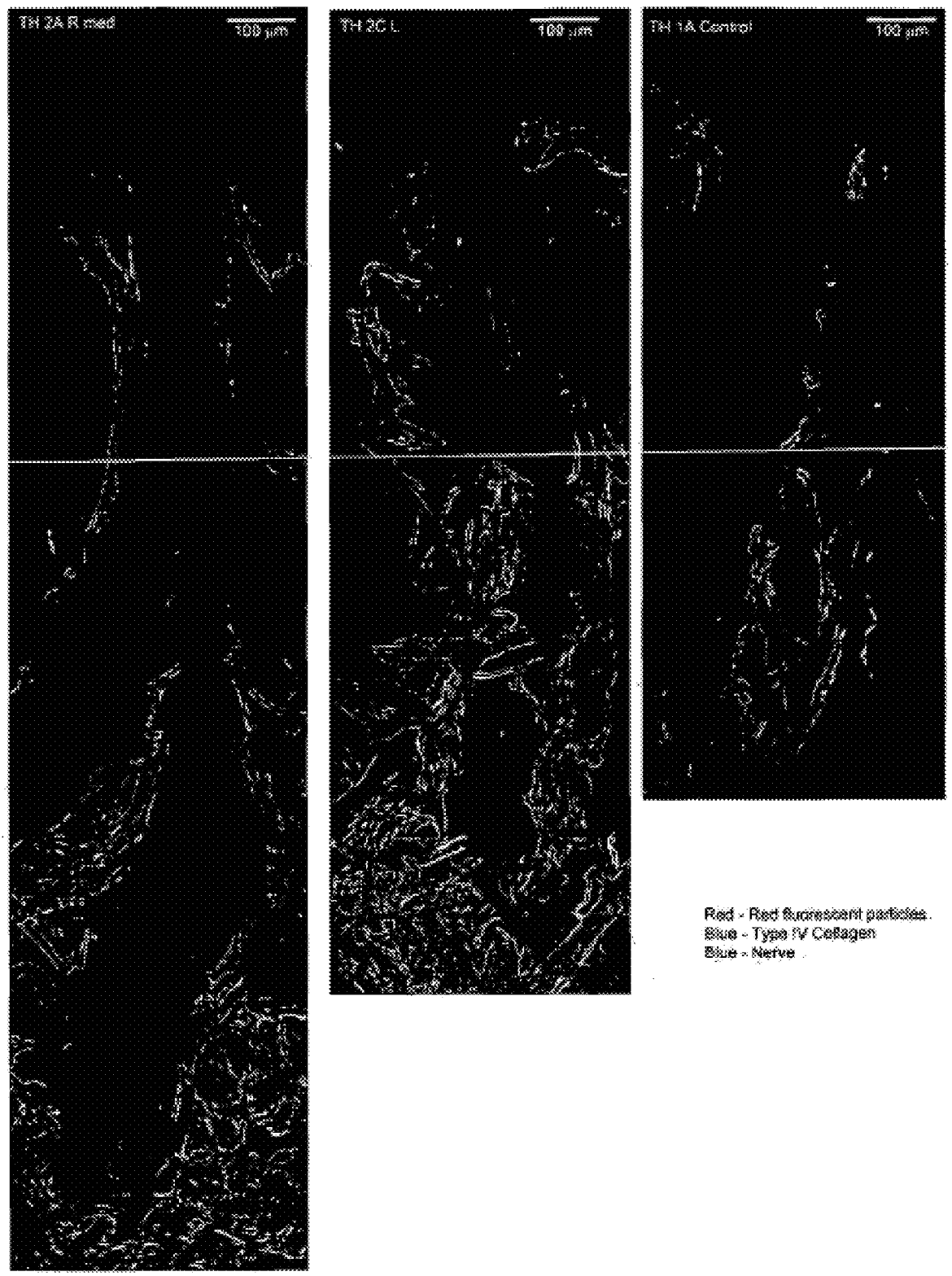
FIGS. 13A and 13B are images of biopsies taken from in vivo-treated human skin, which were sectioned and immunostained for skin markers, with various embodiments of nanoparticles.
Figure 13B:
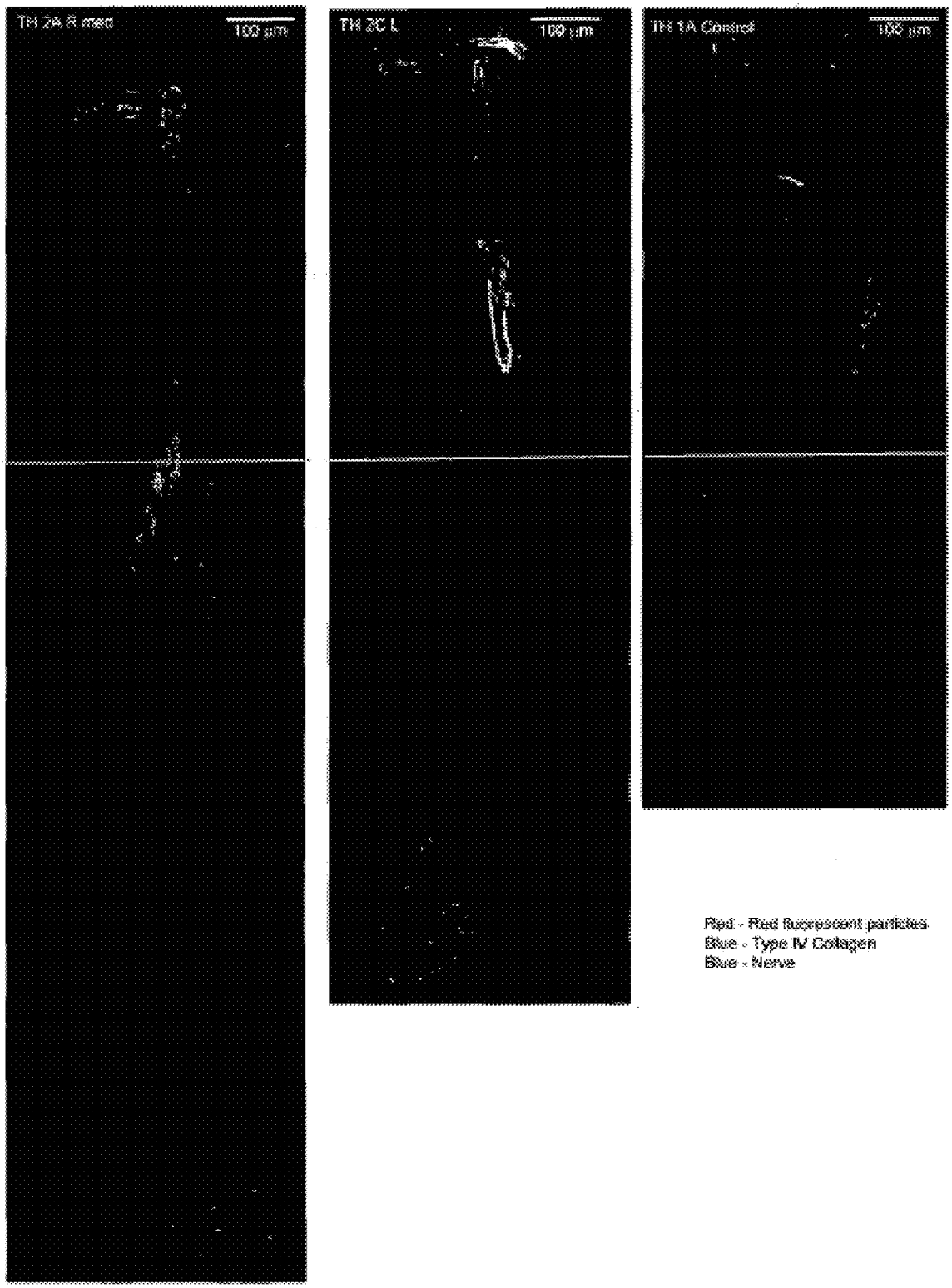

Further, formulations of nanoparticles (NPs) with silica coating deeply and specifically penetrate in vivo human skin. A region of an upper arm of a male human subject having skin Type 3 was treated with the red nanoparticles essentially as described above. Shown in FIGS. 13A and 13B are representative confocal images of biopsies taken from the in vivo-treated human skin, which were sectioned and immunostained for skin markers. Left—'TH 2A R med' sample shows red hair follicle fluorescence after red NP application with massage, ultrasound, and no pre-depilation with waxing; Middle 'TH 2C L' sample shows red hair follicle fluorescence after red NP application with massage, ultration, and pre-depilation with waxing; Right—'TH 1A Control' shows background red autofluorescence of hair follicle. FIG. 13A is 3 color image where red is NPs, blue is collagen IV (staining basement membrane) and green is PGP 9.5 (staining nerve fiber). FIG. 13B shows red channel only in black and white. Scale bars as labeled 100 µm.

Example 9. Treatment of Atrophic Scars with Needle Nose Tube Dispenser

In one embodiment, the following treatments were administered to the face of a patient using a ND:YAG laser and a composition containing silica-coated silver plasmonic nanoplates delivered from a needle-nose tube dispenser. Silica-coated silver plasmonic nanoplates were synthesized to have a resonant absorption peak at 1050 nm and formulated in a cosmetic carrier containing water, propylene glycol, sodium dodecyl sulfate, aristoflex AVC, and PE9010. Particle concentration was brought to between $10^{12}$ to $10^{13}$ particles per ml to achieve an optical density of 100 O.D. at 1050 nm. The solution was dispensed from a needle nose tube dispenser into an ice pick acne scar and a box car chicken pox scar with diameters of ~1 mm and ~3 mm respectively and a cosmetic sponge was used to wipe away/soak up material that contacted the skin outside of the target region. Presence of the solution on and within the scars was visualized by its green hue. Electromagnetic radiation (light) was administered to the treatment areas after application of solution to the skin using an ND:YAG laser operating at a 5 ms pulse width, 7 mm spot size, and a fluence of 15 J/cm$^2$. Two treatments were administered to each scar at 1 week apart.

Figure 14:
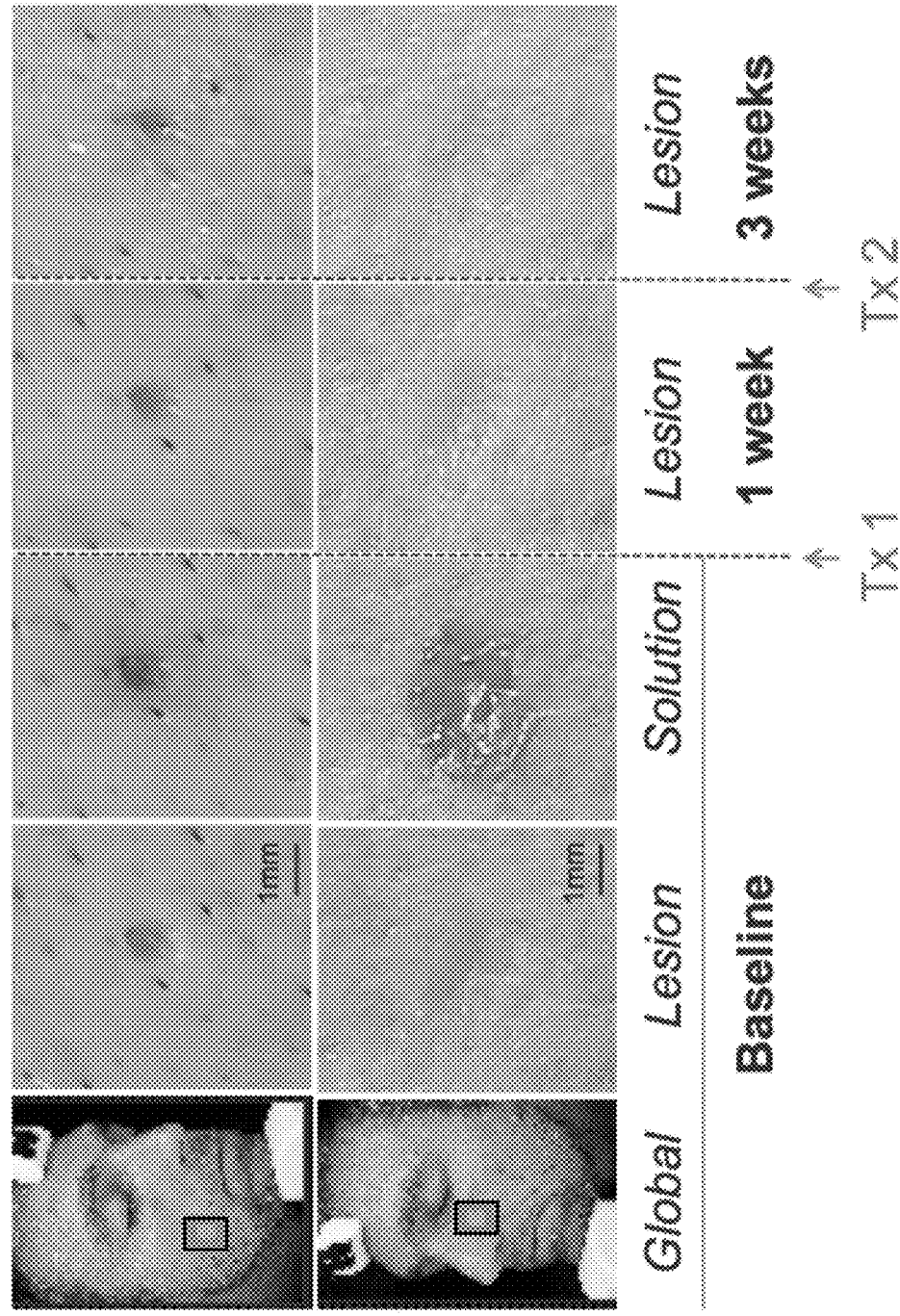
FIG. 14 includes images of an embodiment of a treatment of atrophic scars with a laser and photoactive material delivered to small target regions of dermal scar tissue.

Treatment areas initially showed minimal pinkness of the skin, with no purpura. After 24 hours the treated spots turned dark immediately around the target region, showing increased pigmentation. Within 3-5 days of treatment the darker spots scaled off and the skin returned to a normal appearance. After two weeks from the second treatment the diameter, depth, and prominence of both treated scars was noticeably reduced. (See FIG. 1) The series of images at the top of FIG. 14 shows an ice pick acne scar from baseline to 3 weeks post initial treatment. Selective delivery of photoactive material (silica-coated silver plasmonic nanoparticles) is visualized at baseline (Solution). The series of images at the bottom of FIG. 14 shows a box car chicken pox scar from baseline to 3 weeks post initial treatment. Selective delivery of photoactive material (silica-coated silver plasmonic nanoparticles) is visualized at baseline (Solution).

Example 10. Treatment of Atrophic Scars by Large Region Application and Selective Removal In one embodiment, the following treatments were administered to the face of a patient using a 1064 nm ND:YAG laser and a composition containing silica-coated silver plasmonic nanoplates delivered from a topical syringe. Silica-coated silver nanoplates were synthesized to have a resonant absorption peak near 1050 nm and formulated in a cosmetic carrier containing water, propylene glycol, sodium dodecyl sulfate, aristoflex AVC, and PE9010. Particle concentration was brought to between $10^{12}$ to $10^{13}$ particles per ml to achieve an optical density of 100 O.D. at 1050 nm. The solution was dispensed from a topical syringe to the cheeks of a patient with multiple atrophic acne scars to disperse the solution into each scar. A wet cloth was used to remove photoactive compound on the surface of the skin, but not localized in the atrophic lesions. Presence of the solution on and within the scars was visualized by its dark hue resulting in a speckled pattern on the face. Electromagnetic radiation (light) was administered to the treatment areas after application of solution to the skin using a 1064 nm ND:YAG laser operating at a 5 ms pulse width, 7 mm spot size, and a fluence of 15 J/cm$^2$. Six treatments were administered at 2 weeks apart.

Treatment areas initially showed minimal pinkness of the skin, with no purpura after each treatment. After 24 hours the treated spots turned dark immediately around the target region, showing increased pigmentation. Within 3-5 days of each treatment the darker spots scaled off and the skin returned to a normal appearance. After two weeks from the sixth treatment the diameter, depth, and prominence of atrophic scars was significantly reduced.

Example 11. Treatment of Atrophic Scars with Nanoshells

In one embodiment, the following treatments were administered to the face of a patient using a 755 nm Alexandrite laser and a composition containing PEG-coated gold plasmonic nanoshells delivered from a topical syringe. PEG-coated gold plasmonic nanoshells were synthesized to have a resonant absorption peak near 750 nm and formulated in a cosmetic carrier containing water, propylene glycol, aristoflex AVC, and PE9010. Particle concentration was brought to approximately $3 \times 10^{11}$ particles per ml to achieve an optical density of 100 O.D. at 750 nm. The solution was dispensed from a needle-nose applicator to individual atrophic acne scars on a patients phase and a sponge was used to wipe away/soak up material in non-target regions. Presence of the solution on and within the scars was visualized by its dark hue resulting in a speckled pattern on the face. Electromagnetic radiation (light) was administered to the treatment areas after application of solution to the skin using a 755 nm Alexandrite laser operating at a 5 ms pulse width, 7 mm spot size, and a fluence of 15 J/cm$^2$. Six treatments were administered at 2 weeks apart.

Treatment areas initially showed minimal pinkness of the skin, with no purpura after each treatment. After 24 hours the treated spots turned dark immediately around the target region, showing increased pigmentation. Within 3-5 days of each treatment the darker spots scaled off and the skin returned to a normal appearance. After two weeks from the sixth treatment the diameter, depth, and prominence of atrophic scars was significantly reduced.

Example 12. Treatment of Pigmented Lesions/Freckles with Silver Nanoplates

In one embodiment, the following treatments were administered to the arm of a patient using a 755 nm alexandrite laser and a composition containing silica-coated silver plasmonic nanoplates delivered from a topical syringe. Silica-coated silver plasmonic nanoplates were synthesized to have a resonant absorption peak at 750 nm and formulated in a cosmetic carrier containing water, propylene glycol, sodium dodecyl sulfate, aristoflex AVC, and PE9010. Particle concentration was adjusted to between $10^{12}$ to $10^{13}$ particles per ml to achieve an optical density of 100 O.D. at 750 nm. The solution was dispensed from a needle nose applicator to 3 individual sun spots/freckles on the arm of a patient. Presence of the solution on the freckles was visualized by its blue hue resulting in a speckled pattern on the arm. Electromagnetic radiation (light) was administered to the treatment areas after application of solution to the skin using an 755 nm Alexandrite laser operating at a 0.5 ms, 5 ms, and 50 ms pulse width for each spot respectively, 7 mm spot size, and a fluence of 15 J/cm$^2$.

Treatment areas initially showed minimal pinkness of the skin, with no purpura after each treatment. Pain and pinkness was the least in the area treated with the 0.5 ms pulse width. After 24 hours 5 ms and 50 ms treated spots turned dark immediately around the target region, showing increased pigmentation. Within 3-5 days of each treatment the darker spots scaled off and the skin returned to a normal appearance. Within two weeks significant reduction in color/darkness of the pigmented lesions/freckles was observed for spots treated with 5 ms and 50 ms pulse widths. The color/darkness of the pigmented lesion treated with 0.5 ms pulse was reduced, but not as prominently as the areas treated with 5 ms and 50 ms pulse widths.

Example 13. Treatment of Pigmented Lesions/Freckles with Nanorods

In one embodiment, the following treatments were administered to the arm of a patient using a 755 nm alexandrite laser and a composition containing PEG-coated gold plasmonic nanorods delivered from a topical syringe. PEG-coated gold plasmonic nanorods were synthesized to have a resonant absorption peak at 750 nm and formulated in a cosmetic carrier containing water, propylene glycol, sodium dodecyl sulfate, aristoflex AVC, and PE9010. Particle concentration was adjusted to achieve an optical density of 50 O.D. at 750 nm. The solution was dispensed from a needle nose applicator to 3 individual sun spots/freckles on the arm of a patient. Presence of the solution on the freckles was visualized by its dark hue resulting in a speckled pattern on the arm. Electromagnetic radiation (light) was administered to the treatment areas after application of solution to the skin using an 755 nm Alexandrite laser operating at a 0.5 ms, 5 ms, and 50 ms pulse width for each spot respectively, 7 mm spot size, and a fluence of 15 J/cm$^2$.

Treatment areas initially showed minimal pinkness of the skin, with no purpura after each treatment. Pain and pinkness was least in the area treated with the 0.5 ms pulse width. After 24 hours 5 ms and 50 ms treated spots turned dark immediately around the target region, showing increased pigmentation. Within 3-5 days of each treatment the darker spots scaled off and the skin returned to a normal appearance. Within two weeks significant reduction in color/darkness of the pigmented lesions/freckles was observed for spots treated with 5 ms and 50 ms pulse widths. The color/darkness of the pigmented lesion treated with 0.5 ms pulse was reduced, but not as prominently as the areas treated with 5 ms and 50 ms pulse widths.

Example 14. Treatment of Pigmented Lesions/Freckles with Carbon Nanoparticles

In one embodiment, the following treatments were administered to the arm of a patient using a 1064n ND:YAG laser and a composition containing carbon nanoparticles. Carbon nanoparticles were coated with polyvinyl pyrrolidone and formulated in a cosmetic carrier containing water, propylene glycol, sodium dodecyl sulfate, aristoflex AVC, and PE9010. Particle concentration was brought to 1-5 mg per ml to achieve an optical density of 100 O.D. at 1050 nm. The solution was dispensed from a needle nose applicator to 3 individual sun spots/freckles on the arm of a patient. Presence of the solution on the freckles was visualized by its black hue resulting in a speckled pattern on the arm. Electromagnetic radiation (light) was administered to the treatment areas after application of solution to the skin using an 1064 nm ND:YAG laser operating at a 0.5 ms, 5 ms, and 50 ms pulse width for each spot respectively, 7 mm spot size, and a fluence of 15 J/cm$^2$.

Treatment areas initially showed minimal pinkness of the skin, with no purpura after each treatment. Pain and pinkness was least in the area treated with the 0.5 ms pulse width. After 24 hours 5 ms and 50 ms treated spots turned dark immediately around the target region, showing increased pigmentation. Within 3-5 days of each treatment the darker spots scaled off and the skin returned to a normal appearance. Within two weeks significant reduction in color/darkness of the pigmented lesions/freckles was observed for spots treated with 5 ms and 50 ms pulse widths. The color/darkness of the pigmented lesion treated with 0.5 ms pulse was reduced, but not as prominently as the areas treated with 5 ms and 50 ms pulse widths.

Example 15. Treatment of Striae

The following treatments were administered to the abdomen of a patient using a 1064 nm ND:YAG laser and a composition containing silica-coated silver plasmonic nanoplates delivered from a topical syringe. Silica-coated silver plasmonic nanoplates were synthesized to have a resonant absorption peak at 1050 nm and formulated in a cosmetic carrier containing water, propylene glycol, sodium dodecyl sulfate, aristoflex AVC, and PE9010. Particle concentration was brought to between $10^{12}$ to $10^{13}$ particles per ml to achieve an optical density of 100 O.D. at 1050 nm. The solution was dispensed from a needle nose applicator along multiple lines of striae on a patient. Presence of the solution on the striae was visualized by its green hue. Electromagnetic radiation (light) was administered to the treatment areas after application of solution to the skin using an 1064 nm ND:YAG laser operating at a 5 ms pulse width, 7 mm spot size, and a fluence of 15 J/cm$^2$. Three treatments were administered at 2 weeks apart.

Treatment areas initially showed minimal pinkness of the skin, with no purpura after each treatment. After 24 hours the treated areas turned dark immediately around the target region, showing increased pigmentation. Within 3-5 days of each treatment the darker spots scaled off and the skin returned to a normal appearance. Appearance of striae was noticeably reduced two weeks after the third treatment.

Example 16. Composition Delivery Devices

In an experiment, an embodiment of a composition 100 of nanoparticles was distributed to various target tissue depths with various embodiments of delivery devices 200. In the experiment, an animal skin model (pig ear) comprising hair follicles and sebaceous glands in an epidermis was used to model skin treatment with a composition 100. In various embodiments, ultrasound and/or other sonic forces, mechanical vibrations, hair shaft manipulation (including pulling), physical force, thermal manipulation, and other treatments are utilized to improve entry of a composition 100 of light-absorbing nanoparticles into hair follicles and/or sebaceous glands. Mechanical vibration massage improves follicular penetration through hair shaft 'pumping' mechanisms, while ultrasound enhances transdermal drug delivery through temporary disruption of the skin's lipid bilayer, bubble formation, liquid microstreaming, jetting, streaming, heating, and/or cavitation. A composition 100 of plasmonic nanoparticles was contacted with the skin model to produce a semi-quantitative assay for measuring and optimizing delivery efficacy. Through experimentation, evaluation of formulations of the composition 100 in conjunction with testing of individual and/or combinations of embodiments of delivery devices 200.

Figure 15:
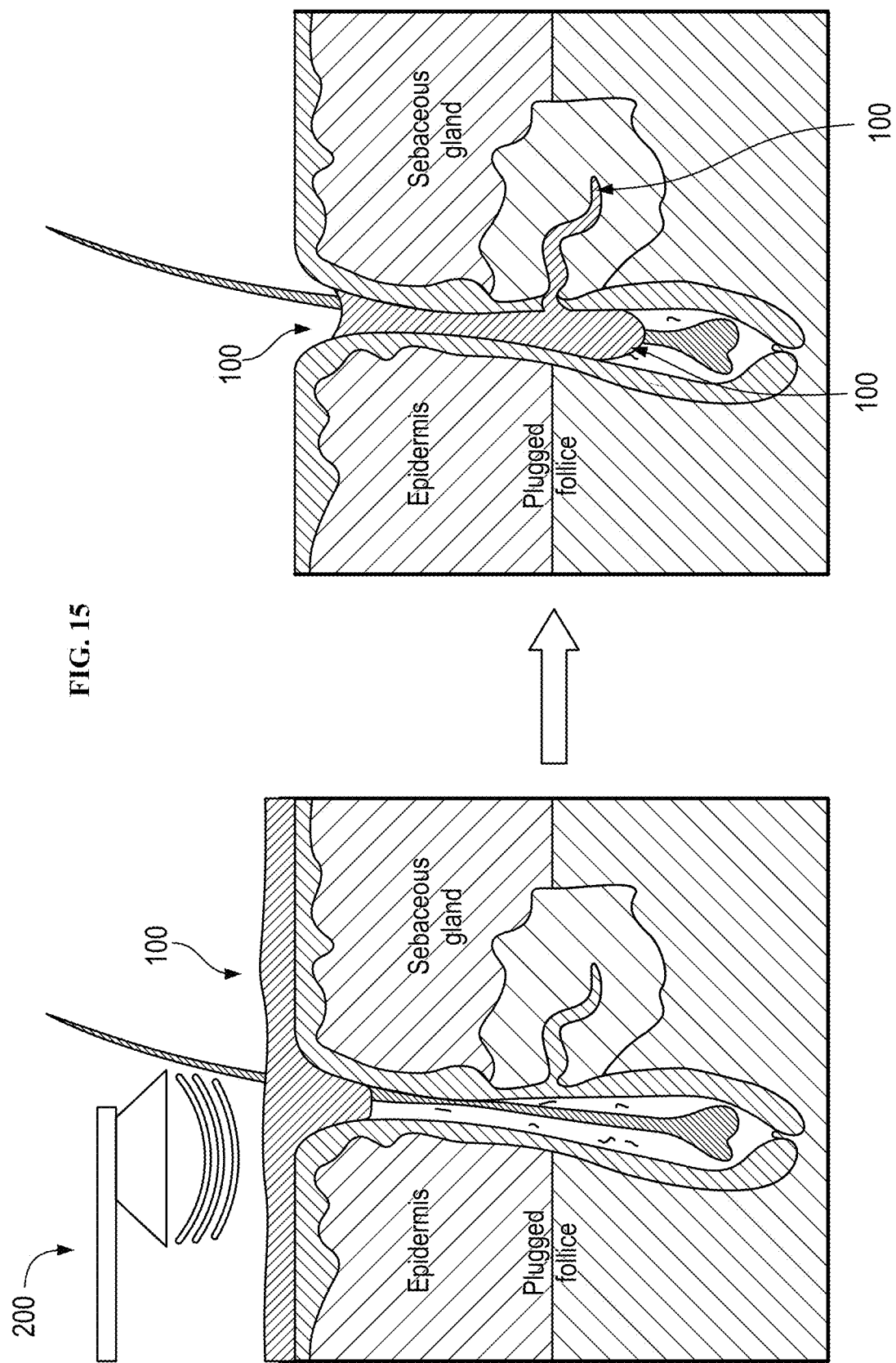
FIG. 15 is a schematic side view of a composition being distributed from a skin surface to a target in the tissue with a delivery device according to an embodiment of the invention.
Figure 16:
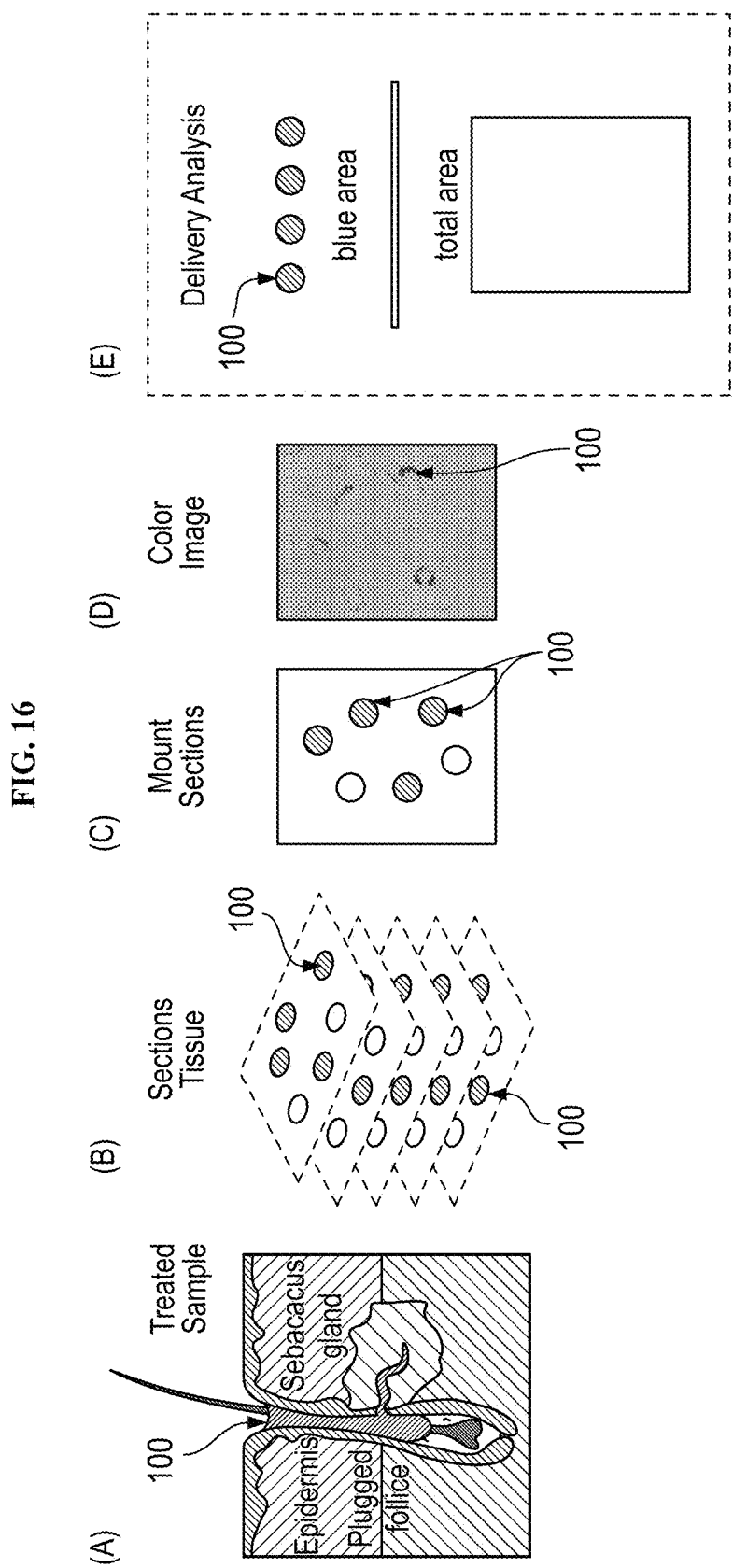
FIG. 16 is a schematic of an experimental process for measuring the distribution of a composition with various embodiments of delivery devices in tissue.

FIG. 15 illustrates an embodiment of a delivery device 200 distributing a composition 100 from a skin surface to a target skin depth. In the illustrated FIG. 15, the target skin comprises a hair follicle and/or a sebaceous gland. In one embodiment, FIG. 15 is a schematic side view of a composition being distributed from a skin surface to a target in the tissue with a delivery device according to an embodiment of the invention (left side). The formulation (100) is applied to the skin followed by the delivery device (200), e.g., massage or ultrasound treatment. (right side) After wiping away excess formulation from the surface of the skin, composition (100) is localized only within the structures of the hair follicle (e.g., infundibulum, lumen, sebaceous gland) and no longer on the surface of the epidermis. In one embodiment, the follicle is a plugged follicle. Three embodiments of delivery devices 200 were used. For each of the delivery devices 200, a composition 100 was applied to the surface of the skin model. The delivery device 200 was activated to move the composition 100 from the skin surface to the target tissue depth. As illustrated at the embodiment at FIG. 16, the skin model was sectioned into 40 micron slices, which were then mounted and imaged using a high resolution color scanner. In one embodiment, FIG. 16 includes: (A) an illustration of the skin after targeted delivery of the composition (100). (B) Using common histological protocols, a smaller section of the skin that was treated is fixed and sectioned into horizontal slices between 10-60 microns thick. Areas where the formulation (100) was delivered can be observed within the individual hair follicles contained within these slices. (C) The individual tissue sections are mounted for imaging. (D) Each tissue section is imaged using a high resolution optical scanner. The formulation (100) can be observed (blue color) without staining. (E) Analysis of percent delivery is calculated as the ratio of the formulation (blue color) to the total area of the section and expressed as a percentage.

The mounted section of skin is imaged. In one embodiment, the composition 100 is blue. The images are analyzed measuring the total blue area as a ratio to the total section area. Delivery measurements are quantified as the ratio of blue area (composition 100) over the total area. In various embodiments, the composition 100 can be any color.

FIG. 17 is a table summarizing experimental results using three embodiments of delivery devices 200 to deliver a composition 100 to various depths in tissue according to various embodiments. The vibraderm (210) is an adjustable vibration device applying a nominal 80 Hz longitudinal vibration. The Acoustic Horn/Sonotrode (220) is a 30-40 kHz ultrasound device employing an acoustic horn or sonotrode to apply the ultrasonic energy into the composition. Ultrasound from an acoustic horn or sonotrode is focused in the volume immediately surrounding the horn or sonotrode and therefore produces cavitation mostly in the formulation and at the surface of the skin. The flat transducer (230) is a 30-40 kHz ultrasound device employing a flat head to deliver the ultrasonic energy into the formulation. Ultrasound from a flat transducer is "unfocused" in that it produces cavitation at various distances away from the ultrasound head. The first delivery device 210 is a Vibraderm with 80 Hz longitudinal vibration. The second delivery device 220 is a 30 kHz-40 kHz low frequency ultrasound device with a sonotrode that operates at a frequency about 32.4 kHz pulsed ultrasound with surface localized energy configured to induce cavitation (IMPACT, Alma Lasers). The third delivery device 230 is a low frequency ultrasound device that operates at a frequency of 40 kHz non-pulsed ultrasound configured to induce cavitation from an unfocused transducer (GS8.0). The first delivery device 210 uses a mechanical mixing mechanism resulting in a 4% of total skin cross-section ratio measurement of composition 100 at a depth of 500 micrometers in porcine ear skin, with a maximum delivery depth of about 1000 microns in porcine ear skin. The second delivery device 220 uses a cavitation mechanism resulting in a 12% of total skin cross-section ratio measurement of composition 100 at a depth of 500 micrometers in porcine ear skin, with a maximum delivery depth of about 1500 microns in porcine ear skin. The third delivery device 230 uses a cavitation mechanism with an unfocused transducer resulting in a variable 4-12% of total skin cross-section ratio measurement of composition 100 at a depth of 500 micrometers in porcine ear skin, with a maximum delivery depth of about 1000 microns in porcine ear skin.

FIG. 18 illustrates images of delivery of composition 100 to skin models (pig ears) using three delivery techniques: low frequency ultrasound (at 40 kHz for 1 minute), massage by hand (for 1 minute), and through incubation on the skin surface (placement of the composition 100 on the skin surface for 5 minutes). The top panel contains 5× brightfield images looking down at the surface of intact skin models immediately following the delivery of an embodiment of the composition. In the leftmost image of the top panel, low frequency ultrasound, the formulation (100) is observed to be localized within several hair follicles. In the middle and rightmost images of the top panel, massage by hand and incubate on skin respectively, no delivery is observed. The lower panel contains 20× brightfield images of vertical cross sections of the skin. The cross sections are cut to expose an individual hair follicle. In the leftmost image of the bottom panel, low frequency ultrasound, the formulation (100) is observed clearly localized within the infundibulum, sebaceous gland, and the lumen of the hair follicle. In the middle and rightmost images of the bottom panel, massage by hand and incubate on skin respectively, no delivery is limited to the uppermost region of the infundibulum of the hair follicles. As illustrated in the images, the composition 100 penetrates the deepest with the low frequency ultrasound device, with the composition 100 delivered to the infundibulum (INF), sebaceous gland (SG) and the hair follicle lumen (HFL). As illustrated in the images, the composition 100 penetrates to the infundibulum (INF) with hand massage. As illustrated in the images, the composition 100 penetrates near the skin surface.

Figure 19:
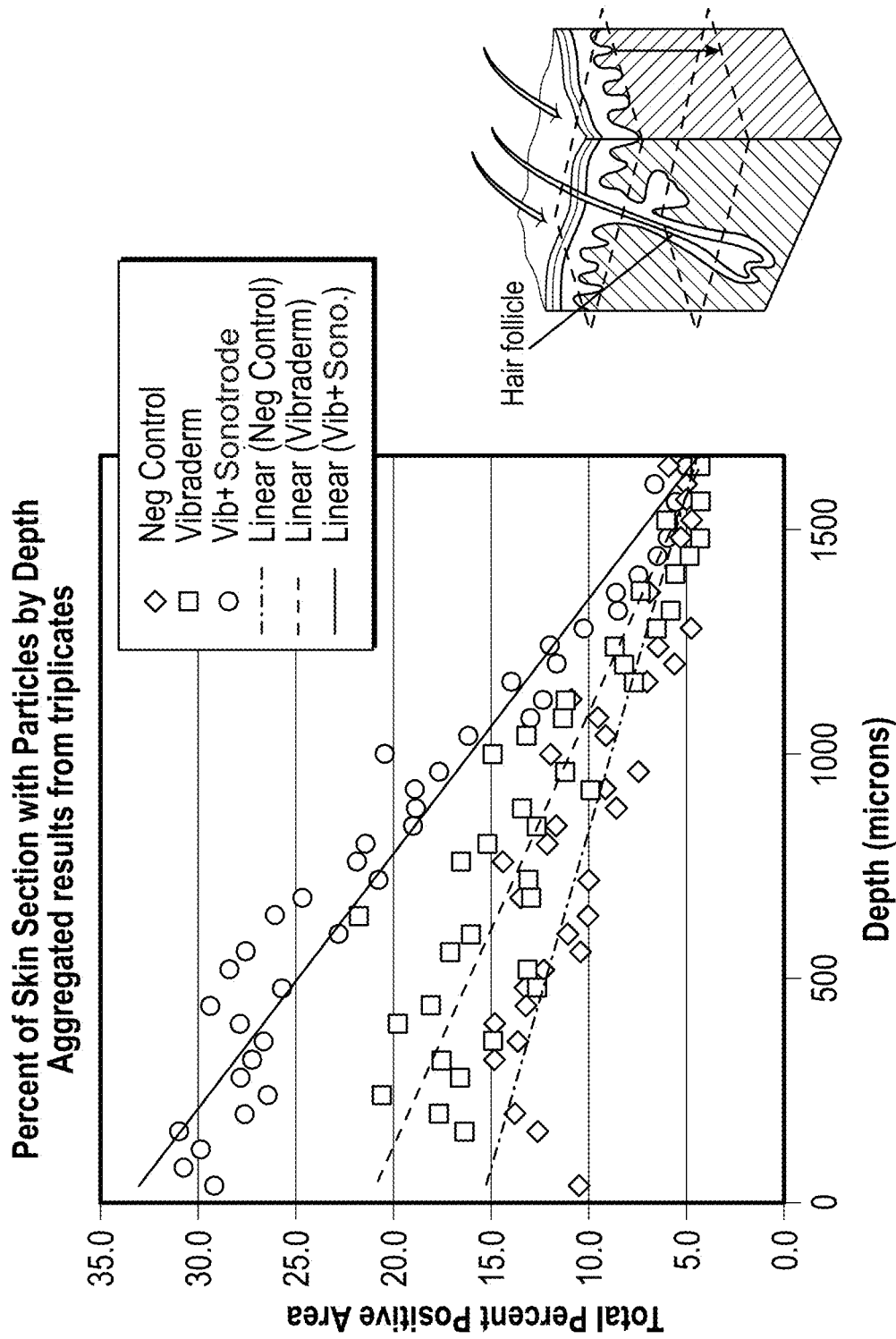
FIG. 19 is illustrative of a graph of experimental measurements of percentage of composition delivery to an area at a depth in tissue with various delivery devices according to embodiments of the invention.
Figure 20:
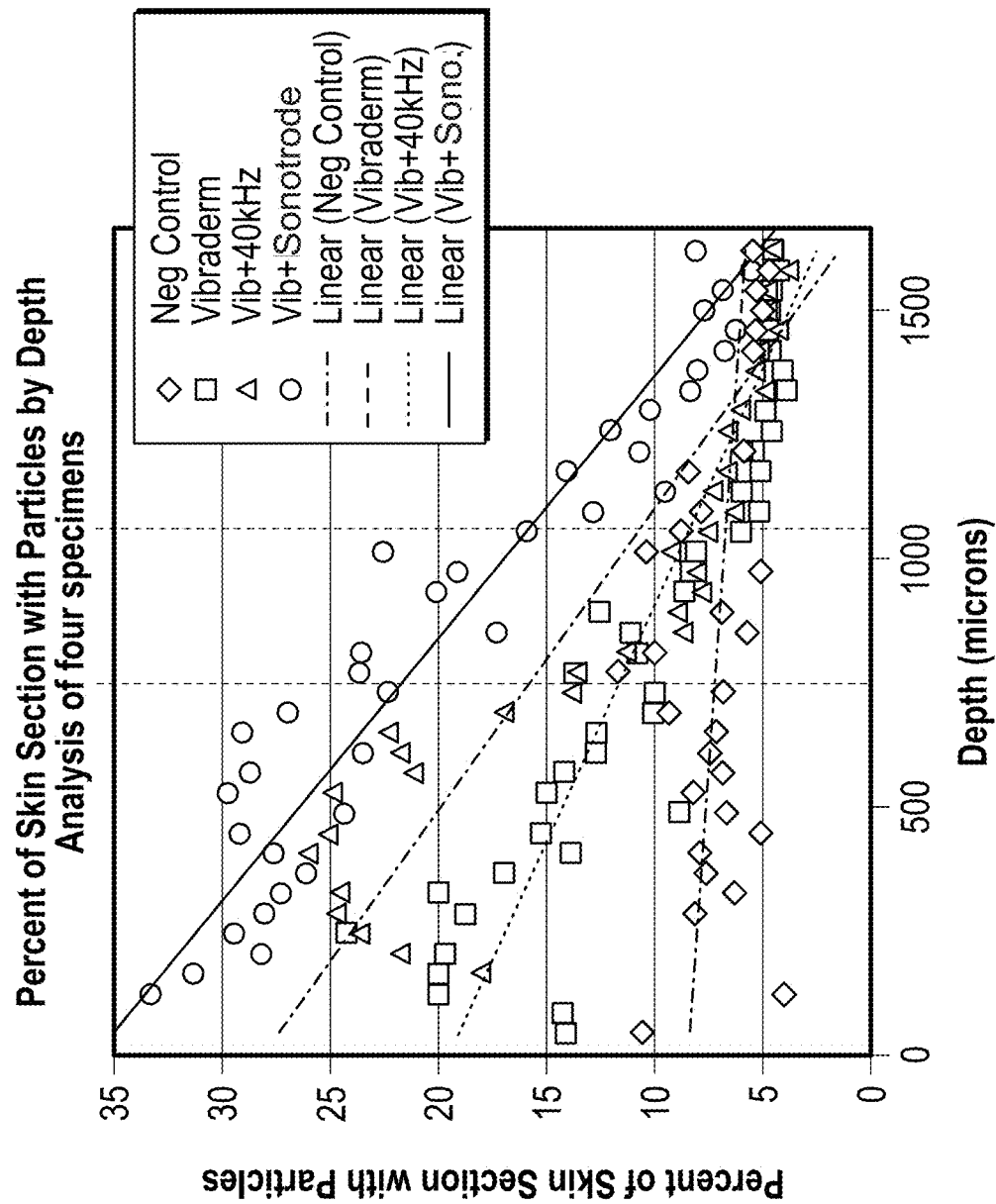
FIG. 20 is illustrative of a graph of experimental measurements of percentage of composition delivery to an area at a depth in tissue with various delivery devices according to embodiments of the invention.

FIG. 19 is a graph plotting data from the experiment, showing the total percent positive area on the y-axis, and depth in microns on the x-axis. Plotted are a negative control (incubation on the skin surface without a delivery device 200), the first delivery device 210 (Vibraderm), and a combination of both the first delivery device 210 (Vibraderm) and the second delivery device 220 (30 kHz-40 kHz ultrasound device with a sonotrode). FIG. 20 is a graph plotting data from the experiment, showing the total percent positive area on the y-axis, and depth in microns on the x-axis. Plotted are a negative control (incubation on the skin surface without a delivery device 200), the first delivery device 210 (Vibraderm), a combination of both the first delivery device 210 (Vibraderm) and the third delivery device 230 (36 kHz non-pulsed ultrasound), and a combination of both the first delivery device 210 (Vibraderm) and the second delivery device 220 (30 kHz-40 kHz ultrasound device with a sonotrode).

Figure 21:
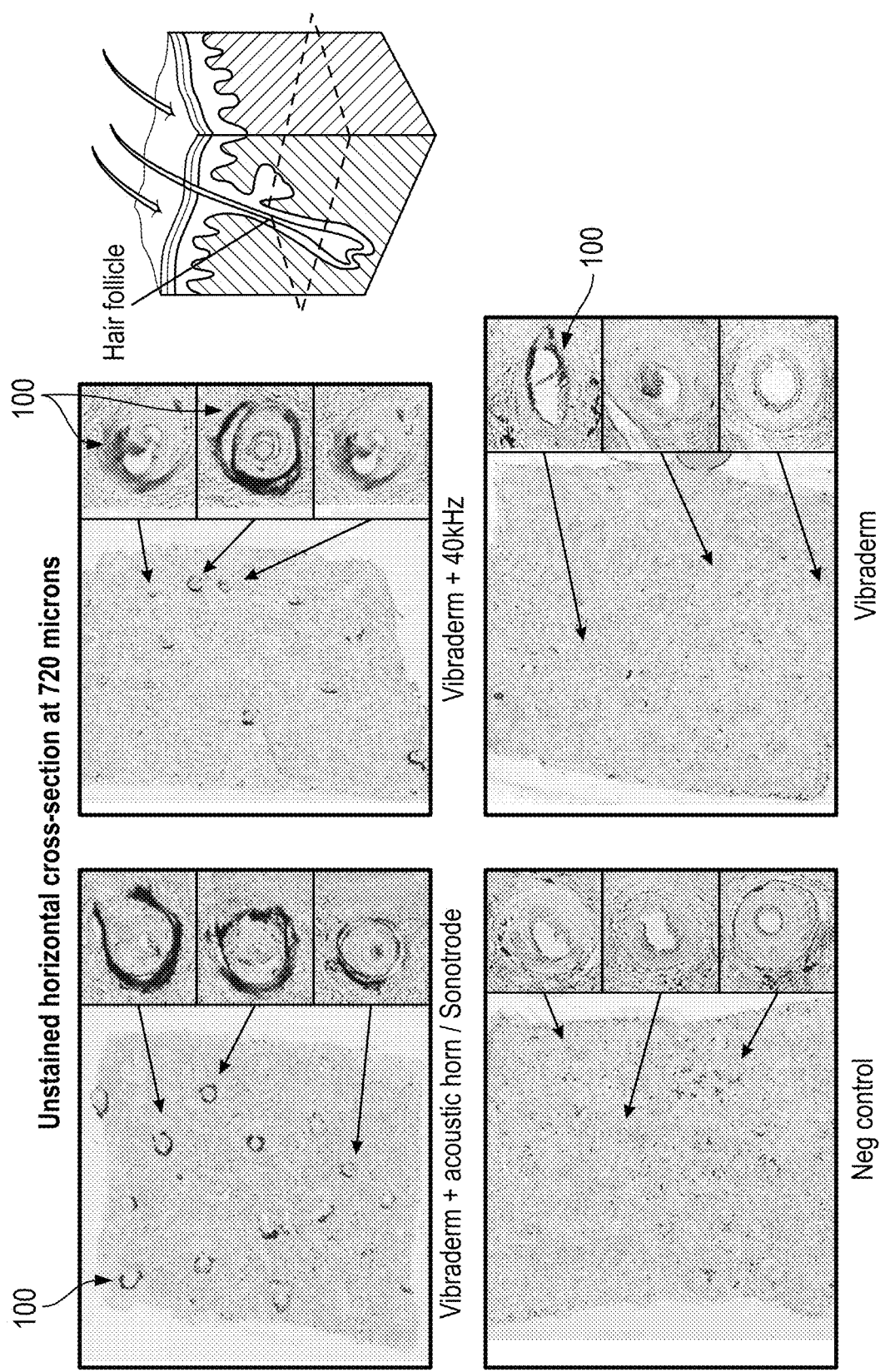
FIG. 21 is illustrative of images taken of tissue sections at approximately 720 microns deep of composition delivery within tissue samples using various embodiments of delivery devices. For the delivery device embodiment of a vibration device (Vibraderm) plus acoustic horn/sonotrode ultrasound energy, there is a markedly increase in the total amount of composition delivered (100) and number of follicles that the composition is delivered to over the other delivery embodiments alone. At levels of approximately 720 microns, there is also a significant increase in delivery of the composition with vibration device (Vibraderm) plus 30-40 kHz ultrasound (flat transducer) over the vibration device alone.

FIG. 21 includes images from unstained horizontal cross-sections at 720 microns in depth below the skin surface, illustrating the distribution of composition 100 from the experiment. The images include distribution of the composition 100 for a negative control (incubation on the skin surface without a delivery device 200), the first delivery device 210 (Vibraderm), a combination of both the first delivery device 210 (Vibraderm) and the third delivery device 230 (36 kHz non-pulsed ultrasound), and a combination of both the first delivery device 210 (Vibraderm) and the second delivery device 220 (30 kHz-40 kHz ultrasound device with a sonotrode). FIG. 21 is illustrative of images taken of tissue sections at approximately 720 microns deep of composition delivery within tissue samples using various embodiments of delivery devices. For the delivery device embodiment of a vibration device (Vibraderm) plus acoustic horn/sonotrode ultrasound energy, there is a markedly increase in the total amount of composition delivered (100) and number of follicles that the composition is delivered to over the other delivery embodiments alone. At levels of approximately 720 microns, there is also a significant increase in delivery of the composition with vibration device (Vibraderm) plus 30-40 kHz ultrasound (flat transducer) over the vibration device alone.

Figure 22:
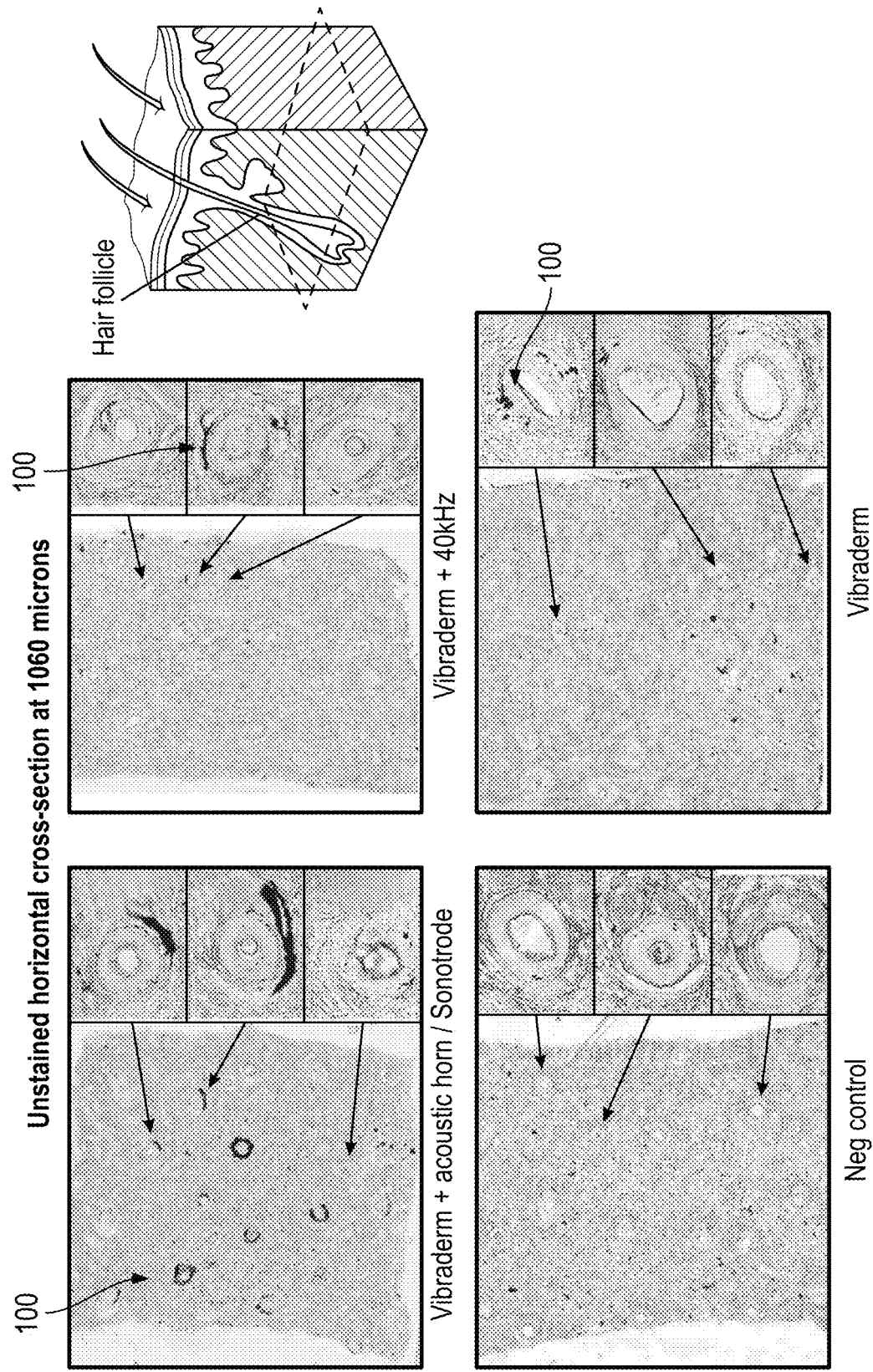
FIG. 22 is illustrative of images taken of tissue sections at approximately 1060 microns deep of composition delivery within tissue samples using various embodiments of delivery devices. For the delivery device embodiment of a vibration device plus acoustic horn/sonotrode ultrasound energy, there is a markedly increase in the total amount of composition delivered (100) and number of follicles that the composition is delivered to over the other delivery embodiments alone. At this depth of approximately 1060 microns, the amount delivery of the composition by the other delivery device embodiments has significantly decreased.

FIG. 22 includes images from unstained horizontal cross-sections at 1060 microns in depth below the skin surface, illustrating the distribution of composition 100 from the experiment. The images include distribution of the composition 100 for a negative control (incubation on the skin surface without a delivery device 200), the first delivery device 210 (Vibraderm), a combination of both the first delivery device 210 (Vibraderm) and the third delivery device 230 (rey), and a combination of both the first delivery device 210 (Vibraderm) and the second delivery device 220 (30 kHz-40 kHz ultrasound device with a sonotrode). FIG. 22 is illustrative of images taken of tissue sections at approximately 1060 microns deep of composition delivery within tissue samples using various embodiments of delivery devices. For the delivery device embodiment of a vibration device plus acoustic horn/sonotrode ultrasound energy, there is a markedly increase in the total amount of composition delivered (100) and number of follicles that the composition is delivered to over the other delivery embodiments alone. At this depth of approximately 1060 microns, the amount delivery of the composition by the other delivery device embodiments has significantly decreased.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Other embodiments of the invention will be apparent to those skilled in the art from consideration of the specification and practice of the invention disclosed herein. It is intended that the specification and examples be considered as disclosing certain embodiments of the invention only, with a true scope and spirit of the invention being indicated by the following claims.

As will be understood by the skilled artisan, the subject matter described herein may be embodied in other specific forms without departing from the spirit or essential characteristics thereof. The foregoing embodiments are therefore to be considered in all respects illustrative rather than limiting on the invention described herein. While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "identifying a target region of skin tissue" include "instructing the identification of a target region of skin tissue." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" or "substantially" include the recited numbers. For example, "about 3 mm" includes "3 mm." The terms "approximately", "about", and "substantially" as used herein represent an amount or characteristic close to the stated amount or characteristic that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount or characteristic.

What is claimed:

1. A method of delivering a composition to a target tissue under a skin surface, comprising:
    applying a composition to a skin surface,
    distributing the composition from the skin surface to a target tissue under the skin surface,
    wherein said composition comprises a plurality of unassembled plasmonic nanoparticles in a solution,
    wherein the unassembled plasmonic nanoparticles comprise a conductive metal portion,
    wherein the conductive metal portion comprises at least one of gold or silver, wherein the unassembled plasmonic nanoparticles comprise a coating that coats the conductive metal portion,
    wherein said coating facilitates selective removal from the skin surface;
    wherein the coating comprises at least one of silica or polyethylene glycol (PEG),
    selectively removing the composition from the skin surface, while leaving the composition localized within a sebaceous gland; and
    irradiating the composition with a light source thereby inducing a plurality of surface plasmons in said unassembled plasmonic nanoparticles, wherein inducing the plurality of surface plasmons generates localized heat in the target tissue.

2. The method of claim 1, wherein the composition is applied with at least one of: an ultrasound device, a sonic force device, a massage device, a high pressure air flow device, a high pressure liquid flow device, and a vacuum device, or a dermabrasion device.

3. The method of claim 1, further comprising pre-treating the skin surface prior to irradiating the composition, wherein pre-treating the skin surface comprises hair removal.

4. The method of claim 1, wherein the unassembled plasmonic nanoparticles have a concentration of $10^9$ to $10^{13}$ particles per ml of the solution.

5. The method of claim 1, wherein the unassembled plasmonic nanoparticles comprise a solid, conducting silver core and a silica coating.

6. The method of claim 1, wherein the conductive metal portion is a silver nanoplate, and wherein the coating is less conductive than the conductive metal portion.

7. The method of claim 1, wherein the conductive metal portion is a nanoplate, and wherein the nanoplate has a peak absorption wavelength in a range of 750 nm to 1200 nm.

8. The method of claim 1, wherein the coating comprises silica, wherein the target tissue comprises at least one of a sebocyte and sebum.

9. The method of claim 1, wherein the unassembled plasmonic nanoparticles have an optical density of 10 O.D. to 5,000 O.D. within an infrared light range.

10. The method of claim 1, further comprising the step of redistributing the solution with a sonic mechanical vibration device that comprises bubble formation or liquid microstreaming.

11. The method of claim 1, further comprising pretreating the skin surface to increase delivery of the unassembled plasmonic nanoparticles to the sebaceous gland with at least one of the group consisting of shaving, waxing, peeling, cyanoacrylate surface peeling, a calcium thioglycolate treatment, a surface exfoliation, a mechanical exfoliation, a salt glow, a microdermabrasion, a chemical exfoliation, a chemical exfoliation with an enzyme, a chemical exfoliation with alphahydroxy acid, and a chemical exfoliation with betahydroxy acid.

12. The method of claim 1, further comprising: pretreating the skin surface to increase delivery of the unassembled plasmonic nanoparticles to the pilosebaceous unit with at least one of the group consisting of shaving, waxing, peeling, cyanoacrylate surface peeling, a calcium thioglycolate treatment, a surface exfoliation, a mechanical exfoliation, a salt glow, a microdermabrasion, a chemical exfoliation, a chemical exfoliation with an enzyme, a chemical exfoliation with alphahydroxy acid, and a chemical exfoliation with betahydroxy acid; wherein irradiating the solution of unassembled plasmonic nanoparticles comprises exposing the solution of unassembled plasmonic nanoparticles to the energy at a wavelength of between 750 nm and 1200 nm to induce a plurality of surface plasmons in said unassembled plasmonic nanoparticles, thereby treating acne at said sebaceous gland.

13. The method of claim 1, further comprising applying the composition with a mechanical vibration device that is a sonic force device; wherein irradiating the solution of unassembled plasmonic nanoparticles with the energy comprises an infrared light source wavelength of between 750 nm and 1200 nm to induce a plurality of surface plasmons in said unassembled plasmonic nanoparticles, thereby treating an acne at said sebaceous gland.

14. The method of claim 1, wherein selectively removing the composition from the skin surface comprises using water or alcohol to remove the composition from the skin surface while leaving the composition localized within a pilosebaceous unit.

15. The method of claim 1, wherein selectively removing the composition from the skin surface comprises using water or alcohol to remove the composition from the skin surface while leaving the composition localized within a sebaceous gland.

* * * * *